(12) United States Patent
Antony

(10) Patent No.: US 12,121,556 B2
(45) Date of Patent: *Oct. 22, 2024

(54) MEDICINAL COMPOSITION OF AMARANTH ORIGIN FOR CARDIOVASCULAR TREATMENT

(71) Applicant: ARJUNA NATURAL PRIVATE LIMITED, Alwaye (IN)

(72) Inventor: Benny Antony, Ankamaly (IN)

(73) Assignee: ARJUNA NATURAL PRIVATE LIMITED, Alwaye (IN)

( * ) Notice: Subject to any disclaimer, the term of this patent is extended or adjusted under 35 U.S.C. 154(b) by 0 days.

This patent is subject to a terminal disclaimer.

(21) Appl. No.: 17/718,249

(22) Filed: Apr. 11, 2022

(65) Prior Publication Data

US 2022/0273745 A1 Sep. 1, 2022

Related U.S. Application Data

(60) Division of application No. 16/752,916, filed on Jan. 27, 2020, now Pat. No. 11,338,005, which is a continuation-in-part of application No. 16/710,152, filed on Dec. 11, 2019, now Pat. No. 11,382,943, which is a division of application No. 16/457,022, filed on Jun. 28, 2019, now Pat. No. 10,548,932, said application No. 16/752,916 is a continuation of application No. PCT/IB2018/055773, filed on Aug. 1, 2018, said application No. 16/457,022 is a division of application No. 15/435,387, filed on Feb. 17, 2017, now Pat. No. 10,383,903, which is a continuation of application No. 14/975,251, filed on Dec. 18, 2015, now Pat. No. 9,610,311, which is a continuation of application No. PCT/IN2014/000430, filed on Jun. 26, 2014.

(30) Foreign Application Priority Data

Jun. 28, 2013 (IN) .......................... 2861/CHE/2013
Aug. 2, 2017 (IN) .......................... 201741027538

(51) Int. Cl.
| | | |
|---|---|---|
| *A61K 36/21* | (2006.01) | |
| *A61K 31/12* | (2006.01) | |
| *A61K 31/192* | (2006.01) | |
| *A61K 31/194* | (2006.01) | |
| *A61K 31/56* | (2006.01) | |
| *A61K 33/00* | (2006.01) | |
| *A61K 36/47* | (2006.01) | |

(52) U.S. Cl.
CPC ............. *A61K 36/21* (2013.01); *A61K 31/12* (2013.01); *A61K 31/192* (2013.01); *A61K 31/194* (2013.01); *A61K 31/56* (2013.01); *A61K 33/00* (2013.01); *A61K 36/47* (2013.01); *A61K 2236/15* (2013.01); *A61K 2236/19* (2013.01); *A61K 2236/333* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| | | | |
|---|---|---|---|
| 7,736,679 | B2 | 6/2010 | Antony |
| 7,777,074 | B2 | 8/2010 | Kramer et al. |
| 7,879,373 | B2 | 2/2011 | Antony |
| 7,883,728 | B2 | 2/2011 | Antony |
| 8,034,836 | B2 | 10/2011 | Kramer et al. |
| 8,048,921 | B2 | 11/2011 | Kramer et al. |
| 8,153,172 | B2 | 4/2012 | Antony |
| 8,178,572 | B2 | 5/2012 | Kramer et al. |
| 8,183,288 | B2 | 5/2012 | Kramer et al. |
| 8,197,869 | B2 | 6/2012 | Antony |
| 8,298,589 | B1 | 10/2012 | Bryan |
| 8,303,995 | B1 | 11/2012 | Bryan |
| 8,329,233 | B2 | 12/2012 | Antony |
| 8,435,570 | B1 | 5/2013 | Bryan et al. |
| 8,455,531 | B2 | 6/2013 | Kramer et al. |
| 8,466,187 | B2 | 6/2013 | Kramer et al. |
| 8,569,368 | B2 | 10/2013 | Kramer et al. |
| 8,569,369 | B2 | 10/2013 | Kramer et al. |
| 8,623,431 | B2 | 1/2014 | Antony |
| 8,859,020 | B1 | 10/2014 | Antony |
| 8,895,087 | B2 | 11/2014 | Antony |

(Continued)

FOREIGN PATENT DOCUMENTS

| | | |
|---|---|---|
| CN | 101347252 A | 1/2009 |
| CN | 101856049 B | 10/2010 |

(Continued)

OTHER PUBLICATIONS

Ashok Kumar, BS, Lakshman, K, Jayaveena, KN, Nandeesh, R, Manoj, B, Ranganayakulu, D, Comparative in Vitro Anthelmintic activity of Three plants from the Amaranthaceae family, Arch. Biol. Sci., Belgrade, 62 (1): 185-189 (2010).

Maiyo, ZC, Ngure, RM, Matasyoh, JC, Chepkorir, R, Phytochemical constituents and Antimicrobial activity of Leaf Extracts of three *Amaranthus* plant species, African Journal of Biotechnology vol. 9 (21) : 3178-3182, May 24, 2010. Academic Journals.

Antara, C, Evaluation of Physiochemical and Phytochemical parameters of Amaranthus Spinosus leaves, International Research Journal of Pharmacy,, 3 (10): 210-211 (2012).

Tsuchiya, K, Kanematsu, Y, Yoshizumi, M, Ohnishi, H, Kirima, K, Izawa, Y, Shikishima, M, Ishida, T, Kondo, S, Kagami, S , Takiguchi, Y and Tamaki, T, Nitrite is an alternative source of NO in vivo, Am J Physiol Heart Circ Physiol 288: H2163-H2170 (2005). American Physiological Society.

(Continued)

*Primary Examiner* — Michael V Meller
(74) *Attorney, Agent, or Firm* — Jyoti C Iyer

(57) ABSTRACT

A medicinal composition having a nitrate enriched extract of Amaranth for the prevention and treatment of myocardial ischemia-reperfusion injury, and for the improvement of cardioprotective health and cardio renal protection. A method for the prevention and treatment of myocardial ischemia-reperfusion injury, method of improving cardioprotective health and cardio renal protection by using the composition having a nitrate enriched extract of Amaranth.

7 Claims, 28 Drawing Sheets

(56) References Cited

U.S. PATENT DOCUMENTS

| | | | |
|---|---|---|---|
| 8,952,045 | B1 | 2/2015 | Kramer et al. |
| 8,952,046 | B1 | 2/2015 | Kramer et al. |
| 8,952,047 | B1 | 2/2015 | Kramer et al. |
| 8,957,100 | B1 | 2/2015 | Kramer et al. |
| 8,957,101 | B1 | 2/2015 | Kramer et al. |
| 8,993,013 | B2 | 3/2015 | Antony |
| 9,006,493 | B2 | 4/2015 | Kanaya |
| 9,180,140 | B2 | 11/2015 | Lundberg et al. |
| 9,492,402 | B2 | 11/2016 | Antony |
| 9,861,677 | B2 | 1/2018 | Antony |
| 9,878,040 | B2 | 1/2018 | Antony |
| 10,159,654 | B2 | 12/2018 | Antony |
| 10,286,027 | B2 | 5/2019 | Antony |
| 10,485,843 | B2 | 11/2019 | Antony |
| 10,512,616 | B2 | 12/2019 | Antony |
| 10,543,277 | B2 | 1/2020 | Antony |
| 10,555,968 | B2 | 2/2020 | Lundberg et al. |
| 2002/0192312 | A1 | 12/2002 | Whittle et al. |
| 2003/0124204 | A1 | 7/2003 | Sweet |
| 2006/0141063 | A1 | 6/2006 | Palpu et al. |
| 2011/0311661 | A1 | 12/2011 | Behr et al. |
| 2012/0321724 | A1 | 12/2012 | Bryan |
| 2013/0071371 | A1 | 3/2013 | Bryan et al. |
| 2013/0071494 | A1 | 3/2013 | Bryan |
| 2015/0352147 | A1 | 12/2015 | Lundberg et al. |
| 2016/0101138 | A1 | 4/2016 | Antony |
| 2016/0228339 | A1 | 8/2016 | Glymur |
| 2017/0151298 | A1 | 6/2017 | Antony |
| 2017/0202785 | A1 | 7/2017 | Antony |

FOREIGN PATENT DOCUMENTS

| | | |
|---|---|---|
| CN | 102132750 B | 5/2012 |
| CN | 102813837 A | 12/2012 |
| CN | 103623280 A | 3/2014 |
| WO | WO 2008/105730 A1 | 9/2008 |
| WO | WO 2008/105731 A1 | 9/2008 |
| WO | WO 10/35253 A1 | 4/2010 |
| WO | WO 2013/026000 A1 | 2/2013 |

OTHER PUBLICATIONS

Umar, KJ, Hassan, LG, Dangoggo, SM, Maigandi, SA, Sani, NA, Nutritional and Anti-nutritional profile of spiny Amaranth (*Amaranthus viridis* linn), Studia Universitatis "Vasile Goldiş", Seria Ştiinţele Vieţii, vol. 21(4), issue 4: pp. 727-737 (2011).
Srivastava, R, Nutritional Quality of Some Cultivated and Wild species of *Amaranthus* L., International Journal of Pharmaceutical Science and Research, 2(12): 3152-3156 (2011).
Akubugwo, IE, Obasi, NA, Chinyere, GC and Ugbogu, AE, Nutritional and chemical value of *Amaranthus hybridus* L. leaves from Afikpo, Nigeria, African Journal of Biotechnology ,6 (24): 2833-2839 (2007).
Soetan, KO, Aiyelaagbe, O.O, The need for bioactivity-safety evaluation and conservation of medicinal plants—A review, Journal of Medicinal Plants Research, 3(5): 324-328 (2009).
Prakash, D, Pal, M, Nutritional and Antinutritional composition of vegetable and grain Amaranth leaves, Journal of the Science of Food and Agriculture, 57(4): 573-583 (1991).
Bharadwaj, K, Murty, AS, An Investigation of Edible Plants for Soluble Oxalates and Calcium Oxalate Crystals, Bulletin of Medico-Ethno-Botanical Research, XII (3-4):153-156 (1991).
International search report for PCT/IN2014/000430 dated Nov. 12, 2014.
Noonan, SC, Savage, GP, Oxalate content of foods and its effect on Human, Asia Pacific J Clin Nutr 8(1): 64-74 (1999).
Arslan, A, Uzun, M, Does the lower Nitric Oxide level cause cardiovascular changes in major depressed Women? European Review for Medical and Pharmacological Sciences, 12: 309-313 (2008).
Mnkeni, AP, Masika, P, Maphaha, M, Nutritional Quality of Vegetable and Seed from different accessions of Amaranthus in South Africa, Water SA 33(3) (Special Edition) : 377-380 (2007).
Oloyede, FM, Oloyede, FA, Obuotor E, M, Effect of Plant Maturity on the Antioxidant Profile of *Amaranthus cruentus* L. and *Celosia argentea* L., Bull. Env. Pharmacol. Life Sci. 2 (2): 18-21 (2013).
Ahmed, SA, Hanif, S, Iftkhar, T, Phytochemical Profiling with Antioxidant and Antimicrobial Screening of *Amaranthus viridis* L. Leaf and Seed Extracts, Open Journal of Medical Microbiology, 3:164-171 (2013).
Kenjale, AA, Ham, KL, Stabler, T, Robbins, JL, Johnson, JL, VanBruggen, M, Privette, G, Yim, E, Kraus, WE, Allen, JD, Dietary Nitrate Supplementation Enhances Exercise Performance in Peripheral Arterial Disease, J Appl Physiol 110: 1582-1591 (2011).
Ignarro, LJ, Fukuto, JM, Griscavage, JM, Rogers, NE, Byrns, RE, Oxidation of Nitric oxide in Aqueous Solution to Nitrite but not Nitrate: Comparison with Enzymatically formed Nitric oxide from L-arginine, Proc. Natl. Acad. Sci. USA, 90: 8103-8107, (1993).
Ogbadoyi, EO, Musa, A, Oladiran, JA, Ezenwa, Mis, Akanya, FH, Effect of Processing methods on Some Nutrients, Antinutrients and Toxic Substances in *Amaranthus cruentus*, International Journal of Applied Biology and Pharmaceutical Technology, 2(2) :487-502 (2011).
Mou, B, Evaluation of Oxalate Concentration in the U.S. Spinach Germplasm Collection, Hort Science 43(6): 1690-1693(2008).
European Food Safety Authority, Nitrate in vegetables Scientific Opinion of the Panel on Contaminants in the Food chain, Opinion of the Scientific panel on contaminants in the food chain on a request from the European Commision to perform a scientific risk assessment in nitrate in vegetables, The EFSA Journal, 689: 1-79 (2008).
Larsen, FJ, Weitzberg, E, Lundberg, JO, Ekblom, B, Effects of dietary nitrate on oxygen cost during exercise, Acta Physiol, 191, 59-66(2007).
Eight (8) pages of Supplementary partial European search report dated Nov. 10, 2016.
Feng, XT, Qin, CB, Leng, J, Tang, QL, Shi, H, Zhai, LN and Li, SL, Yidiyin, a Chinese Herbal Decoction, Improves Erectile Dysfunction in Diabetic Patients and Rats through the N)-cGMP Pathway, Biosci.Biotechnol. Biochem. 76(2): 257-263 (2012).
Barba De La Rosa, AP, Montoya, AB, Martmez-Cuevasb, P, Hernandez-Ledesmac, B, Leon-Galvan, MF, De Leon-Rodrigueza, A, Gonzalez, C, Tryptic amaranth glutelin digests induce endothelial nitric oxide production through inhibition of ACE: Antihypertensive role of amaranth peptides, Nitric Oxide 23,106-111 (2010).
Fourteen (14) pages of Extended European search report dated Feb. 21, 2017.
Aguirre-Crespo, F, Castillo-Espana, P. Villalobos-Molina, R, Lopez-Guerrero, JJ, Estrada-Soto, S, Vasorelaxant effect of Mexican medicinal plants on isolated rat arota, Pharmaceutical Biology, 43: 540-546(2005).
Martirosyan, DM, Miroshnichenko, LA, Kulakova, SN, Pogojeva, AV, Zoloedov, VI, Amaranth oil application for coronary heart disease and hypertension, Lipids in Health and Disease, 6:1(2007).
Two (2) pages of international search report dated Feb. 11, 2019.
Lutz, J, Enzymatic hydrolysis of whole grain Amarath,1-60(2008).
Webb, AJ, Patel, N, Loukogeorgakis, S, Okorie, M. Aboud, Z, Misra, S, Rashid, R, Miall, P, Deanfield, J, Benjamin, N, Macallister, R, Hobbs, AJ, Ahluwalia, A, Acute blood pressure lowering, vasoprotective and anti-platelet properties of dietary nitrate via bioconversion to nitrite, Hypertension, 51 (3): 784-790, Mar. 2008.
Siervo, M, Lara, J, Ogbonmwan, I, Mathers, JC, Inorganic Nitrate and Beetroot juice supplementation reduces blood pressure in adults; A systematic review and meta-analysis, The Journal of nutrition, 143 (6): 818-826 (2013).
Uwah, EI, Abah, J, Ndahi, NP, Ogugbuaja, VO, Concentration levels of Nitrate and Nitrite in soils and some leafy vegetables obtained in Maiduguri, Nigeria, Journal of applied sciences in Environmental sanitation, 4 (3): 233-244 (2009).
Celine, VA, Shankaran, SS, Seema, S, Deepa, SN, Sreelathakumary, I, Vahab, MA, Characterization and Evaluation of Vegetable Amaranthus (*Amaranthus tricolor* L.) for High Yield, Quality and Resistance to

(56) References Cited

OTHER PUBLICATIONS

Rhizoctonia solani, In I International Conference on Indigenous Vegetables and Legumes, 752: 447-452, (2007).

Thite, AH, Menon, GS, Effect of Sewage Irrigation on Nitrate accumulation and Nitrate reductase activity in leafy Vegetables, Pakistan Journal of Biological Science, ISSN 1028-8880,15(1): 34-38(2012).

Hord, NG, Tang, Y, Bryan, NS, Food sources of nitrates and nitrites: the physiologic context for potential health benefits, American journal of clinical nutrition, 90(1): 1-10 (2009).

Guil, JL, Garcia, IR, Torija, E, Nutritional and toxic factors in selected wild edible plants, Plant foods for human nutrition, 51(2): 99-107 (1997).

Quintero, KM, Rojas, RM, Molina, R, Sanchez-Urdaneta, AB, Chemical composition of Amaranthus dubius: an alternative for human and animal feeding, Rev. Fac. Agron. (LUZ), 28 supl. (1):619-627(2011).

Larsen, FJ, Ekblom, B, Sahlin, B, Lundberg, JO, Weitzberg, E, Effects of dietary nitrate on Blood Pressure in Healthy Volunteers, New England Journal of Medicine, 355;26(2006).

Gaiser, M, Rathjen, A, Spiess, Wel, Nitrate Extraction during Blanching of spinach, Lebensm.—Wiss. U.—Technol., 30, 432-435 (1996).

2(two) pages of International Search Report dated Jan. 15, 2019.

Khoo, HE, Azlan, A, Ismail, A, Abas, F, Influence of different extraction media on phenolic contents and antioxidant capacity of defatted dabai (*Canarium odontophyllum*) fruit, Food Analytical methods, 5:339-350 (2012).

Leyva-Lopez, NE, Vasco, N, Barba De La Rosa, AP, Paredes-Lopez, O, Amaranth seed proteins: Effect of defatting on extraction yield and on electrophoretic patterns, Plant foods for human Nutrition 47 (1): 49-53, (1995).

Hussain, ST, Khan, GA, Shabeer, M, Solubility of oxalic acid, Asian J. Research Chem. 5(11): Nov. 2012.

Grocott, SC, Harrison, IR, Two new oxalate removal processes, Fourth International Alumina Quality Workshop, 1996.

Sowbhagya, HB, Chitra, VN, Enzyme-Assisted Extraction of flavorings and colorants from plant materials, Critical reviews in food science and Nutrition, 50(2):146-161 (2010).

Dharmananda, S, Dosage and form of herbs Decoction, Dried decoctions, powders, pills, Etc, Institute of Traditional medicine.

Fiore, K, Nitric Oxide Works When BP Drugs Fail, MedPage Today, 2012.

Zeshan, Evaporators for Pharmaceutical Industry, Food Industry & Chemical Industry, (2010).

Weitzberg, E, Hezel, M, Lundberg, JO, Nitrate-Nitrite-Nitric Oxide Pathway Implications for Anesthesiology and Intensive Care, Anesthesiology, 113:1460-75 (2010).

Stokes, G.S, Systolic Hypertension in the Elderly: Pushing the Frontiers of Therapy—A Suggested New Approach, The Journal of Clinical Hypertension, 6(4): 192-197, Apr. 2004.

Da Costa, LM, Tronto, J, Constantino, VRL, Fonseca, MKA, Oliveira, AP, Da Costa, MR, Extraction and Concentration of Biogenic Calcium Oxalate from Plant Leaves, R. Bras. Ci. Solo, 33:729-733 (2009).

Puri, M, Sharma, D. Barrow, CJ, Enzyme-assisted extraction of bioactives from plants, Trends in Biotechnology, 30 (1): 37-44, Jan. 2012.

Srinivasakannan, C, Vasanthakumar, R, Iyappan, K, Rao, PG, A Study on Crystallization of Oxalic Acid in Batch Cooling Crystallizer, Chem. Biochem. Eng. Q. 16 (3) 125-129 (2002).

Ghosh, SM, Kapil, V, Fuentes-Calvo, I, Bubb, KJ, Pearl, V, Milsom, AB, Khambata, R, Maleki-Toyserkani, S, Yousuf, M, Benjamin, N, Webb, AJ, Caulfield, MJ, Hobbs, AJ, Ahluwalia, A, Enhanced Vasodilator Activity of Nitrite in Hypertension Critical Role for Erythrocytic Xanthine Oxidoreductase and Translational Potential, Hypertension, 61:1091-1102 (2013).

Kutaish, N, Aggarwal, P. Dollimore, D, Thermal analysis of calcium oxalate samples obtained by various preparative routes, Thermochimica Acta 297: 131-137 (1997).

Ozsoy, N, Yilmaz, T, Kurt, O, Can, A, Yanardag, R, In vitro antioxidant activity of *Amaranthus lividus* L, Food Chemistry 116 867-872 (2009).

Sarker, U, Motaher Hossain, MD, Oba, S, Nutritional and antioxidant components and antioxidant capacity in green morph Amaranthus leafy vegetable, Scientific Reports, 10:1336, (2020).

Antony, B, Benny, M, Rao, SB, Enhancing the Absorption of Curcuminoids, Spice India; 23-26 (2005).

Benny, M, Antony, B, Bioavailability of Biocurcumax™ (BCM-095™), Spice India;11-15, (2006).

Antony, B, Merina, B, Iyer, VS, Judy, N, Lennertz, K, Joyal, S, A pilot cross-over study to evaluate human oral bioavailability of BCM-95® CG (Biocurcumax™), a novel bioenhanced preparation of curcumin, Indian journal of pharmaceutical sciences, 70(4):445(2008).

MEDICINAL COMPOSITION OF AMARANTH ORIGIN FOR CARDIOVASCULAR TREATMENT

This Application is a divisional of U.S. application Ser. No. 16/752,916, filed Jan. 27, 2020, which is a continuation of PCT/IB2018/055773 filed Aug. 1, 2018, which claims the benefit of Indian Provisional Appl. Ser. No. INDIA 201741027538 filed Aug. 2, 2017, and this application is a continuation-in-part of U.S. application Ser. No. 16/710,152 filed Dec. 11, 2019, which is a divisional of U.S. application Ser. No. 16/457,022 filed Jun. 28, 2019 issued as U.S. Pat. No. 10,548,932, which is a divisional of U.S. application Ser. No. 15/435,387 filed Feb. 17, 2017 issued as U.S. Pat. No. 10,383,903, which is a continuation of U.S. application Ser. No. 14/975,251 filed Dec. 18, 2015 issued as U.S. Pat. No. 9,610,311, which is a continuation of International Appl. Ser. No. PCT/IN2014/000430 filed Jun. 26, 2014, which claims the benefit of Indian Provisional Appl. Ser. No. INDIA 2861/CHE/2013 filed Jun. 28, 2013, all of which are incorporated by reference in entirety.

FIELD

A medicinal composition obtained from a plant extract for the prevention and treatment of myocardial ischemia-reperfusion injury, for the improvement of cardioprotective health and cardio renal protection.

A method for the prevention and treatment of myocardial ischemia-reperfusion injury, method of improving cardioprotective health and cardio renal protection by using the composition from a plant extract.

BACKGROUND

Cardiovascular failure following myocardial infarction (MI) is the leading cause of mortality and morbidity globally and carrying an enormous medical burden. It has been reported that 17.3 million people had died from cardiac disorders in 2008 and strikingly over 80% of death were reported in low and middle-income countries. Due to changing lifestyles, dietary patterns and physical inactivity, MI is an increasing contributor to cardiac death. During myocardial ischemia, the blood supply to heart is decreased, leading to a decline in oxygen and nutrient supply. Reperfusion of an ischemic myocardium is necessary to avoid further damage and to restore the normal physiology of the heart. However, abrupt reperfusion of an ischemic myocardium is not without risk, it produces further damage of myocardium, described as ischemia-reperfusion (I/R) injury. Reperfusion induced reactive oxygen or nitrogen species (ROS or RNS), including superoxide radicals, hydrogen peroxide, hydroxyl radicals, singlet oxygen, nitric oxide, and peroxynitrite plays major contribution to myocardial I/R injury. There are several chemotherapeutic agents used for preventing and treating cardiovascular disease. But associated systemic side effects is a major clinical hurdle. Besides drug therapy, changing life style, dietary modification and supplementation of herbal based formulation enriched with antioxidant have shown protective effects against CVDs without reducing their therapeutic efficacy.

Hypercholesterolemia (HC) and hypertension (HT) are both major risk factors for the development and progression of atherosclerotic heart disease, and their co-existence has been associated with an increased incidence of cardiac events in clinical studies. Hypertension is often asymptomatic and was characterized several decades ago as a major cardiovascular risk factor. Hypertension accounts for an estimated 54 percent of all strokes and 47 percent of all ischemic heart disease events globally. Various epidemiological and clinical studies have demonstrated an association between hypertension and the main complications of atherosclerotic arterial disease: stroke, myocardial infarction (MI), heart failure (HF), peripheral artery disease, and chronic renal failure (CRF).

Moreover, there is a growing trend and clinician interest towards the usage of herbal medicine as a protective strategy against cardiovascular related problems such as myocardial-I/R injury. Curcumin, a polyphenolic compound derived from *Curcuma longa* is known to have numerous beneficial effects, such as anti-inflammation, anti-apoptosis, antiproliferation and anti-oxidant. Preclinical and clinical studies have been reported preventive action of curcumin in MI, hypertension, and diabetic cardiomyopathy. Moreover, Curumin based combination of formulation containing curcumin and antioxidant rich flavonoids have been shown and proven to attenuate myocardial fibrosis by modulating the expression of the Ang II receptors, AT1 and AT2, in Ang II-treated rats.

The disclosure is related to the therapeutic effect and putative molecular mechanisms of Amaranth extract enriched with nitrate against myocardial via left anterior descending coronary artery (LAD) method is disclosed.

Furthermore, the cardio protective effect of Amaranth extract enriched with nitrate is strengthened in the presence of bio-enhanced curcumin composition. The protective effect of herbal formulations combination is achieved through decreasing the oxidative stress and repressing the inflammatory and apoptosis cascade while maintaining vasodilatory action via cGMP-NO pathway.

Chinese patent CN 101856049 discloses grain amaranth lactobacillus fermented yogurt, which can prevent hypertension, hyperlipoidemia, cardiovascular and cerebrovascular diseases, diabetes mellitus, obesity and digestive system diseases after long-term drinking.

Russian patent RU2597788 refers to medicine which can be used for prevention of complications induced by isoniazid. Amaranth seed oil is used along with isoniazid to reduce the severity of metabolic and morphological hepatic disorders in acute disorders induced by isoniazid, reduction of intensity of pathological changes in the cardiovascular system and the central nervous system.

Danik et al revealed inclusion of amaranth oil in the diet has a beneficial action upon the clinical presentation of Coronary Heart Disease and Hypertension. Amaranth oil decreases the amount of total cholesterol, triglycerides, LDL and VLDL significantly.

The above said prior art are directed towards the use of oil extracted from the seed or kernels of Amaranth, whereas the disclosure is directed towards a water soluble extract derived from the leaf and stem of Amaranth. Moreover the disclosure is directed towards the activity of nitrate in the Amaranth extract, whereas the oil disclosed in the seed oil of Amaranth is directed towards the activity of the fatty acid present in the oil. The oil extracted from the seed or kernels of Amaranth is devoid of any nitrate.

Another Chinese patent CN103341054 discloses a traditional Chinese medicine preparation for treating cardiovascular and cerebrovascular diseases. The effective constituents of the traditional Chinese medicine preparation consisting several raw material and globe amaranth is one among them. In another chinese patent CN10147252 discloses a rainbow healthcare drink consist of Chinese herb globe amaranth which is one among the different herbs used for preparing the drink.

Above two patents mentioned Globe amaranth, which is a plant from the family Amaranthaceae. Globe amaranth is a different species and genus compared to the plant Amaranth disclosed herein.

SUMMARY

A composition having a nitrate enriched extract of Amaranth for oral administration is disclosed. The nitrate enriched extract of Amaranth includes about 0.1% to about 70% nitrates; about 1% to about 40% potassium, and, about 0.1% total oxalic acid. In some embodiments, the composition of extract of Amaranth includes greater than about 20% to about 70% nitrates, about 1% to about 40% potassium, and, about 0.1% total oxalic acid. In some embodiments, the nitrate enriched extract of Amaranth includes about 9% nitrates, about 18% potassium, and, about 0.07% total oxalic acid. In some embodiments, the nitrate enriched extract of Amaranth includes about 18% nitrates, about 17% potassium, and, about 0.09% total oxalic acid. In some embodiments, the nitrate enriched extract of Amaranth includes about 70% nitrates, about 25% potassium, and, about 0.03% total oxalic acid. In some embodiments, the nitrate enriched extract of Amaranth is administered to a subject in need thereof at a dosage of about 100 mg to about 2000 mg. Some embodiments provide a dosage form of the composition of the nitrate enriched extract of Amaranth such as fast melt tablets, lozenge, candy, chewing gum, beverage, tablets, capsules, pills, or powders.

Some embodiments provide a method of preventing and treating myocardial ischemia-reperfusion injury by administering a composition having the nitrate enriched extract of Amaranth. Administering the composition results in a physiological parameter such as enhancing superoxide dismutase (SOD) activities, enhancing glutathione (GSH) activity, decreasing malondialdehyde (MDA) levels, lowering myocardial infarct size, lowering creatine kinase-MB (CK-MB), lowering lactate dehydrogenase (LDH) levels, decreasing the percentage of apoptosis, decreasing caspase-3 levels, increasing the level of cGMP, decreasing Troponin level, decreasing levels of IL-6 and TNF-α in plasma and tissue, decreasing NO levels, or decreasing myoglobin level.

Some embodiments provide a method of improving cardioprotective health by administering a composition having the nitrate enriched extract of Amaranth. Administering the composition having the nitrate enriched extract of Amaranth results in a parameter such as decreasing mean blood pressure, decreasing triglycerides, decreasing total cholesterol, decreasing LDL cholesterol, decreasing VLDL cholesterol, increasing HDL, decreasing myocardial degeneration, decreasing necrosis, decreasing fibrosis, or decreasing intima media thickness.

Some embodiments provide a method of providing cardio-renal protection by administering a composition having the nitrate enriched extract of Amaranth. Administering the composition having the nitrate enriched extract of Amaranth results in a parameter such as decreasing serum glutamate-oxaloacetate transaminase (SGOT), decreasing serum Glutamic-Pyruvic Transaminase (SGPT), decreasing urine N-acetyl-beta-d-glucosaminidase (NAG), decreasing urine Albumin, decreasing plasma Ang II, decreasing tissue TGF-β1, lowering trigylcerides, lowering total cholesterol, increasing HDL cholesterol, lowering LDL cholesterol, lowering blood pressure, increasing nitric oxide level in tissue and plasma, increasing cGMP level in plasma, increasing eNOS level in tissue, increasing mRNA expression of NO synthase, increasing mCOX, and/or improvement in endothelial function.

A combination composition for oral administration is disclosed. The combination composition has a) a nitrate enriched extract of Amaranth and a composition b) comprising a bio-enhanced turmeric formulation. The composition a) has about 0.1% to about 70% nitrates; about 1% to about 40% potassium, and, about 0.1% total oxalic acid. The composition b) has a curcuminoid mixture and an essential oil of turmeric. The curcuminoid mixture consists of curcumin, demethoxycurcumin and bisdemethoxycurcumin. The essential oil of curcumin has about 45% ar-turmerone, and weight ratio of curcuminoid mixture to essential oil of curcumin ranges from about 1:1 to about 99:1. The combination composition is administered either in a single dosage form having both the composition a) and the composition b). Or the combination composition is administered as two dosage forms separately: one of which is a dosage form having composition a) and a second dosage form which has composition b).

In some embodiments of the combination composition, the composition of nitrate enriched extract of Amaranth includes greater than about 20% to about 70% nitrates, about 1% to about 40% potassium, and, about 0.1% total oxalic acid. In some embodiments of the combination composition, the nitrate enriched extract of Amaranth includes about 9% nitrates, about 18% potassium, and, about 0.07% total oxalic acid. In some embodiments of the combination composition, the nitrate enriched extract of Amaranth includes about 18% nitrates, about 17% potassium, and, about 0.09% total oxalic acid. In some embodiments of the combination composition, the nitrate enriched extract of Amaranth includes about 70% nitrates, about 25% potassium, and, about 0.03% total oxalic acid.

In some embodiments of the combination composition, the nitrate enriched extract of Amaranth is administered to a subject in need thereof at a dosage of about 100 mg to about 2000 mg. Some embodiments of the combination composition provide a dosage form such as fast melt tablets, lozenge, candy, chewing gum, beverage, tablets, capsules, pills, or powders. Some embodiments provide a method of administering the combination composition. The method of administration can be 1) administering a single dosage form comprising a mixture of the composition a) and the composition b). Or the method of administration can be separately administering two dosage forms, wherein one dosage form includes the composition a) and a second dosage form includes the composition b), and wherein the dosage forms of the two methods of administration are selected from the group consisting of fast melt tablets, lozenge, candy, chewing gum, beverage, tablets, capsules, pills, and powder.

Some embodiments provide a method of preventing and treating myocardial ischemia-reperfusion injury by administering a combination composition having the nitrate enriched extract of Amaranth and the bio-enhanced turmeric formulation. Administering the combination composition results in a physiological parameter such as enhancing superoxide dismutase (SOD) activities, enhancing glutathione (GSH) activity, decreasing malondialdehyde (MDA) levels, lowering myocardial infarct size, lowering creatine kinase-MB (CK-MB), lowering lactate dehydrogenase (LDH) levels, decreasing the percentage of apoptosis, decreasing caspase-3 levels, increasing the level of cGMP, decreasing Troponin level, decreasing levels of IL-6 and TNF-α in plasma and tissue, decreasing NO levels, or decreasing myoglobin level.

Some embodiments provide a method of improving cardioprotective health by administering the combination composition having the nitrate enriched extract of Amaranth and bio-enhanced turmeric formulation. Administering the combination composition having the nitrate enriched extract of Amaranth results in a parameter such as decreasing mean blood pressure, decreasing triglycerides, decreasing total cholesterol, decreasing LDL cholesterol, decreasing VLDL cholesterol, increasing HDL, decreasing myocardial degeneration, decreasing necrosis, decreasing fibrosis, or decreasing intima media thickness.

Some embodiments provide a method of providing cardio-renal protection by administering a combination composition having the nitrate enriched extract of Amaranth and bio-enhanced turmeric formulation. Administering the combination composition having the nitrate enriched extract of Amaranth results in a parameter such as decreasing serum glutamate-oxaloacetate transaminase (SGOT), decreasing serum Glutamic-Pyruvic Transaminase (SGPT), decreasing urine N-acetyl-beta-d-glucosaminidase (NAG), decreasing urine Albumin, decreasing plasma Ang II, decreasing tissue TGF-β1, lowering trigylcerides, lowering total cholesterol, increasing HDL cholesterol, lowering LDL cholesterol, lowering blood pressure, increasing nitric oxide level in tissue and plasma, increasing cGMP level in plasma, increasing eNOS level in tissue, increasing mRNA expression of NO synthase, increasing mCOX, and/or improvement in endothelial function.

A combination composition for oral administration having a) a nitrate enriched extract of Amaranth and b) an extract of seed of *Emblica officinalis* is disclosed. The nitrate enriched extract of Amaranth has about 0.1% to about 70% nitrates; about 1% to about 40% potassium, and, about 0.1% total oxalic acid. The extract of seed of *Emblica officinalis* has about 6% to about 50% of triterpenoids, about 2% to about 20% of hydroxycinnamic acids, about 10% to about 60% of fatty acids. The combination composition is administered either in a single dosage form having both the composition a) and the composition b). Or the combination composition is administered as two dosage forms separately: one of which is a dosage form having composition a) and a second dosage form which has composition b).

In some embodiments of the combination composition, the composition of nitrate enriched extract of Amaranth includes greater than about 20% to about 70% nitrates, about 1% to about 40% potassium, and, about 0.1% total oxalic acid.

In some embodiments of the combination composition, the nitrate enriched extract of Amaranth includes about 9% nitrates, about 18% potassium, and, about 0.07% total oxalic acid.

In some embodiments of the combination composition, the nitrate enriched extract of Amaranth includes about 18% nitrates, about 17% potassium, and, about 0.09% total oxalic acid.

In some embodiments of the combination composition, the nitrate enriched extract of Amaranth includes about 70% nitrates, about 25% potassium, and, about 0.03% total oxalic acid. In some embodiments of the combination composition, the nitrate enriched extract of Amaranth is administered to a subject in need thereof at a dosage of about 100 mg to about 2000 mg.

Some embodiments of the combination composition provide a dosage form such as fast melt tablets, lozenge, candy, chewing gum, beverage, tablets, capsules, pills, or powders.

Some embodiments provide a method of administering the combination composition. The method of administration can be 1) administering a single dosage form comprising a mixture of the composition a) and the composition b). Or the method of administration can be separately administering two dosage forms, wherein one dosage form includes the composition a) and a second dosage form includes the composition b), and wherein the dosage forms of the two methods of administration are selected from the group consisting of fast melt tablets, lozenge, candy, chewing gum, beverage, tablets, capsules, pills, and powder.

Some embodiments provide a method of preventing and treating myocardial ischemia-reperfusion injury by administering a combination composition having the nitrate enriched extract of Amaranth and the extract of seed of *Emblica officinalis*. Administering the combination composition results in a physiological parameter such as enhancing superoxide dismutase (SOD) activities, enhancing glutathione (GSH) activity, decreasing malondialdehyde (MDA) levels, lowering myocardial infarct size, lowering creatine kinase-MB (CK-MB), lowering lactate dehydrogenase (LDH) levels, decreasing the percentage of apoptosis, decreasing caspase-3 levels, increasing the level of cGMP, decreasing Troponin level, decreasing levels of IL-6 and TNF-α in plasma and tissue, decreasing NO levels, or decreasing myoglobin level. Some embodiments provide a method of improving cardioprotective health by administering the combination composition having the nitrate enriched extract of Amaranth and extract of seeds of *Emblica officinalis*. Administering the combination composition having the nitrate enriched extract of Amaranth results in a parameter such as decreasing mean blood pressure, decreasing triglycerides, decreasing total cholesterol, decreasing LDL cholesterol, decreasing VLDL cholesterol, increasing HDL, decreasing myocardial degeneration, decreasing necrosis, decreasing fibrosis, or decreasing intima media thickness. Some embodiments provide a method of providing cardio-renal protection by administering a combination composition having the nitrate enriched extract of Amaranth and extract of seeds of *Emblica officinalis*. Administering the combination composition having the nitrate enriched extract of Amaranth results in a parameter such as decreasing serum glutamate-oxaloacetate transaminase (SGOT), decreasing serum Glutamic-Pyruvic Transaminase (SGPT), decreasing urine N-acetyl-beta-d-glucosaminidase (NAG), decreasing urine Albumin, decreasing plasma Ang II, decreasing tissue TGF-β1, lowering trigylcerides, lowering total cholesterol, increasing HDL cholesterol, lowering LDL cholesterol, lowering blood pressure, increasing nitric oxide level in tissue and plasma, increasing cGMP level in plasma, increasing eNOS level in tissue, increasing mRNA expression of NO synthase, increasing mCOX, and/or improvement in endothelial function.

Some embodiments provide a method of preparing a nitrate enriched extract of Amaranth. The method includes crushing fresh leaves and stem of Amaranth to obtain a first slurry. Then the first slurry is treated with pectinase to obtain a pectinase treated material. The pectinase treated material is heated to obtain a pectinase-deactivated material. The pectinase-deactivated material is extracted with water to obtain a supernatant and a residue. The supernatant is concentrated to obtain a concentrated water extract. The concentrated water extract is cooled at 10° C. for 48 hours then filtered to obtain crystals of oxalic acid and/or oxalate and a second supernatant. The second supernatant is cooled at 10° C. for 24 hours to obtain a third supernatant and a second oxalic acid and/or oxalate crystals. The third supernatant is filtered to obtain a filtrate. The filtrate is concentrated to obtain a concentrated filtrate. The concentrated filtrate is dried to obtain a powdered extract. The powdered extract is treated with hexane to obtain a residue. The residue of oxalic acid or oxalate free extract of Amaranth is dried after hexane extraction under vacuum to obtain nitrate enriched Amaranth extract. The nitrate enriched Amaranth extract is dissolved in a buffer having pH 5 to obtain a second slurry. The second slurry is treated with an enzyme mixture of protease and a cellulase at 50° C. The protease and the cellulase are deactivated by heating to 80° C. to obtain enzyme treated slurry. The enzyme treated slurry is passed through a carbon column and the filterate is collected. The filterate is centrifuged to obtain a supernatant and a residue. The supernatant is loaded on polyphenol resin column and eluted first with water followed by eluting with methanol to obtain a water eluate fraction and a methanol eluate fraction. The water fraction is concentrated and dried to obtain a powder of water extract of Amaranth enriched with nitrate.

A method of preparing a combination composition for oral administration having a composition a) having a nitrate enriched extract of Amaranth and a composition b) having a bio-enhanced turmeric formulation is provided. The composition a) is prepared by a method including: crushing fresh leaves and stem of Amaranth to obtain a first slurry. Then the first slurry is treated with pectinase to obtain a pectinase treated material. The pectinase treated material is heated to obtain a pectinase-deactivated material. The pectinase-deactivated material is extracted with water to obtain a supernatant and a residue. The supernatant is concentrated to obtain a concentrated water extract. The concentrated water extract is cooled at 10° C. for 48 hours then filtered to obtain crystals of oxalic acid and/or oxalate and a second supernatant. The second supernatant is cooled at 10° C. for 24 hours to obtain a third supernatant and a second oxalic acid and/or oxalate crystals. The third supernatant is filtered to obtain a filtrate. The filtrate is concentrated to obtain a concentrated filtrate. The concentrated filtrate is dried to obtain a powdered extract. The powdered extract is treated with hexane to obtain a residue. The residue of oxalic acid or oxalate free extract of Amaranth is dried after hexane extraction under vacuum to obtain nitrate enriched Amaranth extract. The nitrate enriched Amaranth extract is dissolved in a buffer having pH 5 to obtain a second slurry. The second slurry is treated with an enzyme mixture of protease and a cellulase at 50° C. The protease and the cellulase are deactivated by heating to 80° C. to obtain enzyme treated slurry. The enzyme treated slurry is passed through a carbon column and the filterate is collected. The filterate is centrifuged to obtain a supernatant and a residue. The supernatant is loaded on polyphenol resin column and eluted first with water followed by eluting with methanol to obtain a water eluate fraction and a methanol eluate fraction. The water fraction is concentrated and dried to obtain a powder of water extract of Amaranth enriched with nitrate. The composition b) is prepared by a method including suspending the curcuminoid mixture in water to form a suspension. Next, adding the essential oil of turmeric to the suspension to form a mixture. Followed by homogenizing the mixture to obtain a slurry. Then, drying the slurry under heat and vacuum to form a uniform blend of the composition having bio-enhanced turmeric formulation. Whereby the composition b) has a curcuminoid mixture and an essential oil of turmeric. The curcuminoid mixture includes curcumin, demethoxycurcumin and bisdemethoxycurcumin. The essential oil of curcumin includes about 45% ar-turmerone. A weight ratio of curcuminoid mixture to essential oil of curcumin ranges from about 1:1 to about 99:1. Blending the composition a) and the composition b) results in the combination composition.

A method of preparing a combination composition for oral administration having a composition a) having a nitrate enriched extract of Amaranth and a composition b) having an extract of seed of *Emblica officinalis* is provided. The composition a) is prepared by a method including: crushing fresh leaves and stem of Amaranth to obtain a first slurry. Then the first slurry is treated with pectinase to obtain a pectinase treated material. The pectinase treated material is heated to obtain a pectinase-deactivated material. The pectinase-deactivated material is extracted with water to obtain a supernatant and a residue. The supernatant is concentrated to obtain a concentrated water extract. The concentrated water extract is cooled at 10° C. for 48 hours then filtered to obtain crystals of oxalic acid and/or oxalate and a second supernatant. The second supernatant is cooled at 10° C. for 24 hours to obtain a third supernatant and a second oxalic acid and/or oxalate crystals. The third supernatant is filtered to obtain a filtrate. The filtrate is concentrated to obtain a concentrated filtrate. The concentrated filtrate is dried to obtain a powdered extract. The powdered extract is treated with hexane to obtain a residue. The residue of oxalic acid or oxalate free extract of Amaranth is dried after hexane extraction under vacuum to obtain nitrate enriched Amaranth extract. The nitrate enriched Amaranth extract is dissolved in a buffer having pH 5 to obtain a second slurry. The second slurry is treated with an enzyme mixture of protease and a cellulase at 50° C. The protease and the cellulase are deactivated by heating to 80° C. to obtain enzyme treated slurry. The enzyme treated slurry is passed through a carbon column and the filterate is collected. The filterate is centrifuged to obtain a supernatant and a residue. The supernatant is loaded on polyphenol resin column and eluted first with water followed by eluting with methanol to obtain a water eluate fraction and a methanol eluate fraction. The water fraction is concentrated and dried to obtain a powder of water extract of Amaranth enriched with nitrate. The composition b) is prepared by a method including deseeding fresh fruits of *Emblica officinalis* to obtain seeds of *Emblica officinalis*. Next, crushing the seeds of *Emblica officinalis* to obtain crushed seeds. Then extracting the crushed seeds with 95% methanol to obtain a residue and a supernatant. Next, concentrating the supernatant to obtain a concentrated methanol extract. Next, drying the concentrated methanol extract to obtain a powder of methanol extract of seeds of *Emblica officinalis*. Next, macerating the powder of methanol extract of seeds of *Emblica officinalis* in water to obtain a liquid. Then, extracting the liquid with ethyl acetate to obtain an ethyl acetate phase. Next, concentrating the ethyl acetate phase to obtain a concentrated ethyl acetate phase. Then, drying the concentrated ethyl acetate phase to obtain a powder of ethyl acetate extract of methanol extract of seed of *Emblica officinalis*. Blending the composition a) and the composition b) results in a combination composition having nitrate enriched extract of Amaranth and extract of seeds of *Emblica officinalis*.

BRIEF DESCRIPTION OF THE DRAWINGS

The above objectives and advantages of the disclosed teachings will become more apparent by describing in detail preferred embodiments thereof with reference to the attached drawings in which:

FIG. 10 b: Effect of post treatment of extract on tissue CKMB.

FIG. 10 c: Effect of post treatment of extract on plasma LDH.

FIG. 10 d: Effect of post treatment of extract on tissue LDH.

FIG. 10 e: Effect of post treatment of extract on plasma Troponin level.

FIG. 12 b: Effect of post treatment of extract on tissue IL-6 levels.

FIG. 12 c: Effect of post treatment of extract on plasma TNF levels.

FIG. 12 d: Effect of post treatment of extract on tissue TNF levels.

FIG. 13 b: Effect of post treatment of extract on tissue Nitrite levels.

FIG. 13 c: Effect of post treatment of extract on plasma MDA levels.

FIG. 13 d: Effect of post treatment of extract on tissue MDA levels.

FIG. 13 e: Effect of post treatment of extract on plasma SOD levels.

FIG. 13 f: Effect of post treatment of extract on tissue SOD levels.

FIG. 13 g: Effect of post treatment of extract on plasma GSH levels.

FIG. 13 h: Effect of post treatment of extract on tissue GSH levels.

DETAILED DESCRIPTION

Figure 1A:
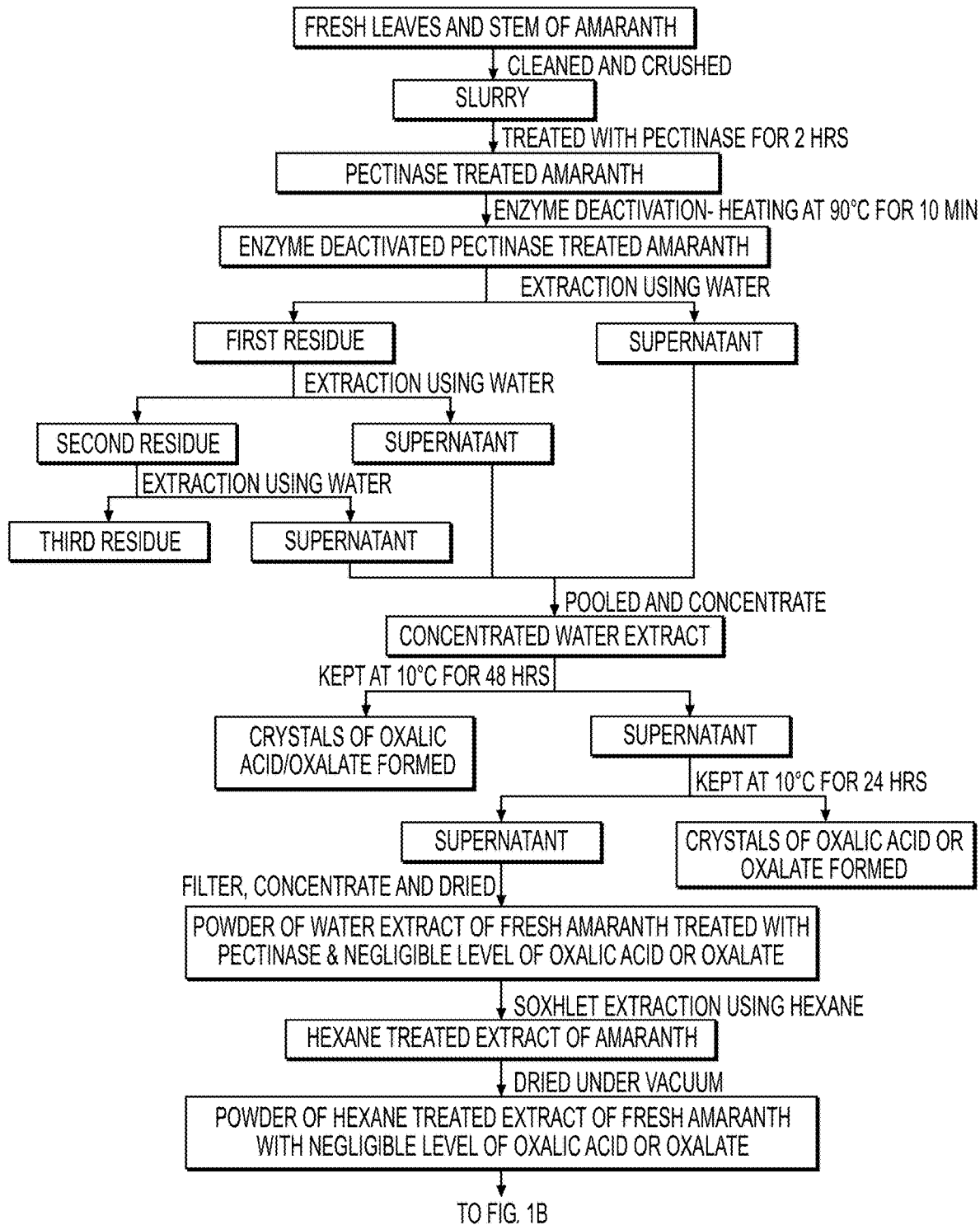
FIG. 1 (A and B): Method of preparation of extract of fresh Amaranth enriched with nitrate.

The disclosure provides a medicinal composition of Amaranth extract origin having enriched nitrate content, potassium and having negligible amount of oxalic acid or oxalate content for the prevention and treatment of myocardial ischemia-reperfusion injury.

The disclosure further provides a medicinal composition of Amaranth extract origin having enriched nitrate content, potassium and having negligible amount of oxalic acid or oxalate content and further added with a bio-enhanced turmeric formulation for the prevention and treatment of myocardial ischemia-reperfusion injury.

The disclosure also relates to a medicinal composition of Amaranth extract origin having enriched nitrate content added with amla seed extract for the prevention of myocardial ischemia-reperfusion injury.

The disclosure relates to a medicinal composition of Amaranth extract origin having enriched nitrate content, potassium and having a negligible amount of oxalic acid or oxalate content for the improvement of cardioprotective health and cardio renal protection.

The disclosure relates to a medicinal composition of Amaranth extract origin having enriched nitrate content added with bioenhanced turmeric formulation for the improvement of cardioprotective health and cardio renal protection.

The disclosure relates to a medicinal composition of Amaranth extract origin having enriched nitrate content added with Amla seed extract for the improvement of cardioprotective health and cardio renal protection.

A composition having a nitrate enriched extract of Amaranth for oral administration is disclosed. The nitrate enriched extract of Amaranth includes about 0.1% to about 70% nitrates; about 1% to about 40% potassium, and, about 0.1% total oxalic acid. In some embodiments, the composition of extract of Amaranth includes greater than about 20% to about 70% nitrates, about 1% to about 40% potassium, and, about 0.1% total oxalic acid. In some embodiments, the nitrate enriched extract of Amaranth includes about 9% nitrates, about 18% potassium, and, about 0.07% total oxalic acid. In some embodiments, the nitrate enriched extract of Amaranth includes about 18% nitrates, about 17% potassium, and, about 0.09% total oxalic acid. In some embodiments, the nitrate enriched extract of Amaranth includes about 70% nitrates, about 25% potassium, and, about 0.03% total oxalic acid. In some embodiments, the nitrate enriched extract of Amaranth is administered to a subject in need thereof at a dosage of about 100 mg to about 2000 mg. Some embodiments provide a dosage form of the composition of the nitrate enriched extract of Amaranth such as fast melt tablets, lozenge, candy, chewing gum, beverage, tablets, capsules, pills, or powders.

Some embodiments provide a method of preventing and treating myocardial ischemia-reperfusion injury by administering a composition having the nitrate enriched extract of Amaranth. Administering the composition results in a physiological parameter such as enhancing superoxide dismutase (SOD) activities, enhancing glutathione (GSH) activity, decreasing malondialdehyde (MDA) levels, lowering myocardial infarct size, lowering creatine kinase-MB (CK-MB), lowering lactate dehydrogenase (LDH) levels, decreasing the percentage of apoptosis, decreasing caspase-3 levels, increasing the level of cGMP, decreasing Troponin level, decreasing levels of IL-6 and TNF-α in plasma and tissue, decreasing NO levels, or decreasing myoglobin level. Some embodiments provide a method of improving cardioprotective health by administering a composition having the nitrate enriched extract of Amaranth. Administering the composition having the nitrate enriched extract of Amaranth results in a parameter such as decreasing mean blood pressure, decreasing triglycerides, decreasing total cholesterol, decreasing LDL cholesterol, decreasing VLDL cholesterol, increasing HDL, decreasing myocardial degeneration, decreasing necrosis, decreasing fibrosis, or decreasing intima media thickness. Some embodiments provide a method of providing cardio-renal protection by administering a composition having the nitrate enriched extract of Amaranth. Administering the composition having the nitrate enriched extract of Amaranth results in a parameter such as decreasing serum glutamate-oxaloacetate transaminase (SGOT), decreasing serum Glutamic-Pyruvic Transaminase (SGPT), decreasing urine N-acetyl-beta-d-glucosaminidase (NAG), decreasing urine Albumin, decreasing plasma Ang II, decreasing tissue TGF-β1, lowering trigylcerides, lowering total cholesterol, increasing HDL cholesterol, lowering LDL cholesterol, lowering blood pressure, increasing nitric oxide level in tissue and plasma, increasing cGMP level in plasma, increasing eNOS level in tissue, increasing mRNA expression of NO synthase, increasing mCOX, and/or improvement in endothelial function.

The composition obtained from the enriched extract of Amaranth alone or in combination with bio-enhanced turmeric formulation or with Amla seed extract is useful for the prevention and treatment of myocardial ischemia-reperfusion injury. The said composition is found to be useful for enhancing superoxide dismutase (SOD) activities, and glutathione (GSH) activity and subsequently decreased malondialdehyde (MDA) levels. In some embodiments, the composition lowers infarct size, creatine kinase-MB (CK-MB), Myoglobin level and lactate dehydrogenase (LDH) levels in coronary flow. Some embodiments of the composition decrease the percentage of apoptosis, caspase-3 levels, Troponin level, IL6, TNF-α. Some embodiments of the composition increase the level of cGMP.

The composition obtained from the enriched extract of Amaranth alone or in combination with bioenhanced turmeric formulation or with Amla seed extract is useful for improving cardio protective health. Composition is useful for reducing mean blood pressure, decreases total cholesterol, triglycerides, low density lipoprotein (LDL) and very low density lipoprotein (VLDL). Composition is effective for enhancing high density lipoprotein level (HDL). Composition is useful for reducing myocardial degeneration, necrosis, fibrosis and also reduces intima media thickening (IMT).

A combination composition for oral administration is disclosed. The combination composition has a) a nitrate enriched extract of Amaranth and a composition b) comprising a bio-enhanced turmeric formulation. The composition a) has about 0.1% to about 70% nitrates; about 1% to about 40% potassium, and, about 0.1% total oxalic acid. The composition b) has a curcuminoid mixture and an essential oil of turmeric. The curcuminoid mixture consists of curcumin, demethoxycurcumin and bisdemethoxycurcumin. The essential oil of curcumin has about 45% ar-turmerone, and weight ratio of curcuminoid mixture to essential oil of curcumin ranges from about 1:1 to about 99:1. The combination composition is administered either in a single dosage form having both the composition a) and the composition b). Or the combination composition is administered as two dosage forms separately: one of which is a dosage form having composition a) and a second dosage form which has composition b). In some embodiments of the combination composition, the composition of nitrate enriched extract of Amaranth includes greater than about 20% to about 70% nitrates, about 1% to about 40% potassium, and, about 0.1% total oxalic acid. In some embodiments of the combination composition, the nitrate enriched extract of Amaranth includes about 9% nitrates, about 18% potassium, and, about 0.07% total oxalic acid. In some embodiments of the combination composition, the nitrate enriched extract of Amaranth includes about 18% nitrates, about 17% potassium, and, about 0.09% total oxalic acid. In some embodiments of the combination composition, the nitrate enriched extract of Amaranth includes about 70% nitrates, about 25% potassium, and, about 0.03% total oxalic acid. In some embodiments of the combination composition, the nitrate enriched extract of Amaranth is administered to a subject in need thereof at a dosage of about 100 mg to about 2000 mg. Some embodiments of the combination composition provide a dosage form such as fast melt tablets, lozenge, candy, chewing gum, beverage, tablets, capsules, pills, or powders. Some embodiments provide a method of administering the combination composition. The method of administration can be 1) administering a single dosage form comprising a mixture of the composition a) and the composition b). Or the method of administration can be separately administering two dosage forms, wherein one dosage form includes the composition a) and a second dosage form includes the composition b), and wherein the dosage forms of the two methods of administration are selected from the group consisting of fast melt tablets, lozenge, candy, chewing gum, beverage, tablets, capsules, pills, and powder.

Some embodiments provide a method of preventing and treating myocardial ischemia-reperfusion injury by administering a combination composition having the nitrate enriched extract of Amaranth and the bio-enhanced turmeric formulation. Administering the combination composition results in a physiological parameter such as enhancing superoxide dismutase (SOD) activities, enhancing glutathione (GSH) activity, decreasing malondialdehyde (MDA) levels, lowering myocardial infarct size, lowering creatine kinase-MB (CK-MB), lowering lactate dehydrogenase (LDH) levels, decreasing the percentage of apoptosis, decreasing caspase-3 levels, increasing the level of cGMP, decreasing Troponin level, decreasing levels of IL-6 and TNF-α in plasma and tissue, decreasing NO levels, or decreasing myoglobin level. Some embodiments provide a method of improving cardioprotective health by administering the combination composition having the nitrate enriched extract of Amaranth and bio-enhanced turmeric formulation. Administering the combination composition having the nitrate enriched extract of Amaranth results in a parameter such as decreasing mean blood pressure, decreasing triglycerides, decreasing total cholesterol, decreasing LDL cholesterol, decreasing VLDL cholesterol, increasing HDL, decreasing myocardial degeneration, decreasing necrosis, decreasing fibrosis, or decreasing intima media thickness. Some embodiments provide a method of providing cardio-renal protection by administering a combination composition having the nitrate enriched extract of Amaranth and bio-enhanced turmeric formulation. Administering the combination composition having the nitrate enriched extract of Amaranth results in a parameter such as decreasing serum glutamate-oxaloacetate transaminase (SGOT), decreasing serum Glutamic-Pyruvic Transaminase (SGPT), decreasing urine N-acetyl-beta-d-glucosaminidase (NAG), decreasing urine Albumin, decreasing plasma Ang II, decreasing tissue TGF-β1, lowering trigylcerides, lowering total cholesterol, increasing HDL cholesterol, lowering LDL cholesterol, lowering blood pressure, increasing nitric oxide level in tissue and plasma, increasing cGMP level in plasma, increasing eNOS level in tissue, increasing mRNA expression of NO synthase, increasing mCOX, and/or improvement in endothelial function.

The composition obtained from the enriched extract of Amaranth alone or in combination with bioenhanced turmeric formulation or with Amla seed extract is useful for cardio-renal protection. Composition is found to be effective and favourable improvement is found in Serum glutamate-oxaloacetate transaminase (SGOT), Serum Glutamic-Pyruvic Transaminase (SGPT), Urine N-acetyl-beta-d-glucosaminidase (NAG), Urine Albumin. plasma Ang II, tissue TGF-β1. Lipid profile, Blood pressure, cGMP level in plasma, eNOS level in tissue, mRNA expression of NO synthase, COX and No level in tissue and plasma.

The disclosure provides an entirely different medicinal composition prepared from Amaranth as nitrate source by a unique method of extraction. The disclosed processes provide an extract of Amaranth enriched with nitrate, potassium and having negligible oxalic acid or oxalate content. The Amaranth extract can be obtained from both fresh and dry leaves and stem of Amaranth.

The disclosure provides extracts having enriched nitrate, potassium and having negligible oxalic acid or oxalate content wherein the extracts may be obtained from red Amaranth or Spleen amaranth or *Amaranthus dubius* or any related species of amaranth like *A. caudatus, A. cruentus, A. hypochondriacus, A. tricolor, A. blitum, A. viridus* etc.

Some embodiments provide a composition obtained from the extract of Amaranth from fresh leaves and stem of Amaranth comprising enriched nitrate content, potassium and having negligible amount of oxalic acid or oxalate content wherein nitrates are present in the extract up to 70%, potassium content from 5% to 40%.

Some embodiments provide an extract of Amaranth having low total oxalic acid content. The extract includes:
about 0.1% to about 70% nitrates:
about 5% to about 40% potassium; and,
about 0.01% to about 50% of total oxalic acid. The total oxalic acid includes free oxalic acid and oxalate salts in the extract.

In some embodiments of the extract, nitrates range from about 0.1% to about 3%. In some embodiments of the extract, nitrates range from about 1% to about 10%. In some embodiments of the extract, nitrates range from about 10% to about 20%. In some embodiments of the extract, nitrates range from about 3% to about 20%. In some embodiments of the extract, nitrates range from about 20-30%. In some embodiments of the extract, nitrates range from about 20-50%. In some embodiments of the extract, nitrates range from about 20-70%. In some embodiments of the extract, total oxalic acid ranges from about 0.01% to about 0.1%. Total oxalic acid content in the extracts was determined by HPLC method to measure both free oxalic acid and oxalates content in the extracts. In some embodiments of the extract, total oxalic acid ranges from about 0.01% to about 1%. In some embodiments of the extract, total oxalic acid ranges from about 0.1% to about 1%. In some embodiments of the extract, total oxalic acid ranges from about 1% to about 10%. In some embodiments of the extract, total oxalic acid ranges from about 1% to about 20%. In some embodiments of the extract, total oxalic acid ranges from about 1% to about 30%. In some embodiments of the extract, total oxalic acid ranges from about 1% to about 40%. In some embodiments of the extract, total oxalic acid ranges from about 1% to about 50%. In some embodiments of the extract, total oxalic acid ranges from about 10% to about 20%.

In some embodiments, the extract of *Emblica officinalis* has about 9% nitrate, 18% potassium and 0.07% oxalic acid.

Some embodiments provide a composition obtained from bioenhanced turmeric formulation. Bio-enhanced turmeric formulation containing curcuminoid mixture and added essential oil of turmeric. In some embodiments, the curcuminoid mixture includes curcumin, demethoxycurcumin and bisdemethoxycurcumin. Curcumin content in the formulation ranges from 67-72%, demethoxycurcumin ranges from 14-19%, bisdemethoxycurcumin ranges from 2-5%. In some embodiments, the essential oil of turmeric includes ar-turmerone. In some embodiments, the essential oil of turmeric in the formulation ranges 7-8%. In some embodiments, the essential oil of turmeric includes about 40-50% ar-turmerone. In some embodiments the bioenhanced turmeric formulation contain 69.5% Curcumin, 17% demethoxycurcumin and 4% bisdemethoxycurcumin, 7.5% essential oil of turmeric and 45% Ar-turmerone.

Some embodiments provide a composition obtained from Amla seed extract. Amla seed extract containing 6-50% triterpenoids, 2-20% hydroxycinnamic acid and 10-60% fatty acid.

In some embodiments amla seed extract contain 9.5% triterpenoids, 4.3% hydroxycinnamic acid and 41.8% fatty acids.

The disclosure describes delivery of the nitrate enriched formulations orally as fast melt tablets, lozenge, candy, chewing gum, beverage, etc. to make it convenient for absorption from the mouth and also in the form of tablets, capsules, pills, powders, etc. to be absorbed from the stomach. Some embodiments provide a dosage form having the Amaranth extract and bioenhanced turmeric formulation.

Some embodiments provide a dosage form having the Amaranth extract and Amla seed extract. The dosage form is selected from the group consisting of fast melt tablet, lozenge, candy, chewing gum, beverage, tablet, capsule, pill, and powder.

Dosage form of an extract of Amaranth is disclosed for administering in a dosage ranging from about 100 mg to about 2000 mg to a human subject.

Further a dosage form of an extract of seed of *Emblica officinalis* for administering in a dosage ranging from about 5 mg to about 500 mg to a human subject.

Further a dosage form of bioenhanced turmeric formulation for administering in a dosage ranging from about 100 mg to about 2000 mg to a human subject.

Myocardial infarction (MI) is one of the major leading cause of mortality worldwide. Modern pharmacological studies evidenced the protective effect of various herbal extracts in prevention of cardiovascular diseases. Therapeutic effect and putative molecular mechanisms of Amaranth extract enriched with nitrate alone or in combination with bio-enhanced turmeric formulation against myocardial via left anterior descending coronary artery (LAD) methods in rats is disclosed. To achieve this, Wistar rats are randomized into seven groups including vehicle control, sham control. LAD control (Ischemia of 45 min and 60 min of reperfusion), positive control (verapamil 10 mg/kg), low dose (45 mg/kg), high dose (45 mg/kg) and combination groups. All animals are pre-treated with formulation doses once daily for 30 days via oral route before induction of surgery. Following 2 hours of reperfusion, plasma samples are collected to determine CKMB, LDH and troponin. Also, plasma cGMP levels are determined at day 0 and day 31. Further, pro-inflammatory cytokines like IL-6, TNF-α and, oxidative stress parameters like MDA, nitrite, GSH and SOD are determined. Myocardial infarction is determined by TTC staining while apoptosis is estimated with TUNEL staining. MI induced by LAD increases the levels of LDH, CKMB, oxidative stress, cardiac inflammation and apoptosis. However, pre-treatment with nitrate enriched Amaranth extract shows decreased levels of LDH and CKMB, IL-6 and TNF-α. MDA, nitrite, infarct size and apoptosis while improved antioxidants GSH and SOD and cGMP levels. Furthermore, the cardio protective effect of nitrate enriched Amaranth extract is strengthened in the presence of bio-enhanced turmeric formulation. The results suggest that protective effect of herbal formulations combination is achieved through deceasing the oxidative stress and repressing the inflammatory and apoptosis cascade while maintaining vasodilatory action via cGMP-NO pathway.

In one embodiment as shown in Example 5 and, significant decrease in percentage infarct size was observed by pre treatment with Amaranth extract, particularly in the high dose group and combination group (Amaranth extract enriched with nitrate and bio-enhanced turmeric formulation). At the end of 1-hour reperfusion, myocardial infarct size is assessed by TTC staining to evaluate the cardio protective effect of test formulation on myocardial I/R injury (FIG. 3a to FIG. 3h). Myocardial infarct size is significantly increased in IR group compared with the control group. In contrast, this effect is considerably diminished by pre treatment with test formulation, especially in the high dose group and combination group.

Figure 4A:
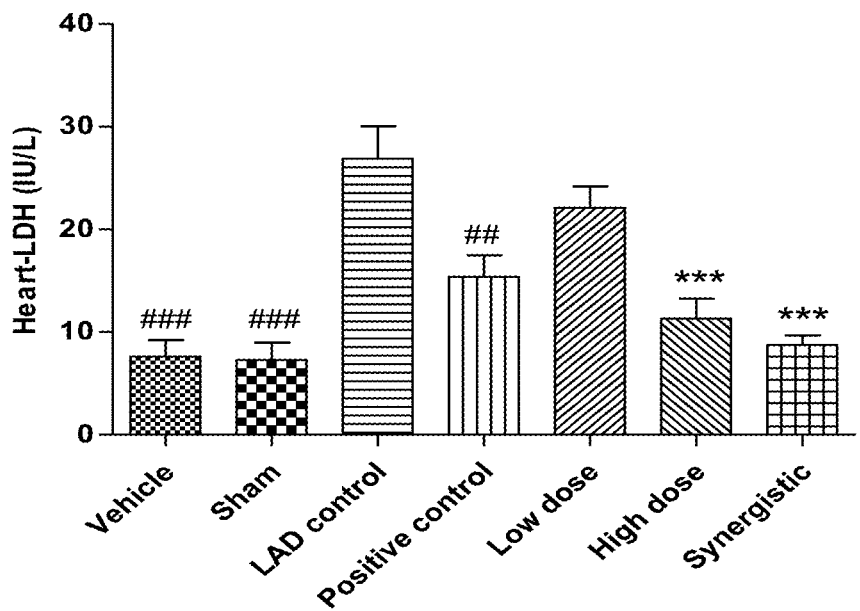
FIG. 4a: Effect of extract on LDH of heart homogenates.
Figure 4B:
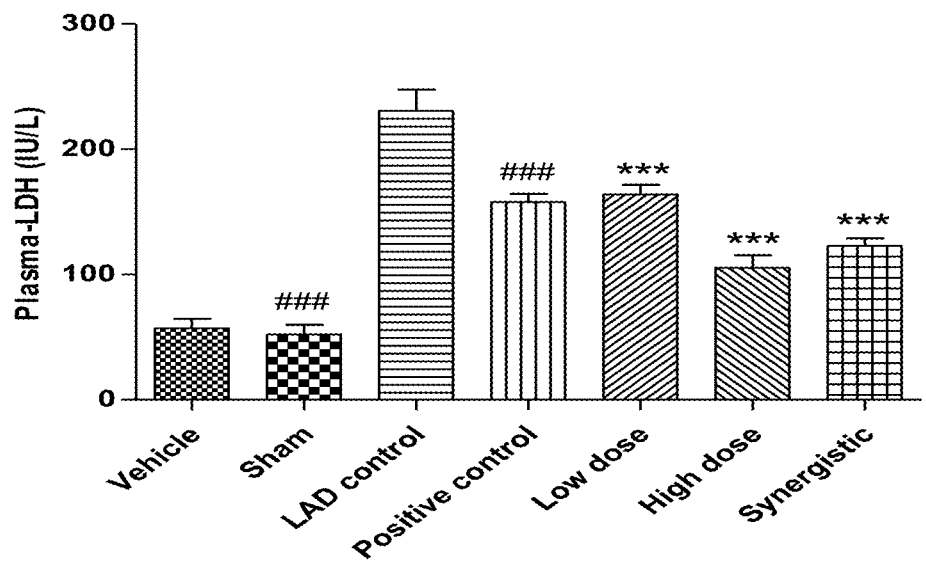
FIG. 4b: Effect of extract on plasma LDH.
Figure 4C:
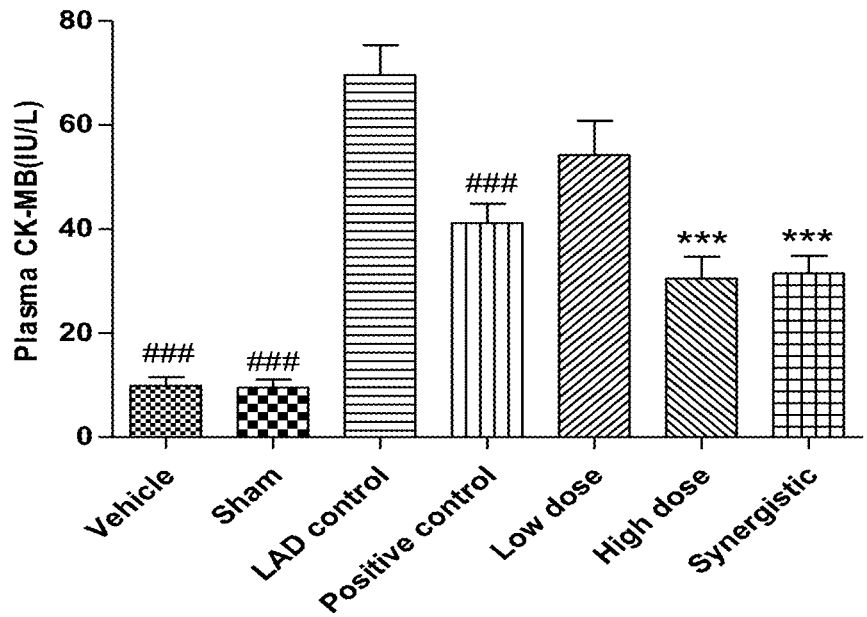
FIG. 4c: Effect of extract on plasma CKMB.
Figure 4D:
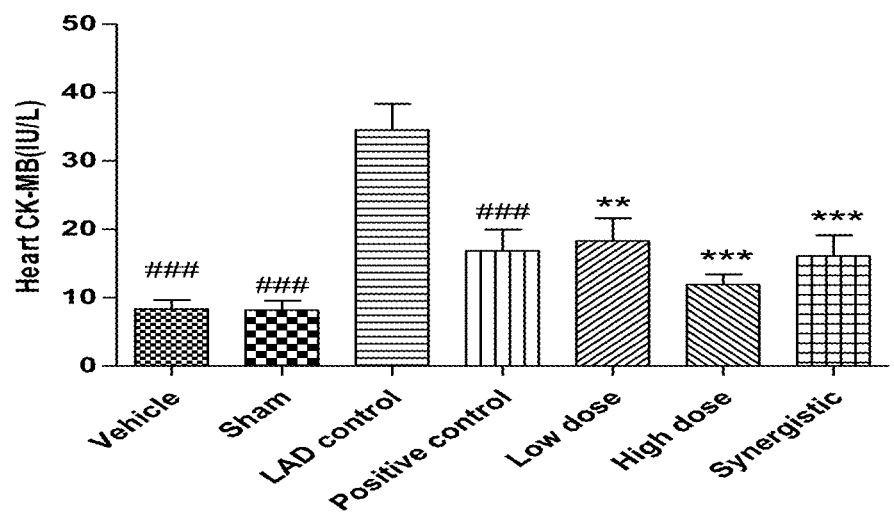
FIG. 4d: Effect of extract on heart CKMB.
Figure 4E:
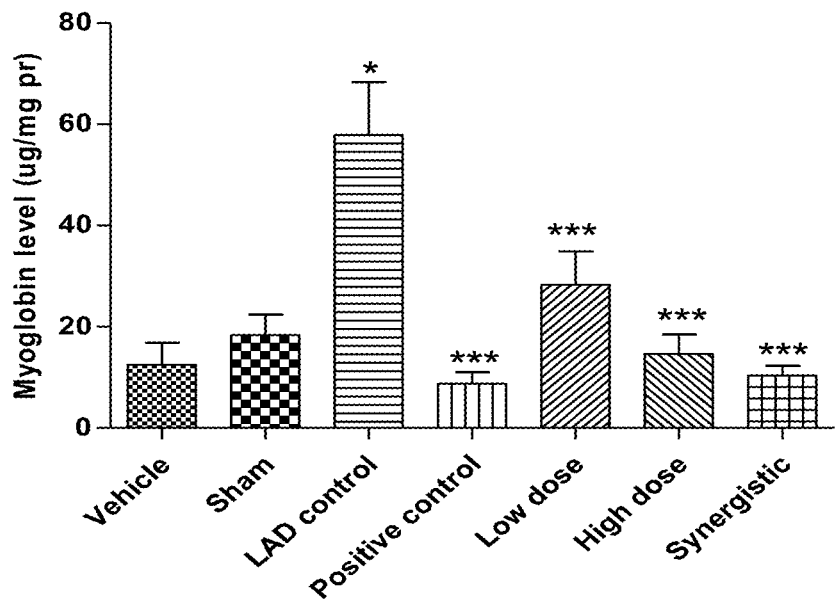
FIG. 4e: Effect of extract on Heart Myoglobin levels.
Figure 4F:
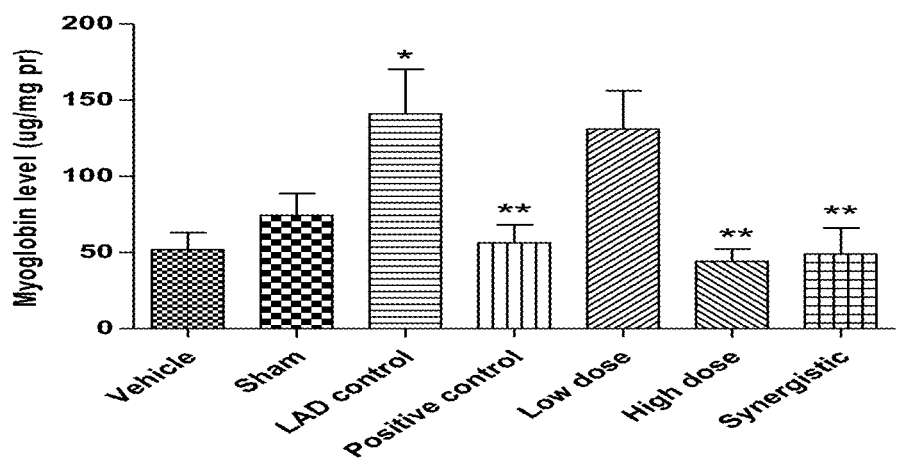
FIG. 4f: Effect of extract on Serum Myoglobin levels.
Figure 4G:
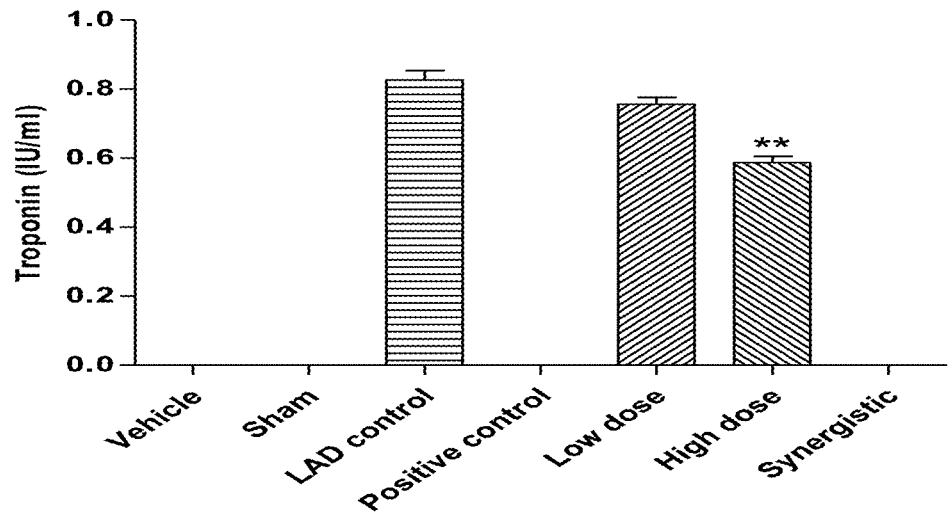
FIG. 4g: Effect of extract on plasmaTroponin level.

Levels of serum CK-MB and LDH are remarkably increased in rats of I/R group compared with control group. Pre-conditioning with test formulation at all tested dosages drop the level of LDH and CK-MB, but significantly attenuated the release at the dosage of 90 mg/kg in high dose and combination treatment group compared with the, I/R group. (FIG. 4a to FIG. 4f). No significant changes are observed in the Troponin I level in all the treatment groups (FIG. 4g).

Figure 5A:
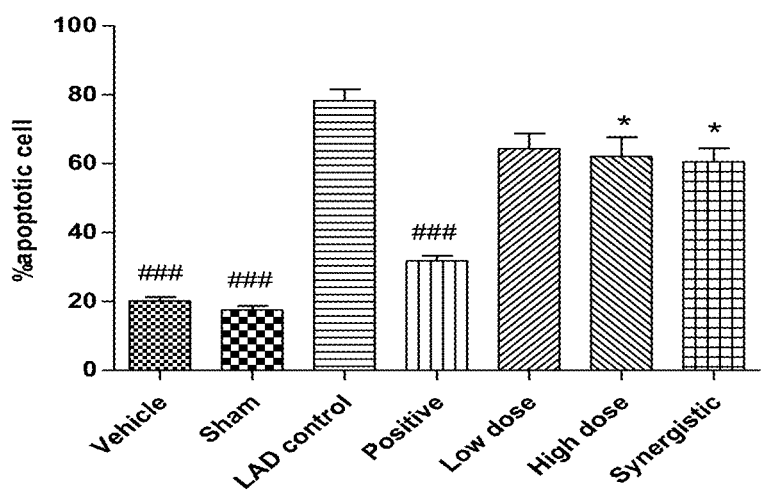
FIGS. 5a and 5c: Effect of extract on Myocardial apoptosis.
Figure 5B:
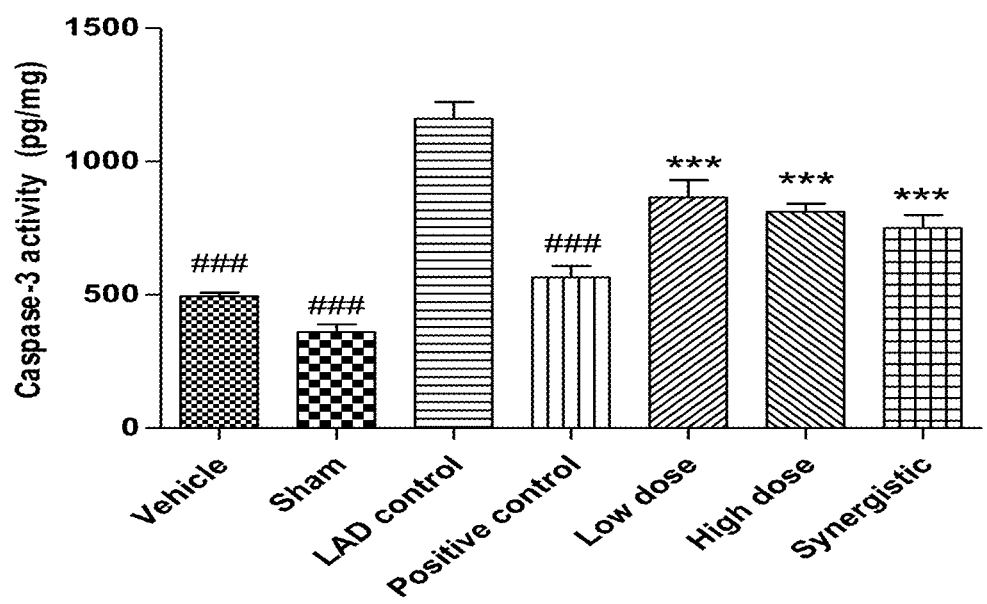
FIG. 5b: Effect of extract on caspase-3 levels.
Figure 5C:
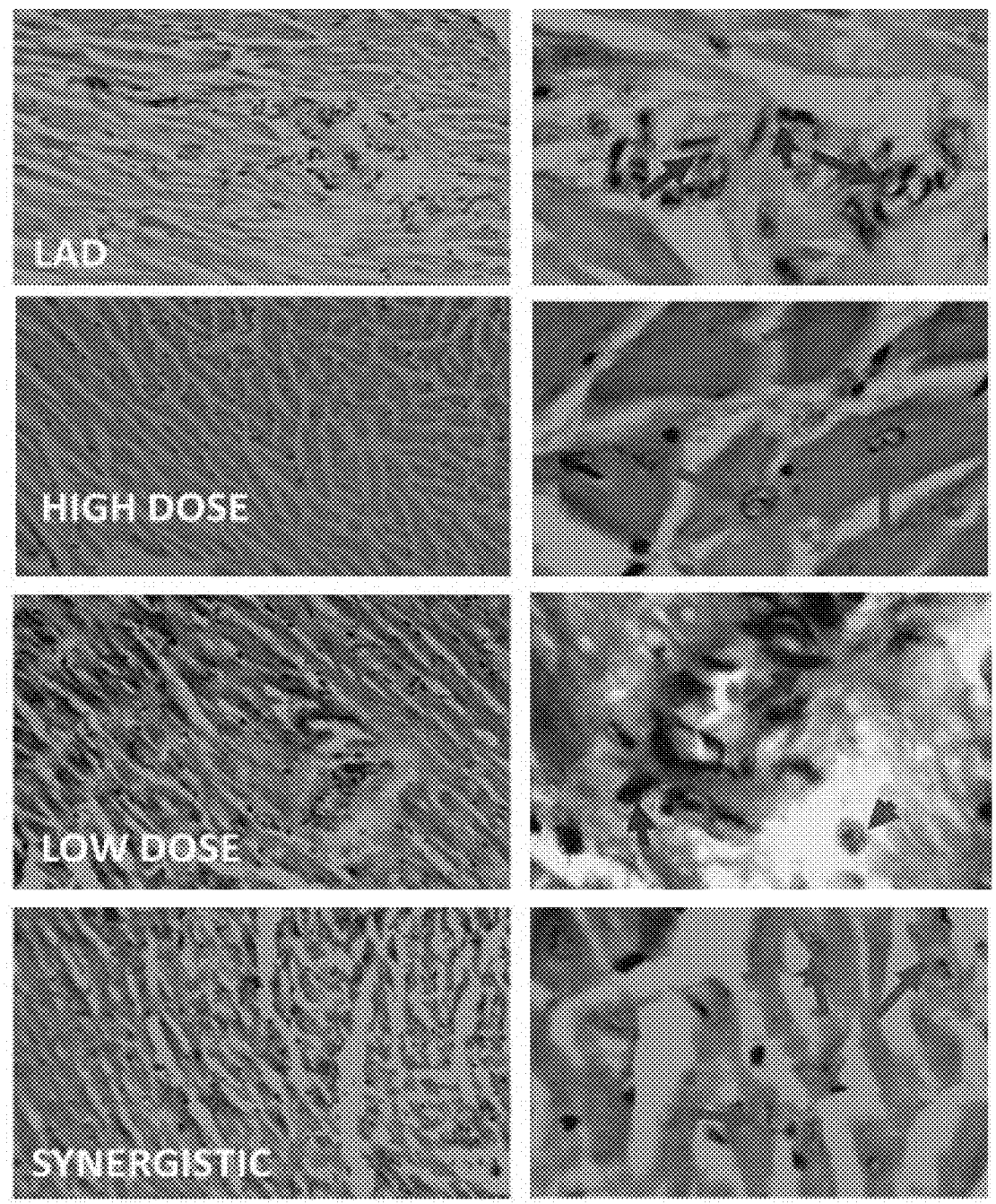
Figure 6A:
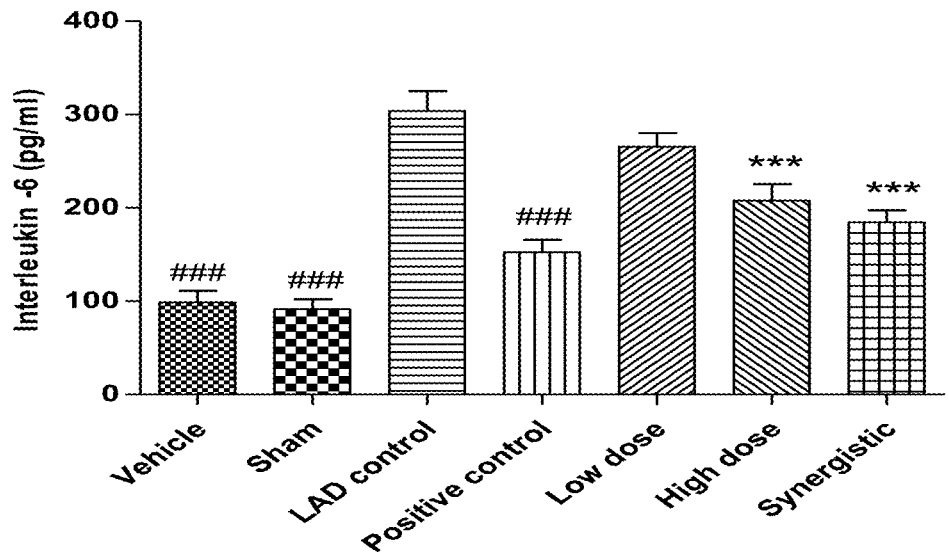
FIG. 6a Effect of extract on IL-6 levels.
Figure 6B:
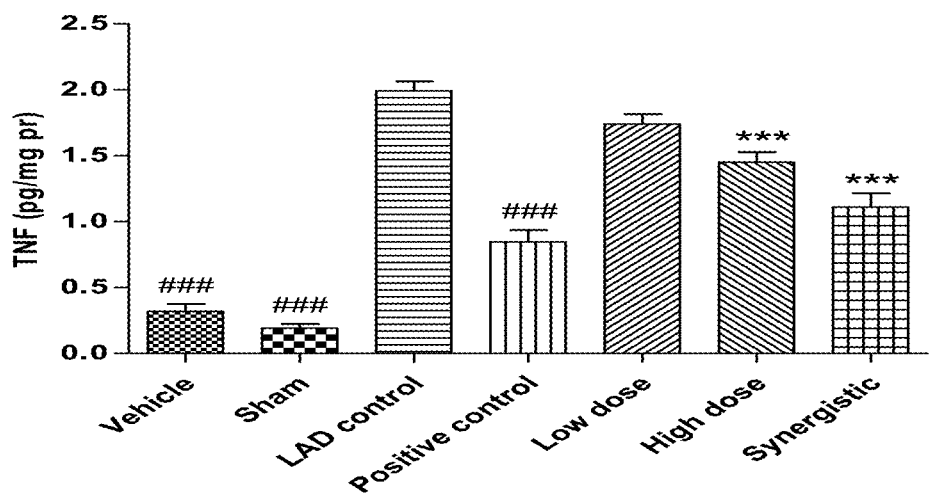
FIG. 6b: Effect of extract on TNF-α levels.
Figure 6C:
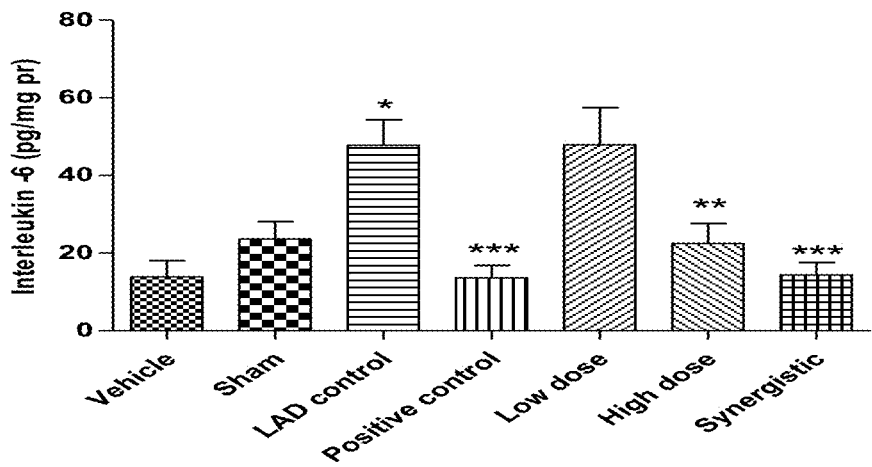
FIG. 6c: Effect of extract on IL-6 levels.
Figure 6D:
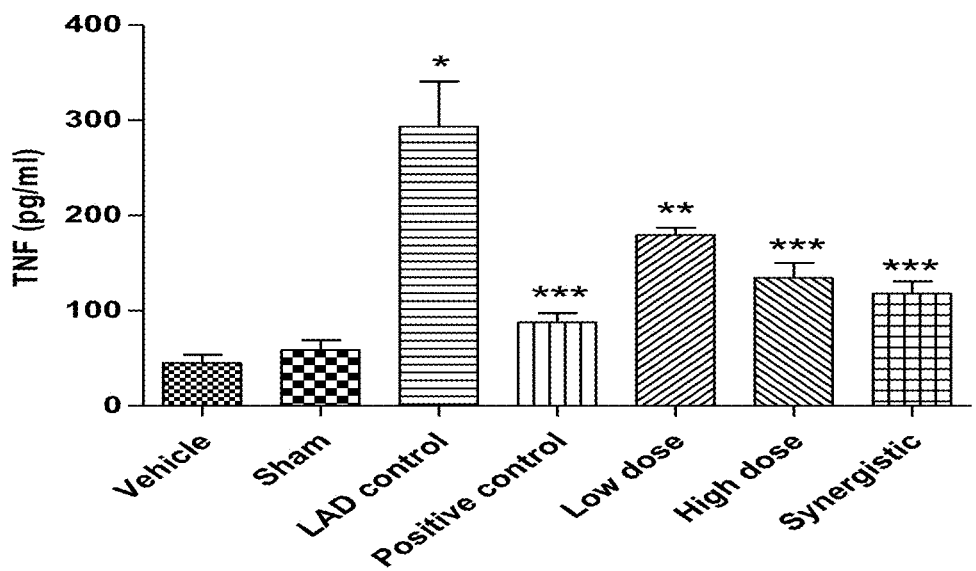
FIG. 6d: Effect of extract on TNF-α levels.
Figure 7A:
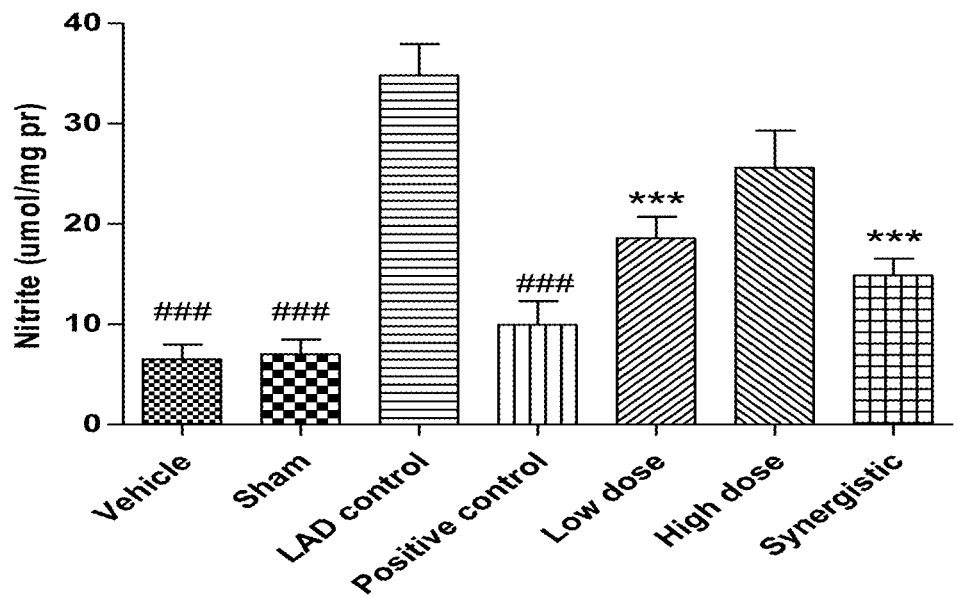
FIG. 7a: Effect of extract on Nitrite levels.
Figure 7B:
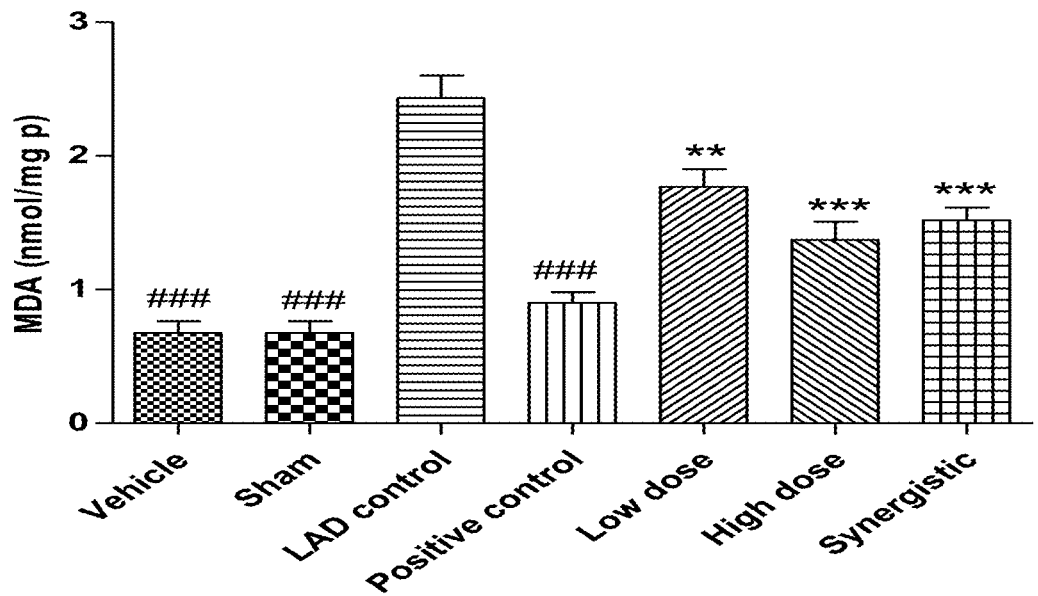
FIG. 7b: Effect of extract on MDA levels.
Figure 7C:
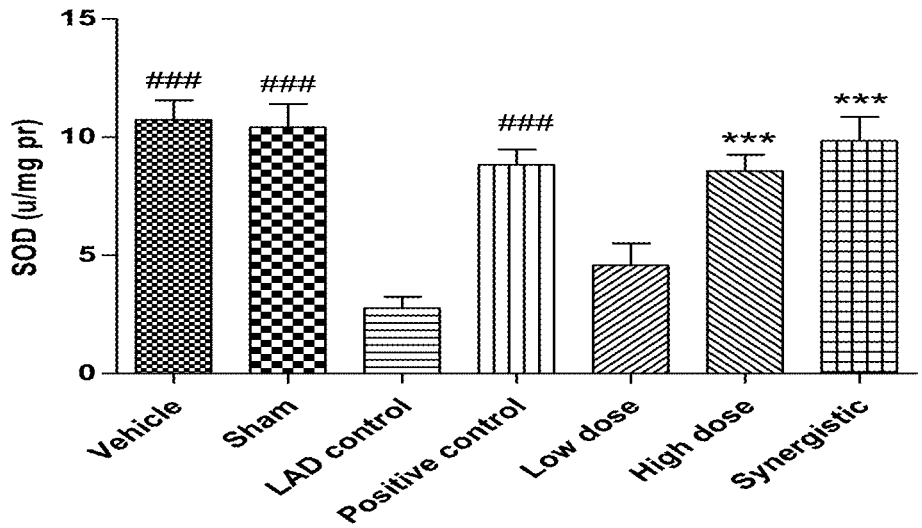
FIG. 7c: Effect of extract on SOD levels.
Figure 7D:
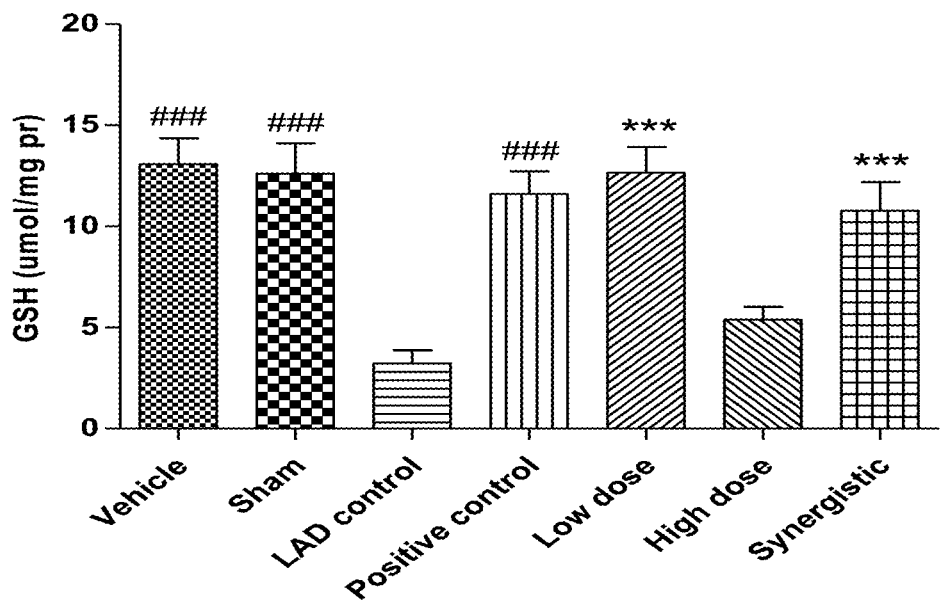
FIG. 7d: Effect of extract on GSH levels.

Ischemia and reperfusion induced myocardial injury significantly increased the percentage of apoptosis and it is significantly attenuated in treatment groups. The percentage of apoptotic cells is attenuated by pre-treatment with test formulation when compared to I/R group (FIG. 5a and FIG. 5c).

Levels of caspase-3 are remarkably increased in rats of I/R group compared with control group. Pretreatment with test formulation at dosage of 45 mg/kg, 90 mg/kg and combination group at dosage of 45+90 mg/kg significantly reduce the caspase-3 levels compared with the I/R group (FIG. 5b).

Change of IL-6 and TNF-α (in serum and heart homogenate) concentration of all the tested rats is given in FIG. 6.a-6.d. Plasma levels of IL-6 and TNF-α are significantly elevated following I/R injury compared with control group. Further, results showed that pretreatment with test formulation significantly attenuated the cytokines release. As expected, the treatment with test formulation dose-dependently protects the rats of I/R injury. In the combination group, the levels of inflammatory cytokines are mostly close to the positive control rats.

As illustrated in FIG. 7a-d, the result showed that the level of MDA and nitric oxide is significantly decreased and the activities of SOD and GSH are significantly increased in a dose-dependent manner by test formulation treatment when compared to I/R rats.

Figure 8A:
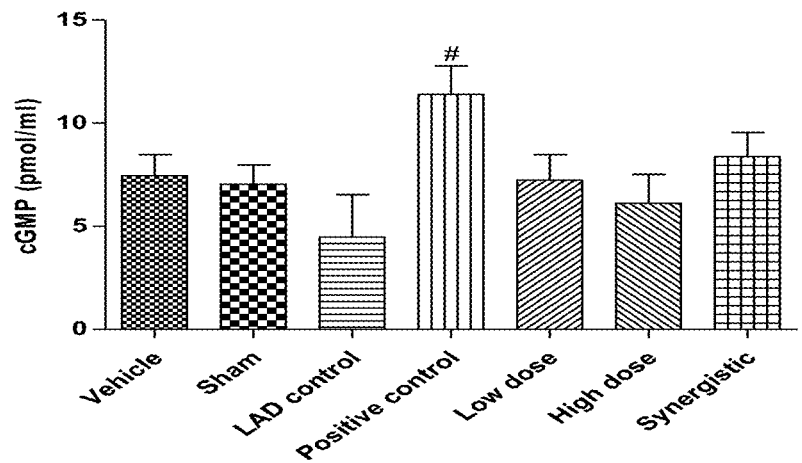
FIGS. 8a and 8b: Effect of extract on cGMP levels.
Figure 8B:
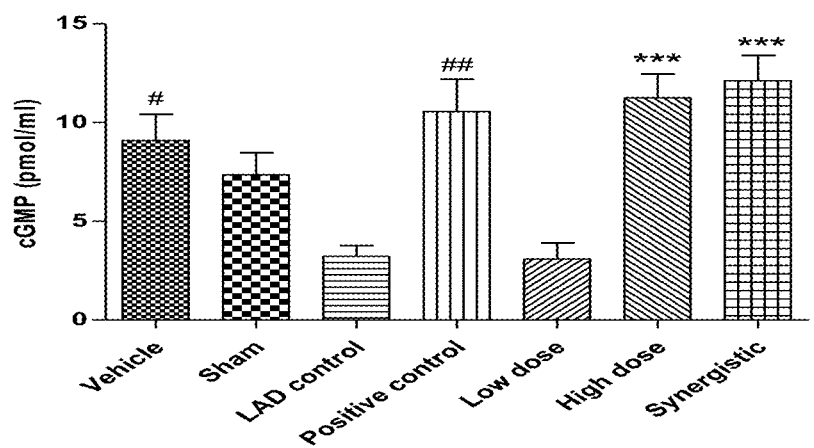
Figure 9A:
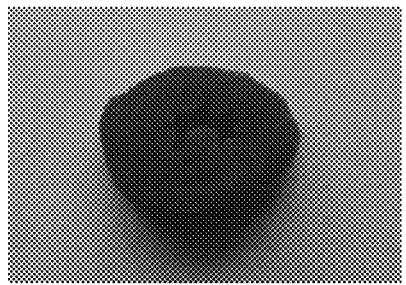
FIG. 9a: Effect of post treatment of extract on Infarct size of heart homogenates; Control Group (0 mg/kg).
Figure 9B:
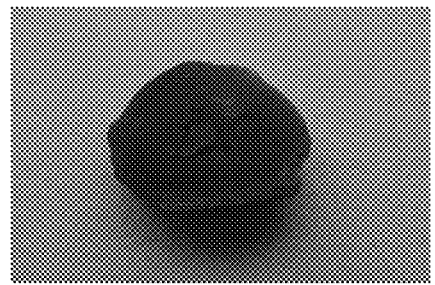
FIG. 9b: Effect of post treatment of extract on Infarct size of heart homogenates; Sham Group (0 mg/kg).
Figure 9C:
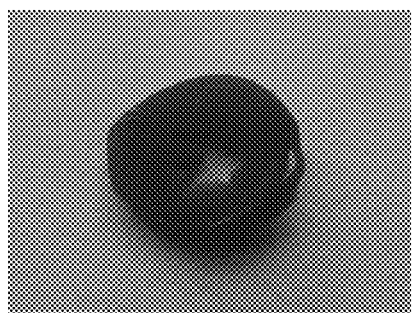
FIG. 9c: Effect of post treatment of extract on Infarct size of heart homogenates; Positive Control Group.
Figure 9D:
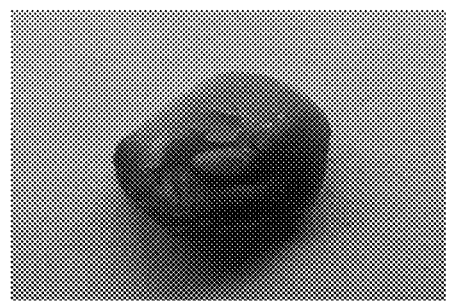
FIG. 9d: Effect of post treatment of extract on Infarct size of heart homogenates; LAD Control Group (I/R only).
Figure 9E:
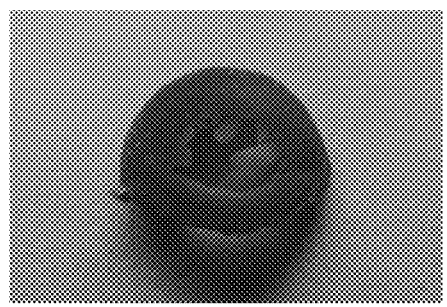
FIG. 9e: Effect of post treatment of extract on Infarct size of heart homogenates; Low dose Group (45 mg/kg).
Figure 9F:
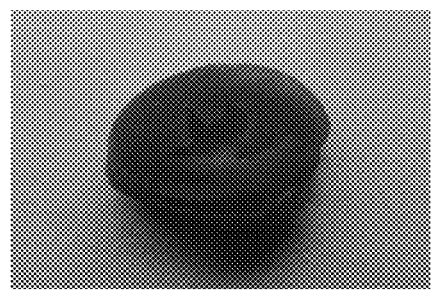
FIG. 9f: Effect of post treatment of extract on Infarct size of heart homogenates; High dose Group (90 mg/kg).
Figure 9G:
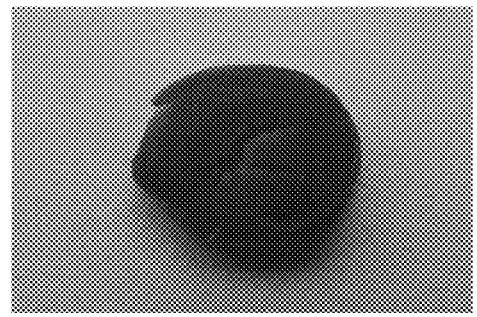
FIG. 9g: Effect of post treatment of extract on Infarct size of heart homogenates; Combination Group (90 mg/kg—Amaranth extract+90 mg/kg—bio enhanced formulation).
Figure 9H:
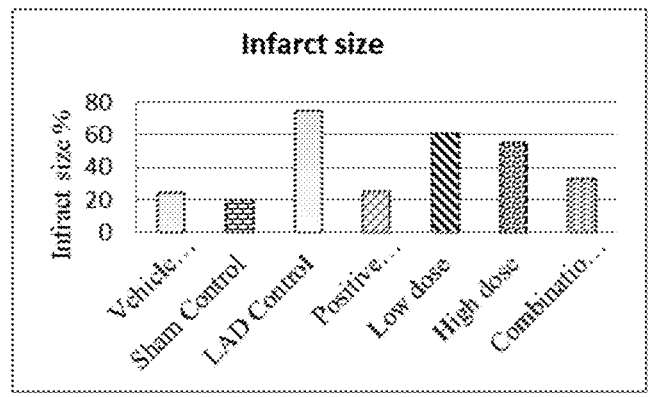
FIG. 9h: Effect of post treatment of extract on Infarct size of heart homogenates; Effect of post treatment of herbal extract on Infarct size of heart homogenates on $7^{th}$ day.
Figure 10A:
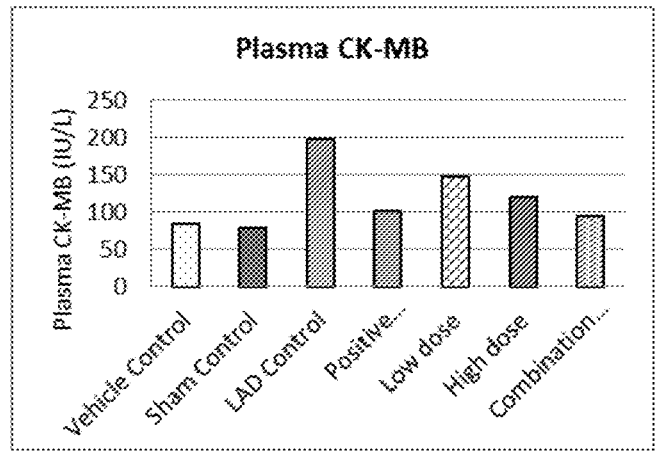
FIG. 10 a: Effect of post treatment of extract on plasma CKMB.
Figure 10B:
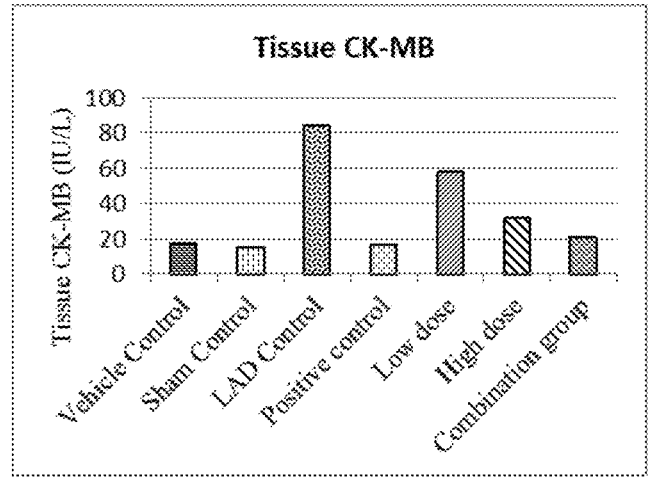
Figure 10C:
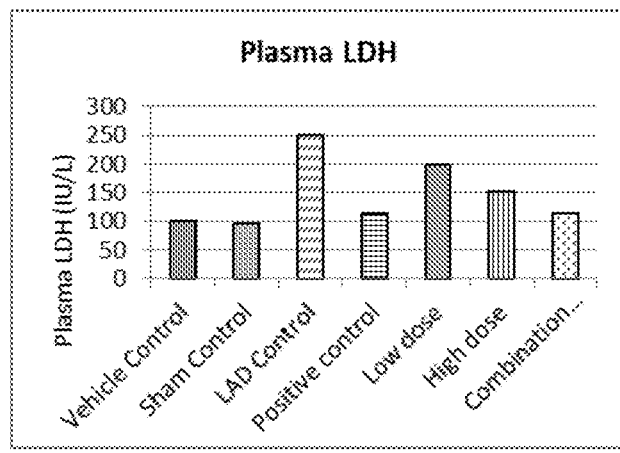
Figure 10D:
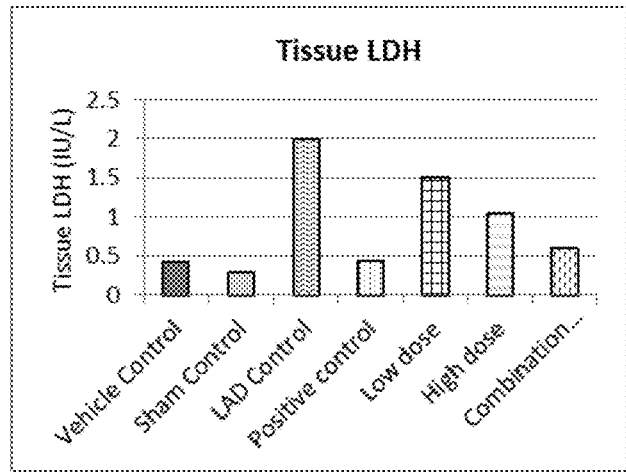
Figure 10E:
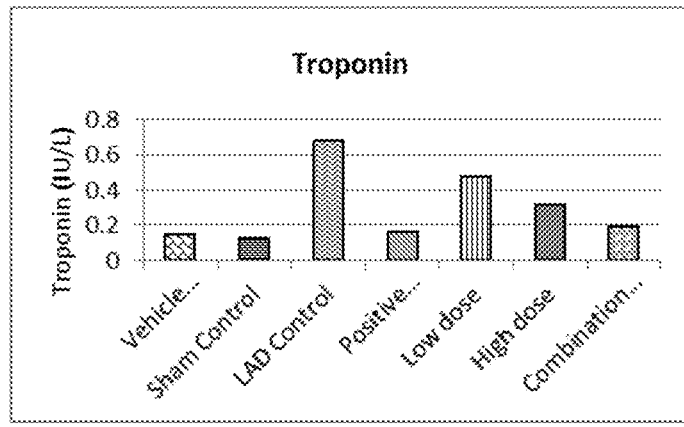
Figure 11A:
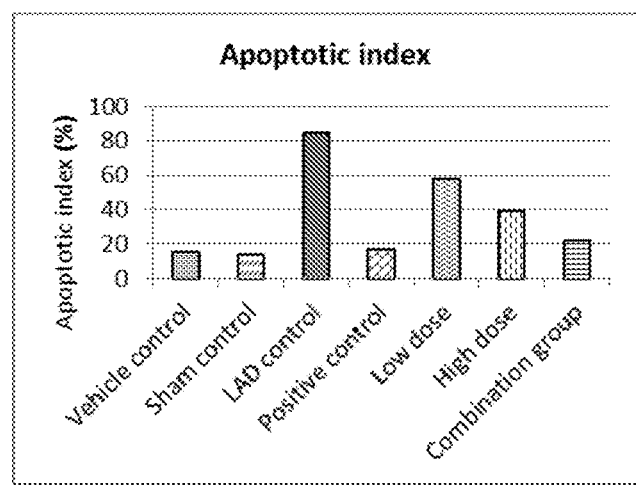
FIG. 11 a-h: Effect of post treatment of extract on Myocardial apoptosis.
Figure 11B:
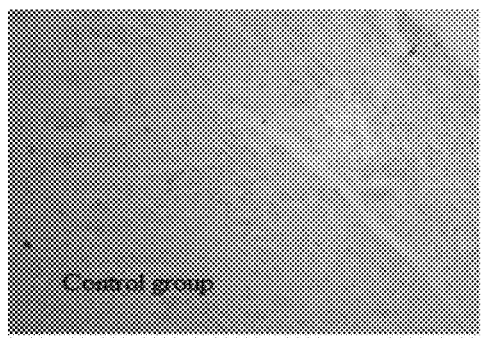
Figure 11C:
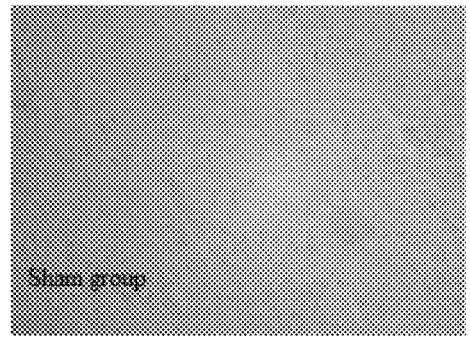
Figure 11D:
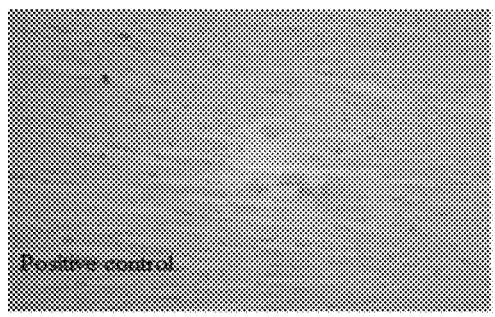
Figure 11E:
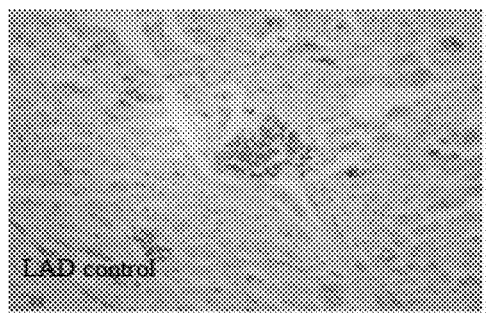
Figure 11F:
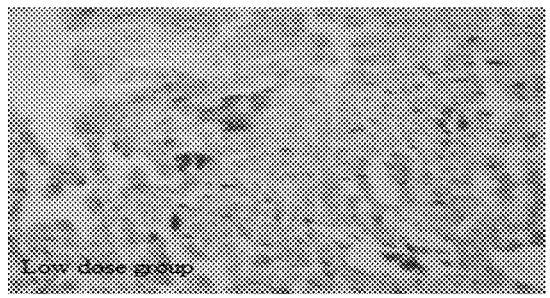
Figure 11G:
Figure 11H:
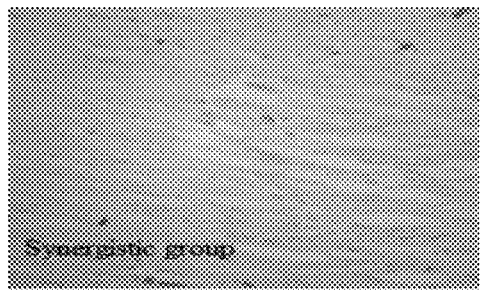
Figure 12A:
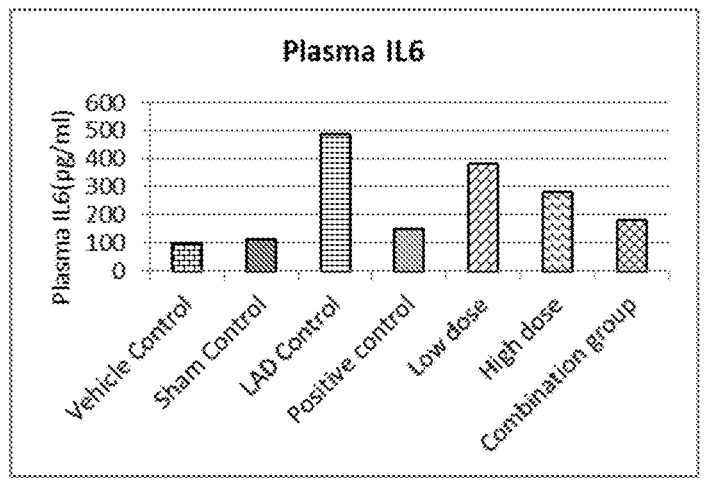
FIG. 12 a: Effect of post treatment of extract on plasma IL-6 levels.
Figure 12B:
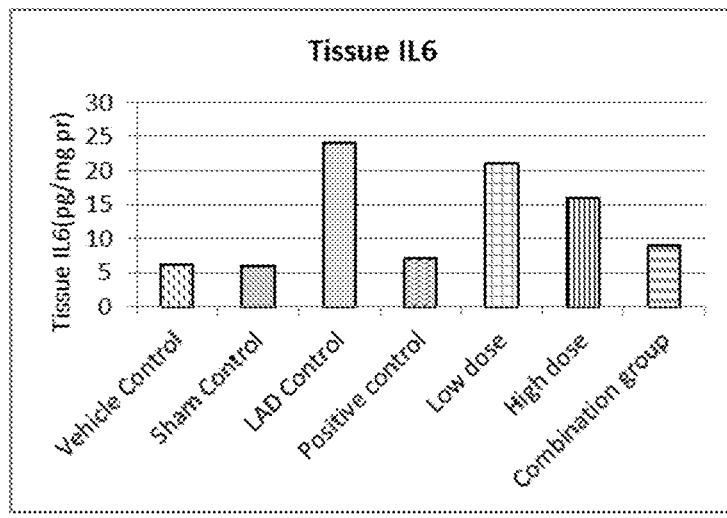
Figure 12C:
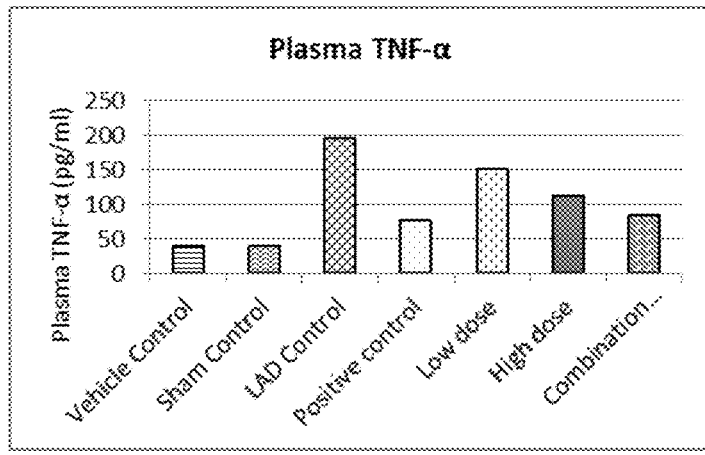
Figure 12D:
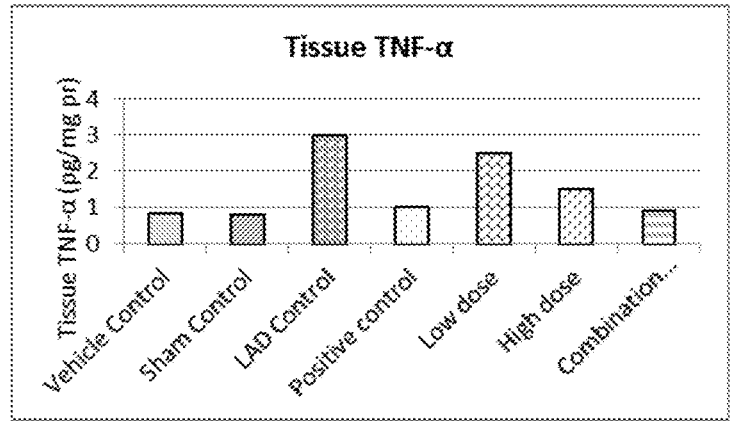
Figure 13A:
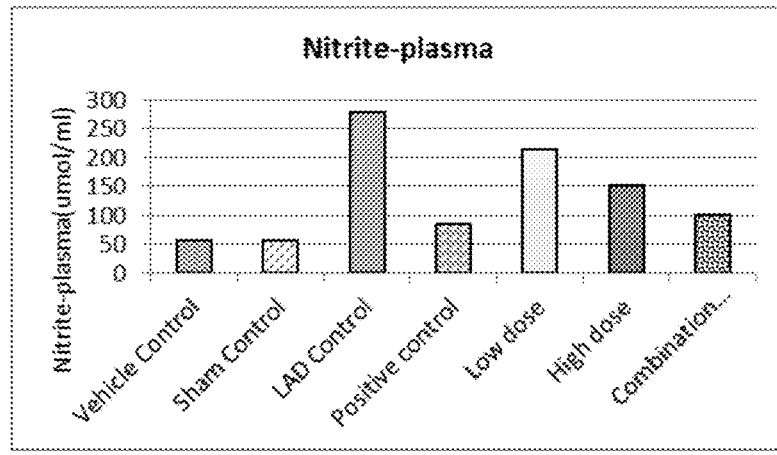
FIG. 13 a: Effect of post treatment of extract on plasma Nitrite levels.
Figure 13B:
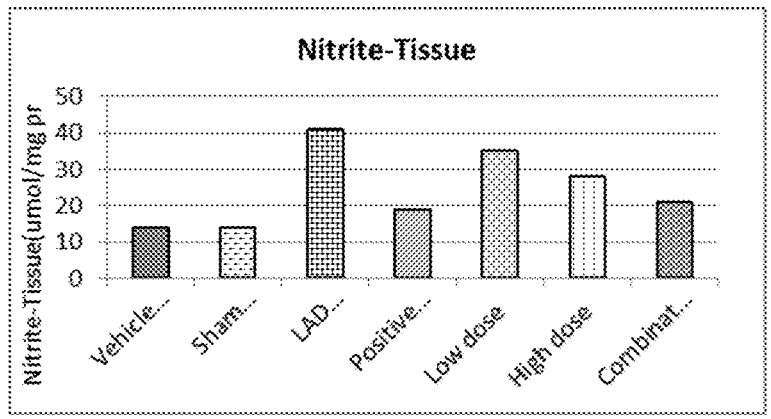
Figure 13C:
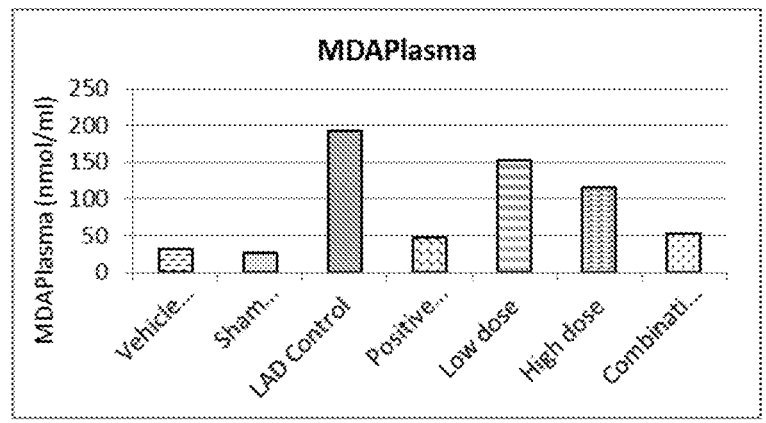
Figure 13D:
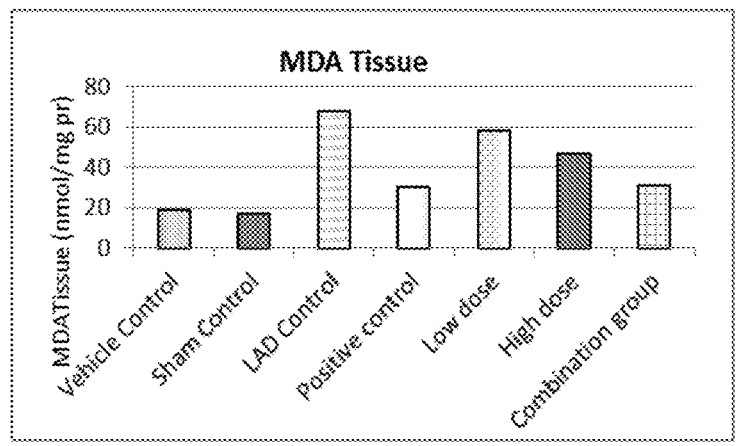
Figure 13E:
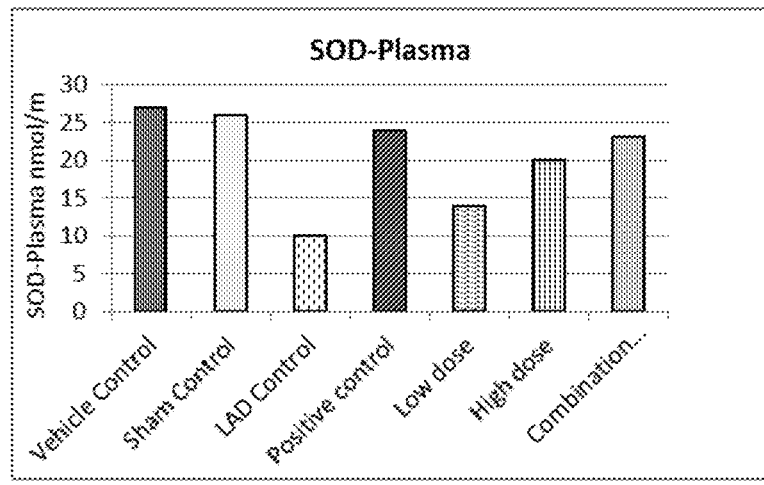
Figure 13F:
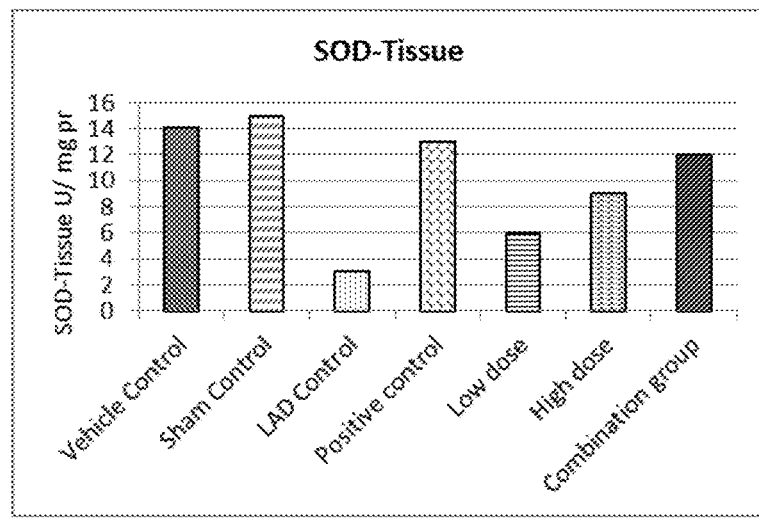
Figure 13G:
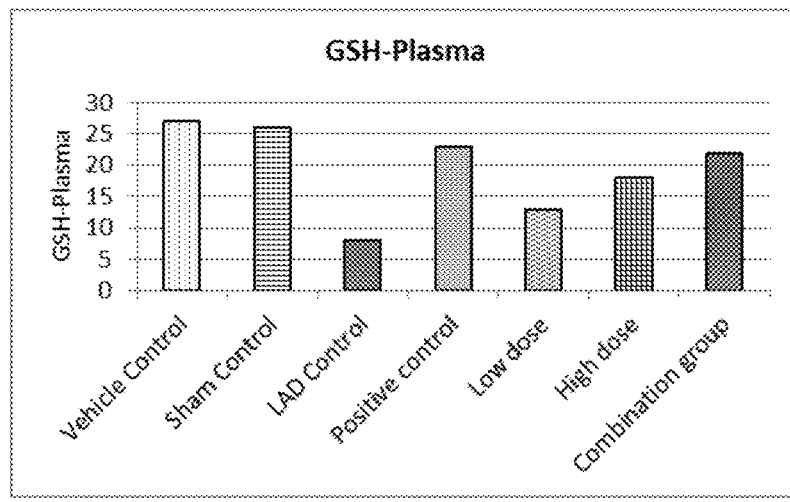
Figure 13H:
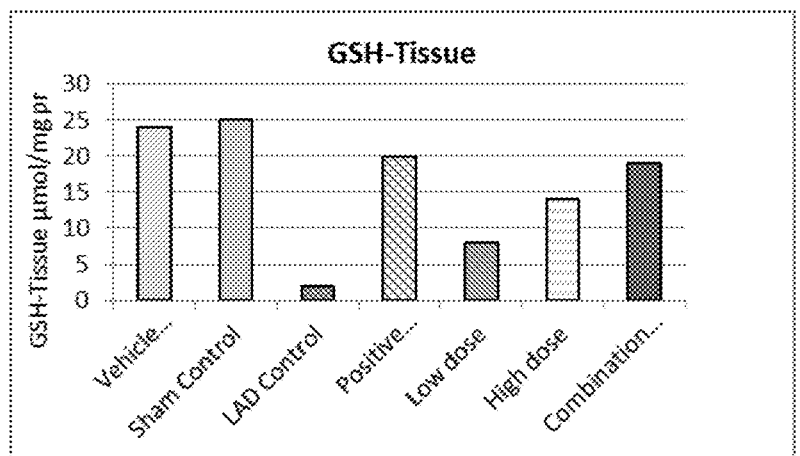

The level of cGMP is remarkably increased in rats of high dose group and combination group compared with the I/R group at day 31. At day 0, no significant difference is observed among different groups in the study (FIGS. 8a and 8b).

Post treatment activity potential of Amaranth extract enriched with nitrate alone or in combination with bio-enhanced turmeric formulation against myocardial ischemia reperfusion injury in rats through ligation of left anterior descending coronary artery (LAD) in rats is disclosed. Rats are divided into seven groups with eight animals in each group (4 males and 4 females). Each rat is individually placed in an induction chamber to provide anaesthesia using 5% isoflurane. The animals are then be subjected to artificial ventilation with an animal respirator venting 2% isoflurane in oxygen with a flow rate of 0.4 L/min. Further, a thoracotomy by an oblique incision is made that is approximately 1 cm long at a site 2 mm away from the left sternal border in the direction of where the left front leg meets the body (approximately 1-2 mm below where the leg and body join). The superficial thoracic vein is near this site, and the incision is made so that the lateral end of the incision goes up to, but does not cut into, the vein.

A cut through the thoracic muscle is done to expose the ribs underneath. The ribs and inflating lung through the thin and semi transparent chest wall is visualised. Chest cavity is opened using surgical scissors to make a 6-8 mm incision in the fifth intercostal space. This incision is a minimum of 2 mm from the sternal border where the internal thoracic artery is located. Pre-sterilized homemade chest retractors are inserted into the incision and gently pull back to open the incision so that it is about 8-10 mm wide while being careful to avoid the lung. The retractors are attached to the surgical platform with pins. At this point the heart is visible; however, the lung still covers a portion of the heart. The pericardium is picked up gently with curved forceps, pulled apart, and the tissue behind the retractors is slided. During this manipulation, the lung is lift up and appear away from the heart. Further positioning of LAD is performed.

Post-treatment with nitrate enriched Amaranth extract or in combination with bio-enhanced turmeric formulation against myocardial ischemia reperfusion injury shows clinically significant results.

Myocardial infarct size was significantly increased in I/R group compared with the control group. In contrast, this effect was considerably diminished by post treatment with test formulation (Amaranth extract), particularly at the dosage of 90 mg/kg in high dose group and 90+90 mg/kg in combination group (Amaranth extract in combination with bio-enhanced turmeric formulation). Positive control also showed significant decrease in percentage infarct size. (FIG. 9a-9h).

Cardiac injury biomarkers are measured in heart homogenates (LDH and CKMB) and in plasma (LDH, CKMB and troponin). As shown in FIG. 10.a-10e, levels of CK-MB and LDH level (in plasma and heart homogenate) and troponin level (plasma) are remarkably increased in rats of I/R group as compared with control group. Post-conditioning with test formulation at dosage of 90+90 mg/kg in the combination group significantly attenuated the level of LDH and CK-MB when compared with the LAD control in plasma samples. In tissue samples, high dose and combination groups significantly attenuated the levels of LDH and CKMB when compared to LAD control group.

No significant changes are observed in the troponin I level at dosage of 45 mg/kg in low dose w % bile high dose and combination treatment groups at 90 mg/kg and 90+90 mg/kg, respectively significantly attenuated the levels as compared to LAD control.

Myocardial apoptosis is determined by terminal deoxynucleotidyl transferase (TdT enzyme)-mediated dUTP nick end labeling (TUNEL) detection kit. As shown in FIG. 11a-11h, the I/R induced myocardial injury significantly increased the percentage of apoptosis and it is significantly attenuated by post-treatment with test formulation in high dose and combination group when compared with LAD control.

Levels of pro-inflammatory cytokines like IL-6. TNF-α in myocardial tissue homogenate and in plasma is detected using the kits from Wuhan fine biological tech Co ltd in strict accordance with manufacturer's instructions. FIG. 12a-12d shows the change of IL-6 and TNF-α (in serum and heart homogenate) concentration of all the tested rats. Plasma levels of IL-6 and TNF-α are significantly elevated following I/R injury compared with control group. Further, results determined that post-treatment with test formulation in the combination group significantly attenuated the pro-inflammatory cytokines release in the plasma and tissue samples when compared with LAD control group. However, a significant reduction of TNF-α is noticed in high dose group compared to L/R group in tissue samples and plasma samples.

Oxido-nitrosative stress is measured in terms of Superoxide production, Nitric oxide (Griess reagent assay), MDA level and activities of antioxidant SOD and GSH in heart homogenates. MDA level, nitrite levels, GSH and SOD are indicators of oxidative stress. As illustrated in FIG. 13a-13h, the results showed that I/R injury by LAD markedly increased the oxidative stress by elevating levels of MDA and nitrite and attenuating the levels of SOD and GSH. Further, the level of MDA and nitric oxide is significantly decreased by high dose and combination groups in plasma and tissue samples. The activities of SOD and GSH are significantly improved in all treated groups in plasma and tissue.

Figure 14:
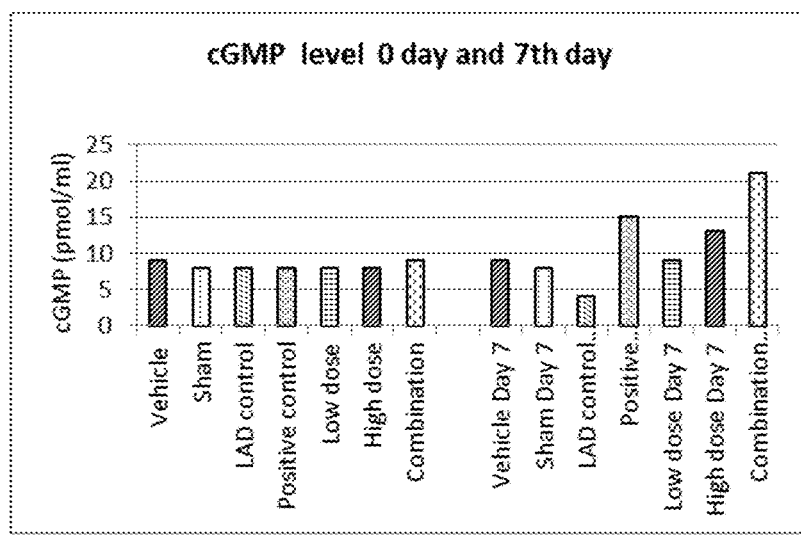
FIG. 14: Effect of post treatment of extract on cGMP levels on 0 and $7^{th}$ day.

Level of cGMP is increased in rats of high dose group and combination group on day 7 compared with the I/R group. Also, in low dose treated groups, elevation of cGMP is observed (FIG. 14).

A combination composition for oral administration having a) a nitrate enriched extract of Amaranth and b) an extract of seed of *Emblica officinalis* is disclosed. The nitrate enriched extract of Amaranth has about 0.1% to about 70% nitrates; about 1% to about 40% potassium, and, about 0.1% total oxalic acid. The extract of seed of *Emblica officinalis* has about 6% to about 50% of triterpenoids, about 2% to about 20% of hydroxycinnamic acids, about 10% to about 60% of fatty acids. The combination composition is administered either in a single dosage form having both the composition a) and the composition b). Or the combination composition is administered as two dosage forms separately: one of which is a dosage form having composition a) and a second dosage form which has composition b). In some embodiments of the combination composition, the composition of nitrate enriched extract of Amaranth includes greater than about 20% to about 70% nitrates, about 1% to about 40% potassium, and, about 0.1% total oxalic acid. In some embodiments of the combination composition, the nitrate enriched extract of Amaranth includes about 9% nitrates, about 18% potassium, and, about 0.07% total oxalic acid. In some embodiments of the combination composition, the nitrate enriched extract of Amaranth includes about 18% nitrates, about 17% potassium, and, about 0.09% total oxalic acid. In some embodiments of the combination composition, the nitrate enriched extract of Amaranth includes about 70% nitrates, about 25% potassium, and, about 0.03% total oxalic acid. In some embodiments of the combination composition, the nitrate enriched extract of Amaranth is administered to a subject in need thereof at a dosage of about 100 mg to about 2000 mg. Some embodiments of the combination composition provide a dosage form such as fast melt tablets, lozenge, candy, chewing gum, beverage, tablets, capsules, pills, or powders. Some embodiments provide a method of administering the combination composition. The method of administration can be 1) administering a single dosage form comprising a mixture of the composition a) and the composition b). Or the method of administration can be separately administering two dosage forms, wherein one dosage form includes the composition a) and a second dosage form includes the composition b), and wherein the dosage forms of the two methods of administration are selected from the group consisting of fast melt tablets, lozenge, candy, chewing gum, beverage, tablets, capsules, pills, and powder.

Some embodiments provide a method of preventing and treating myocardial ischemia-reperfusion injury by administering a combination composition having the nitrate enriched extract of Amaranth and the extract of seed of *Emblica officinalis*. Administering the combination composition results in a physiological parameter such as enhancing superoxide dismutase (SOD) activities, enhancing glutathione (GSH) activity, decreasing malondialdehyde (MDA) levels, lowering myocardial infarct size, lowering creatine kinase-MB (CK-MB), lowering lactate dehydrogenase (LDH) levels, decreasing the percentage of apoptosis, decreasing caspase-3 levels, increasing the level of cGMP, decreasing Troponin level, decreasing levels of IL-6 and TNF-α in plasma and tissue, decreasing NO levels, or decreasing myoglobin level. Some embodiments provide a method of improving cardioprotective health by administering the combination composition having the nitrate enriched extract of Amaranth and extract of seeds of *Emblica officinalis*. Administering the combination composition having the nitrate enriched extract of Amaranth results in a parameter such as decreasing mean blood pressure, decreasing triglycerides, decreasing total cholesterol, decreasing LDL cholesterol, decreasing VLDL cholesterol, increasing HDL, decreasing myocardial degeneration, decreasing necrosis, decreasing fibrosis, or decreasing intima media thickness. Some embodiments provide a method of providing cardio-renal protection by administering a combination composition having the nitrate enriched extract of Amaranth and extract of seeds of *Emblica officinalis*. Administering the combination composition having the nitrate enriched extract of Amaranth results in a parameter such as decreasing serum glutamate-oxaloacetate transaminase (SGOT), decreasing serum Glutamic-Pyruvic Transaminase (SGPT), decreasing urine N-acetyl-beta-d-glucosaminidase (NAG), decreasing urine Albumin, decreasing plasma Ang II, decreasing tissue TGF-β1, lowering trigylcerides, lowering total cholesterol, increasing HDL cholesterol, lowering LDL cholesterol, lowering blood pressure, increasing nitric oxide level in tissue and plasma, increasing cGMP level in plasma, increasing eNOS level in tissue, increasing mRNA expression of NO synthase, increasing mCOX, and/or improvement in endothelial function.

Cardio protective activity of Amaranth extract enriched with nitrate in combination with Amla seed extract is studied in rats. Oral administration of L-NAME is associated with a significant rise in mean arterial blood pressure (MAP) compared with the normotensive control rats, validating the induction of hypertension. Administration of Amaranth extract or Amla seed extract caused a significant decline of MAP in the hypertensive rats. After Amaranth extract administration, the percentage increase in MAP is 17% compared to baseline. That is, 4.8 fold less increase in MAP compared to untreated control. Amla seed extract administration showed 54% increase in MAP compared to baseline or 1.5 fold less increase in MAP compared to untreated control. A combination of Amaranth extract and Amla seed extract reduced the MAP to almost normal. Combination of Amaranth extract and Amla seed extract showed 41 fold less increase in MAP compared to untreated control. The outcome of this study supports a synergistic antihypertensive and absence of competing mechanistic actions between the Amaranth extract and Amla seed extract on arterial function activity.

Hypertension and hyperlipidemia are considered as two concomitant cardiovascular risk factors. The results of the study indicated dyslipidemia in L-NAME-hypertensive rats evidenced by elevated serum triglycerides and cholesterol and LDL coupled with decreased level of HDL compared to normal control group. Concomitant administration of Amaranth extract or Amla seed extract significantly modulated this dyslipidemic profile. A combination of Amaranth extract and Amla seed extract nearly normalized the concentration of triglycerides, total cholesterol, LDL, VLDL and HDL. The percentage decrease in total cholesterol and triglyceride was 97% and 95% respectively compared to untreated control. A combination of Amaranth extract and Amla seed extract showed 92% increase in HDL cholesterol compared to untreated control. Both LDL and VLDL were decreased by 96% compared with untreated control. According to the study, a combination of Amaranth extract and Amla seed extract may contribute to the significant hypolipidemic effect observed in the treated groups.

The histopathological lesion scoring of the heart of the different groups showed that heart of the normotensive group showed a normal histological finding of the myocardium. The L-NAME hypertensive group revealed severe myocardial degeneration, necrosis, and fibrosis with mononuclear cell infiltration. The combination treatment is very effective and this group showed a significant reduction in all myocardial lesions. In Masson's trichrome—(MT) stained sections, the heart of L-NAME hypertensive rats showed extensive collagen fiber deposition and increased myocardial fibrosis compared to the normal controls. Groups that received Amaranth extract, Amla seed extract or combination showed marked attenuation of myocardial fibrosis and combination group is most effective. Myocardial degeneration, necrosis, and fibrosis are reduced to normal in combination group and the percentage decrease compared with untreated control is 98%, 91% and 92% respectively.

The aorta of the control group showed normal histological feature of tunica intima, tunica media, and tunica adventitia. The L-NAME hypertensive group showed focal tunica intima thickening and a significant increase in the thickness comparing to the control group. Treatment with Amaranth extract. Amla seed extract or combination of both resulted in a significant reduction in the intima media thickness when compared with the hypertensive group. Combination group showed a percentage decrease of 125% compared with the hypertensive group. The combination group is most effective in reducing the medial thickening.

In some embodiment, nitrate enriched Amaranth extract alone or in combination with bio-enhanced turmeric formulation is used for cardio-renal protection. Study showed a significant effect on cardio renal protection by using nitrate enriched Amaranth extract alone or in combination with bio-enhanced turmeric formulation.

Wistar rats are randomly divided into six groups of eight rats each. The first group (Negative control) is received a solution of vehicle daily, while the second one (Control) receive L-NAME (40 mg/kg/day) plus the vehicle. The third group is treated every day with a combined solution of L-NAME (40 mg/kg/day) and Captopril (20 mg/kg/day) while the forth and fifth group, are received a combination of L-NAME (40 mg/kg/day) and Amaranth extract with 9% nitrate (45 mg/kg/day) and L-NAME (40 mg/kg/day) and Amaranth extract with 9% nitrate (90 mg/kg/day) respectively. The sixth group received a solution of L-NAME (40 mg/kg/day), Amaranth extract with 9% nitrate (90 mg/kg/day) and bioenhanced turmeric formulation (90 mg/kg/day). All the treatments are orally administered daily for 4 weeks. At the end of the treatment, blood pressure of all the animals are measured. BP is measured by both non invasive and invasive technique. For invasive technique, animals are anaesthetized by intraperitoneal administration of sodium thiopental (50 mg/kg).

Immediately after blood pressure measurement, blood samples are collected from the abdominal artery, and centrifuged at 3000 rpm for 15 minutes. The plasma obtained is kept at −20° C. for lipid assay. The heart and the thoracic aorta are collected, washed in saline, weighed and used for both histological analysis and determination of NO tissue content. Biochemical parameters like Serum glutamate-oxaloacetate transaminase (SGOT) and Serum Glutamic-Pyruvic Transaminase (SGPT) Activity Assay are performed to analyse the Liver function. Urinary protein excretion for Urine N-acetyl-beta-d-glucosaminidase (NAG) and Albumin are performed weekly to analyse the Renal function. Renal histological changes are examined at the end of the experiment. In addition to this, plasma lipid profile, plasma Ang II, tissue TGF-β1 are estimated using kits. Vasodilatory effect is analysed by measuring level of NO, cGMP and eNOS. mRNA expression of NO synthase and COX is measured.

The disclosure provides different extracts of Amaranth extracted by using solvents like water, methanol, ethanol, isopropanol, n-butanol, methyl acetate, ethyl acetate, propyl acetate, n-butyl acetate and combinations thereof.

A water soluble amaranth extract for use in the treatment of cardiovascular diseases by preventing myocardial ischemia-reperfusion injury. A preferred water soluble extract will have Nitrate in the range of 0.1% to 70%, Potassium in the range of 1% to 40% and oxalic acid less than 0.1%. In a more preferred embodiment the amaranth extract comprises 9% Nitrate, 18% potassium and oxalic acid less than 0.1%.

Low molecular weight alcohols that can be used in preparation of the extract include methanol, ethanol, isopropanol, n-butanol and combinations thereof. Esters that can be utilized for extract preparation include methyl acetate, ethyl acetate, propyl acetate, n-butyl acetate and combinations thereof. Alkanes that can be used for preparation of the extract include pentane, hexane, heptane, isooctane, and combinations thereof.

Various species of Amaranth from which extract can be prepared include, *Amaranthus acanthochiton, Amaranthus acutilobus, Amaranthus viridis, Amaranthus albus, Amaranthus arenicola, Amaranthus australis, Amaranthus bigelovii, Amaranthus blitoides, Amaranthus blitum, Amaranthus* brownie. *Amaranthus californicus, Amaranthus cannabinus, Amaranthus caudatus, Amaranthus chihuahuensis, Amaranthus chlorostachys, Amaranthus crassipes, Amaranthus cnspus, Amaranthus cruentus, Amaranthus deflexus, Amaranthus dubius, Amaranthus fimbriatus, Amaranthus flondanus, Amaranthus graecizans. Amaranthus greggii. Amaranthus hybridus, Amaranthus hypochondriacus, Amaranthus leucocarpus, Amaranthus lineatus, Amaranthus lividus, Amaranthus mantegazzianus, Amaranthus minimus, Amaranthus muricatus, Amaranthus obcordatus, Amaranthus oleraceous, Amaranthus palmeri, Amaranthus paniculus, Amaranthus polygonoides, Amaranthus powellii, Amaranthus pringlei, Amaranthus pumilus, Amaranthus quitensis, Amaranthus retroflexus*, etc.

In some embodiments, the extract of Amaranth includes the second extract. The second extract is selected from the group consisting of amla extract, turmeric extract, grape seed extract, green tea extract, pomegranate extract, cocoa extract, coconut root extract, rosemary extract, mint leaf extract, star anise, sweet basil extract, cinnamon extract/clove extract, ginger extract, cumin seed extract, black pepper extract, fenugreek extract, or combinations thereof.

In some embodiments of the extract of Amaranth, the Amaranth is selected from the group consisting of *Amaranthus caudatus, Amaranthus cruentus, Amaranthus tricolor, Amaranthus blitum. Amaranthus viridis, Amaranthus dubis* or combinations thereof.

Figure 1B:
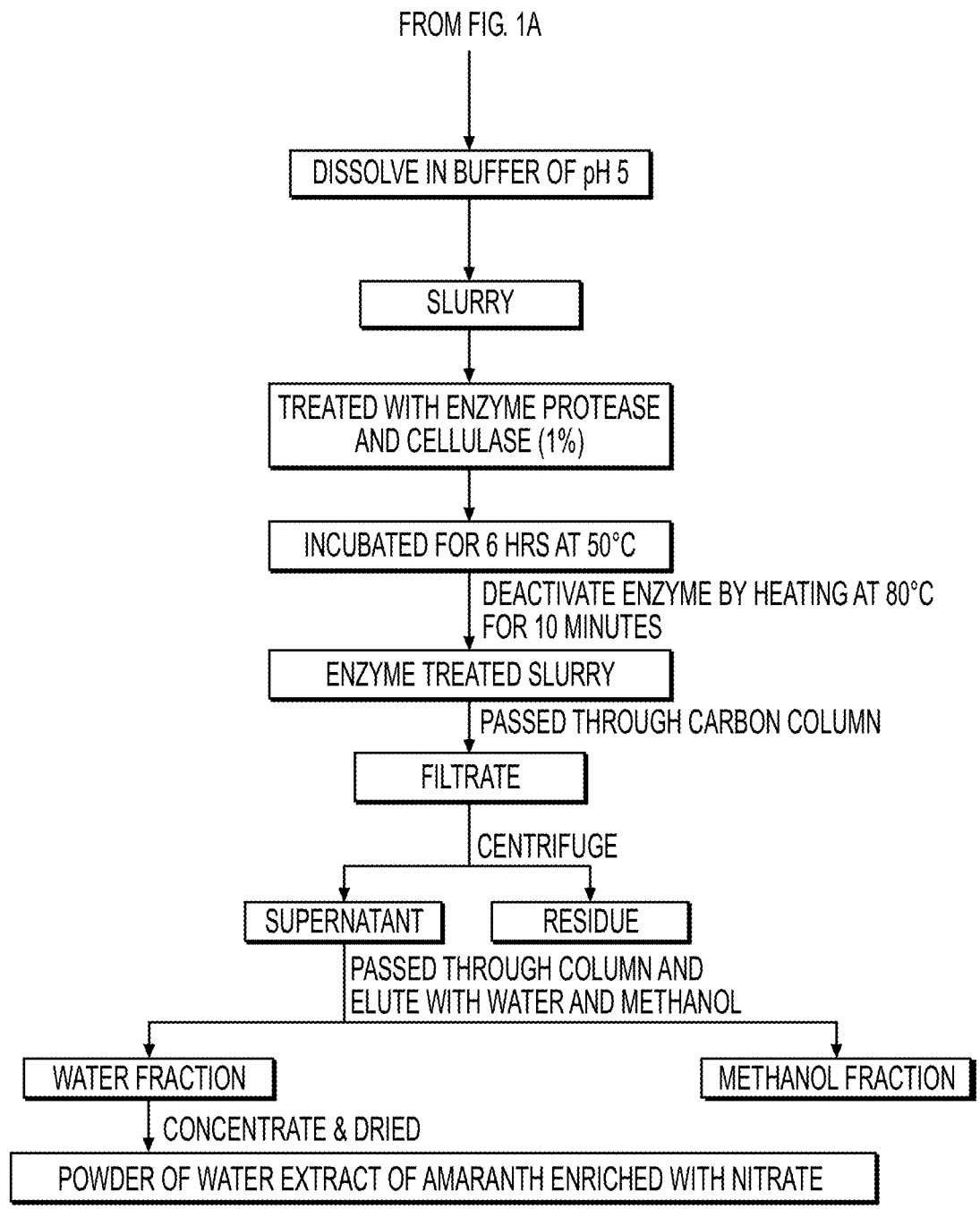

Various methods for the preparation of the extract enriched with nitrate content, potassium and having negligible oxalic acid or oxalate content prepared by the extraction of fresh leaves of Amaranth are as under:

In one embodiment, (refer to FIG. 1), the fresh leaves and stem of Amaranth are cleaned and crushed to form slurry. The slurry is a treated with pectinase (1%) for 2 hrs. Then the enzyme is deactivated by heating the slurry at 90° C. for 10 minutes. The pectinase treated Amaranth slurry is extracted for about 1 hr using water in an extractor with reflux condenser to obtain residue and supernatant. The residue and supernatant are separated by draining out the supernatant from the extractor bottom through the filter cloth. The resultant supernatant is concentrated in an Agitated thin film evaporator (ATFE) at a temperature of 85° C. to form concentrated extract. Keep the concentrated water extract at 10° C. for 48 hr to crystallize oxalic acid or oxalates. Decant the supernatant and again keep the supernatant at 10° C. for another 24 hr to crystallize remaining oxalic acid or oxalates. Decant and filter the supernatant and dry under vacuum at above 500 mm of mercury to get oxalic acid or oxalate free extract of Amaranth. A dried powder of oxalic acid or oxalate free extract of Amaranth is obtained after treating with pectinase is further extracted with hexane for 6 hours in a soxhlet extractor. Powder of oxalic acid or oxalate free extract of Amaranth after hexane extraction is dried under vacuum to get powder of hexane treated fresh Amaranth after treating with pectinase and removal of oxalic acid and having enriched nitrate content.

Nitrate enriched Amaranth extract is dissolved in a buffer of pH 5 to form a slurry. The slurry is treated with enzyme protease and cellulase (1%) and incubated for 6 hrs at 50° C. The enzyme is deactivated by heating the slurry at 80° C. for 10 minutes. Protease and cellulase treated slurry is passed through carbon column to obtain a filtrate. The filtrate obtained is loaded on a polyphenol resin column and eluted with water followed by methanol. Water fraction is concentrated and dried under vacuum at above 500 mm of mercury to get powder of water extract of Amaranth enriched with nitrate.

Figure 2:
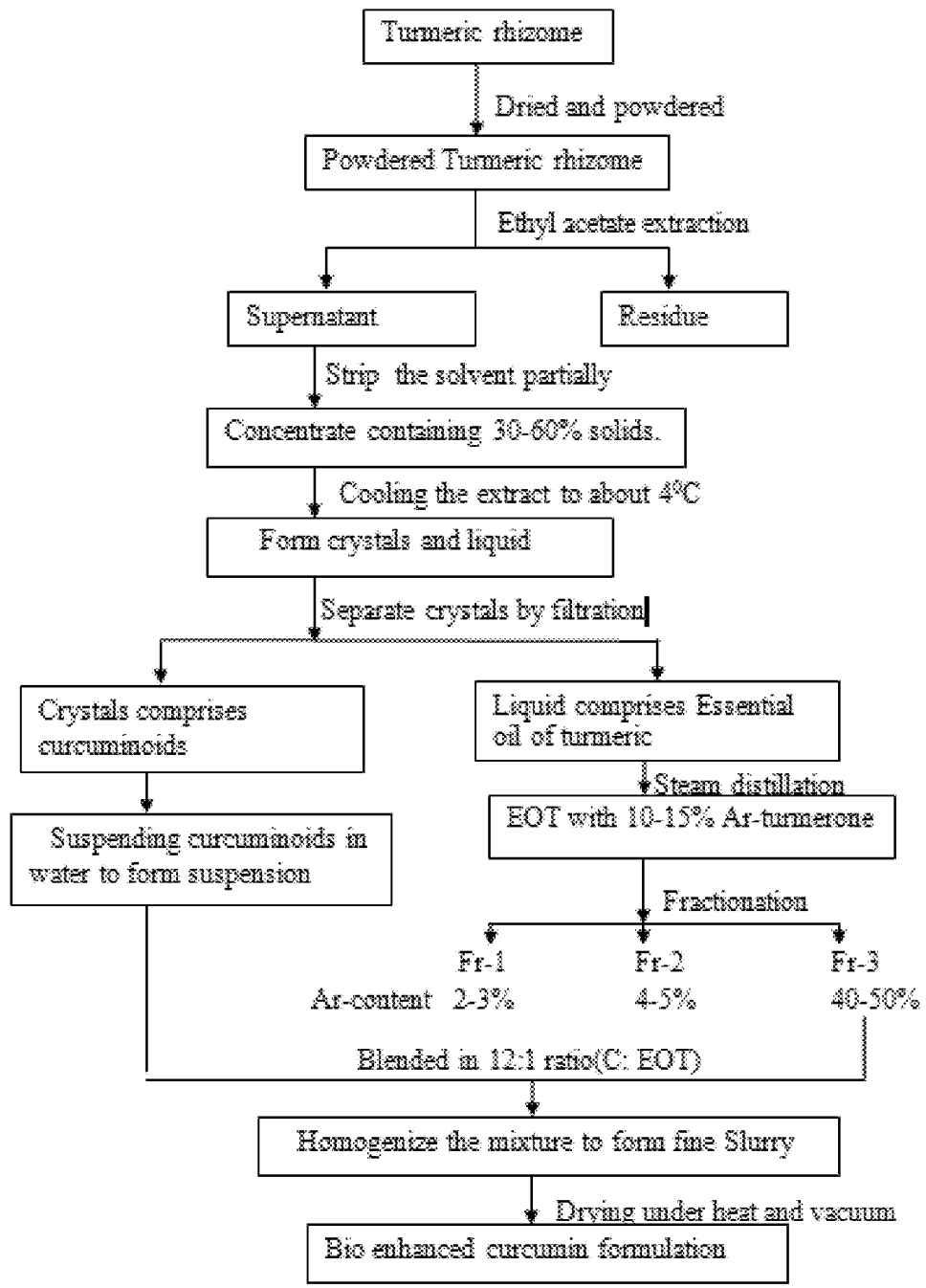
FIG. 2: Method of preparation of bio-enhanced turmeric formulation.
Figure 3A:
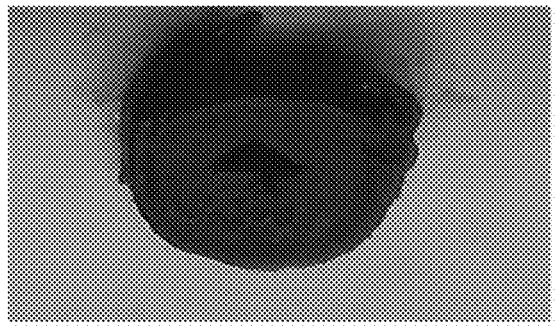
FIG. 3a: Effect of extract on Infarct size of heart homogenates; Control Group (0 mg/kg).
Figure 3B:
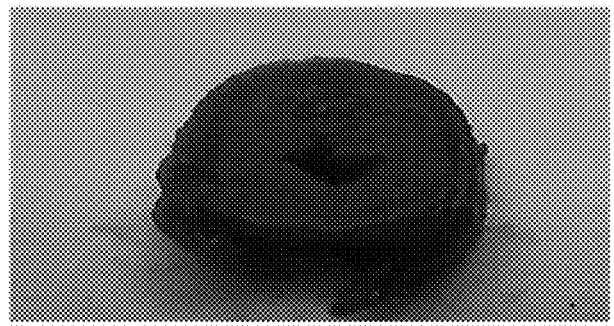
FIG. 3b: Effect of extract on Infarct size of heart homogenates; Sham Group (0 mg/kg).
Figure 3C:
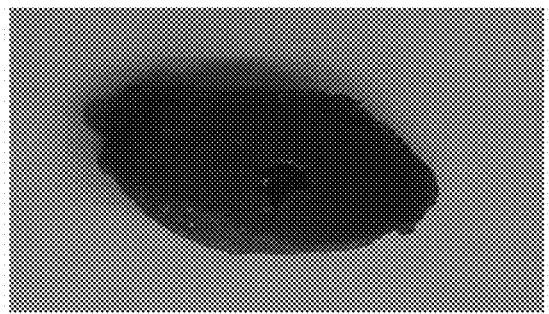
FIG. 3c: Effect of extract on Infarct size of heart homogenates; Positive Control Group.
Figure 3D:
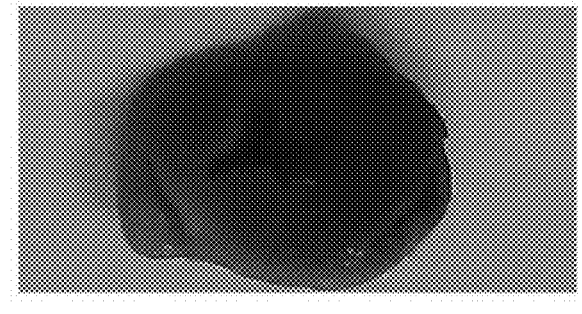
FIG. 3d: Effect of extract on Infarct size of heart homogenates; LAD Control Group (1/R only).
Figure 3E:
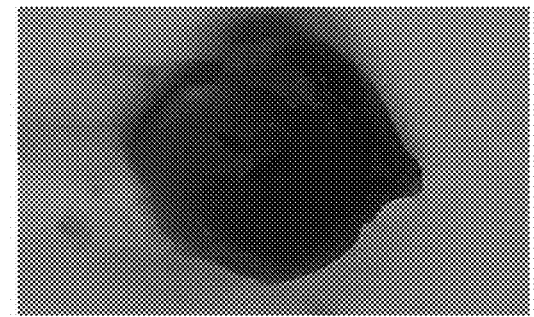
FIG. 3e: Effect of extract on Infarct size of heart homogenates; Low dose Group (45 mg/kg).
Figure 3F:
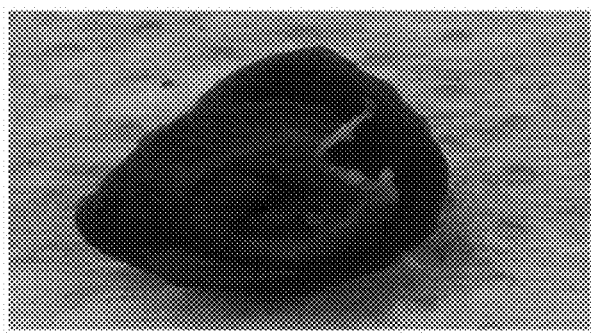
FIG. 3f: Effect of extract on Infarct size of heart homogenates: High dose Group (90 mg/kg).
Figure 3G:
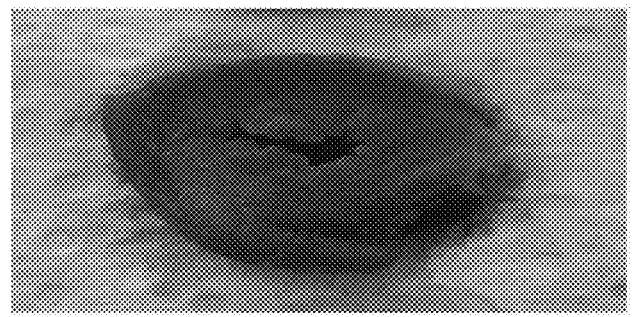
FIG. 3g: Effect of extract on Infarct size of heart homogenates: Combination Group (45 mg/kg—Amaranth extract+90 mg/kg—bio enhanced formulation).
Figure 3H:
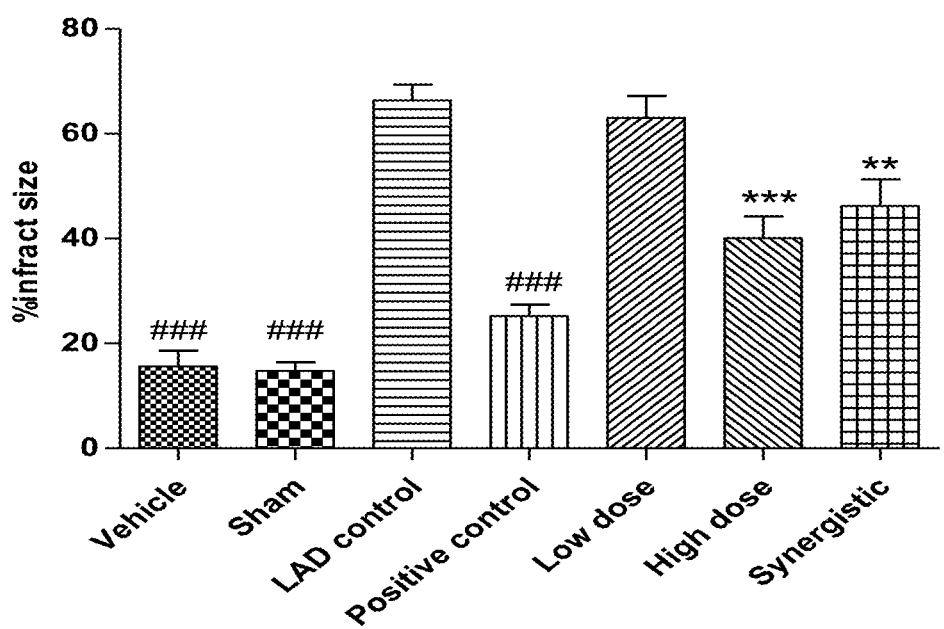
FIG. 3h: Effect of herbal extract on Infarct size of heart homogenates on 31st day.

The disclosure provides a method of extracting a curcuminoid from turmeric (refer to FIG. 2) by drying rhizomes of turmeric to form dried turmeric. The dried turmeric is powdered to form powdered turmeric. The powdered turmeric is treated with ethyl acetate to form a solution. The solvent is stripped from the solution to form an extract. The extract is cooled to about 4° C. to form crystals having curcuminoid mixture, and, a liquid. The liquid comprises the essential oil of turmeric and a resin. The crystals having the curcuminoid mixture are separated from the liquid.

In some embodiments, curcumin, demethoxycurcumin and bisdemethoxycurcumin comprise 95% of the curcuminoid crystals.

The volatile oil of turmeric was isolated by conventional methods of steam distillation to isolate essential oils. Fractionation of essential oil is done to get essential oil with different fractions of Ar-turmerone.

Curcuminoid and the essential oil are blended in a suitable proportion by a process including, suspending the curcuminoid in about 3 to 5 times its quantity of water, mixing in the essential oil, pulverizing in a colloidal mill into fine slurry, and stripping the slurry off water under heat and vacuum to obtain a uniform blend.

Figure 15:
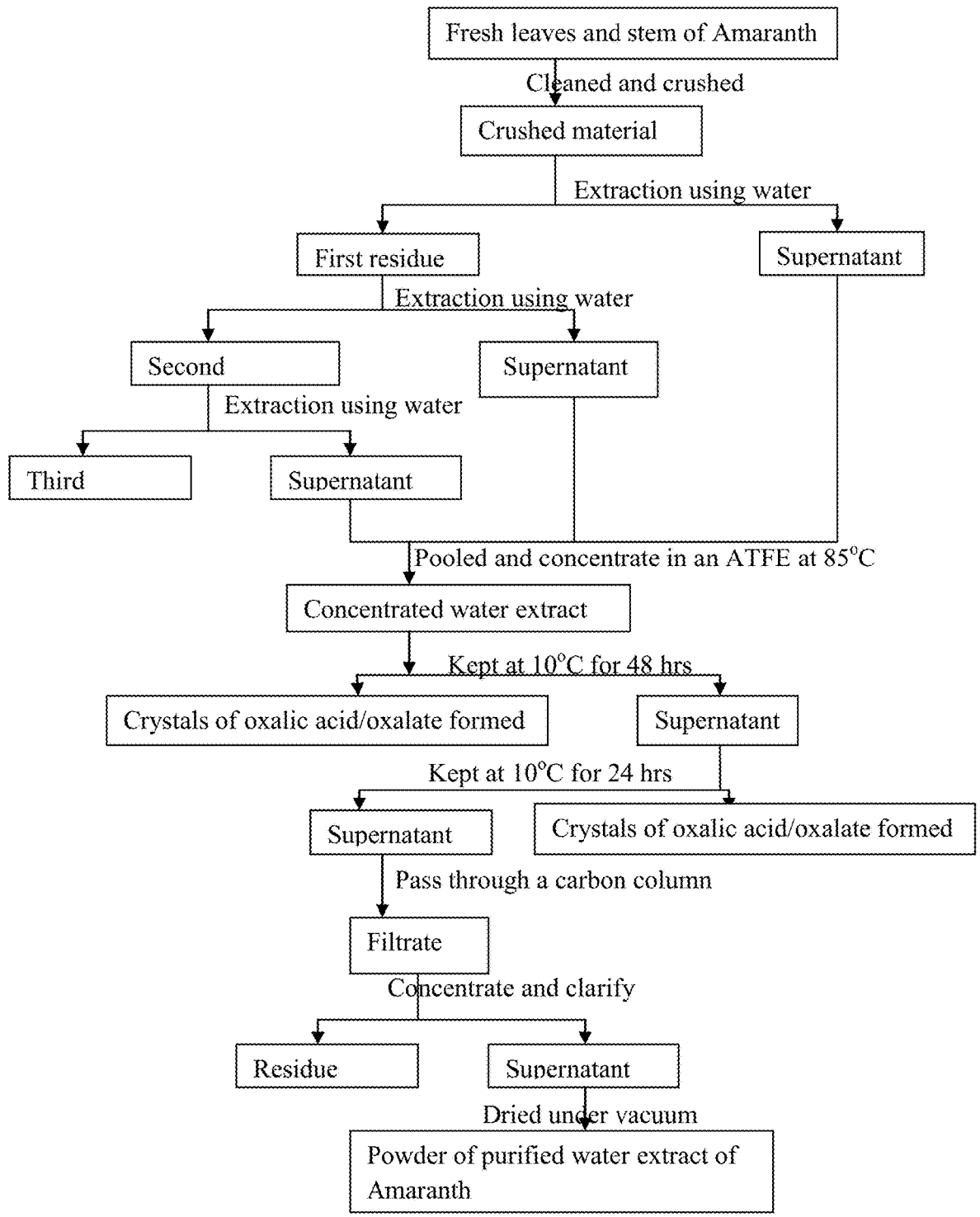
FIG. 15: Method of preparation of water extract of Amaranth with 9% nitrate.

FIG. 15 describes a method of preparation of purified Amaranth extract. Fresh leaves and stem of Amaranth is cleaned, crushed and extracted for about 1 hr using water in an extractor with reflux condenser to obtain residue and supernatant. The residue and supernatant is separated by draining out the supernatant from the extractor bottom through the filter cloth. The resultant supernatant is concentrated in an Agitated thin film evaporator (ATFE) at a temperature of 85° C. to form concentrated extract. Keep the concentrated water extract at 10° C. for 48 hr to crystallize oxalic acid or oxalates. Decant the supernatant and again keep the supernatant at 10° C. for another 24 hr to crystallize remaining oxalic acid or oxalates. Decant and filter the supernatant, supernatant is passed through a carbon column to obtain a filtrate. Filtrate is concentrated and clarified to form a supernatant and residue. Supernatant is dried under vacuum at above 500 mm of mercury to get powder of purified water extract of fresh Amaranth.

Figure 16:
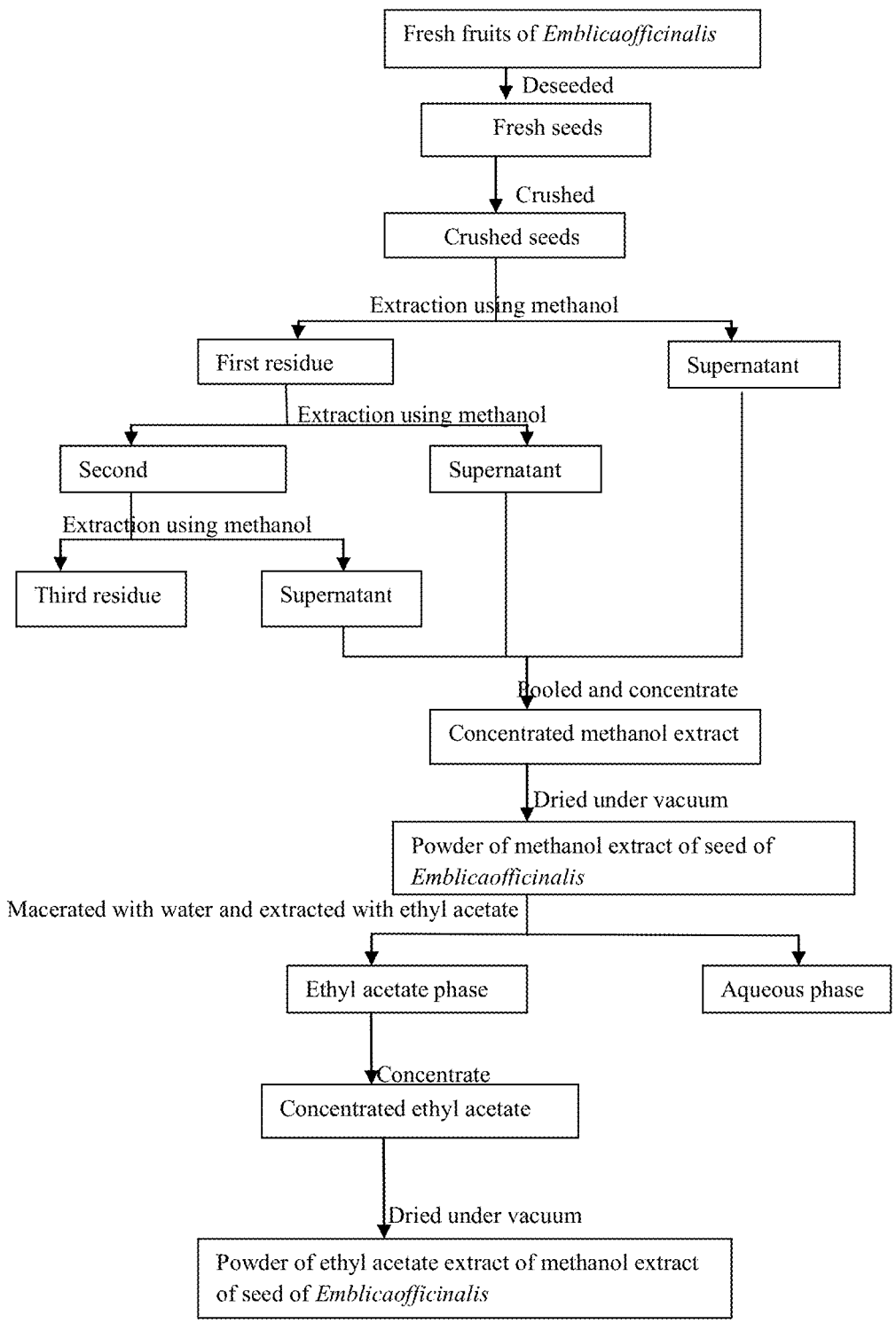
FIG. 16: Method of preparation of Amla seed extract.

FIG. 16 describes a method of preparation of Amla seed extract. Fresh fruit of *Emblica officinalis* is cleaned and deseeded. Seeds are crushed and extracted for about 1 hr using methanol in an extractor with reflux condenser to obtain residue and supernatant. The residue and supernatant is separated by draining out the supernatant from the extractor bottom through the filter cloth. The resultant supernatant is concentrated in an Agitated thin film evaporator (ATFE) at a temperature of 65° C. to form concentrated extract. Later the concentrated extract is dried under vacuum at above 500 mm of mercury to form powder of methanol extract of seed of *Emblica officinalis*.

The powder of methanol extract of seed of *Emblica officinalis* is macerated with water and partitioned with ethyl acetate. Collect the ethyl acetate part. Concentrate the ethyl acetate part in an Agitated thin film evaporator and dried under vacuum at above 500 mm of mercury to form powder of ethyl acetate extract of methanol extract of seed of *Emblica officinalis*.

Some embodiments provide a method of preparing a nitrate enriched extract of Amaranth. The method includes crushing fresh leaves and stem of Amaranth to obtain a first slurry. Then the first slurry is treated with pectinase to obtain a pectinase treated material. The pectinase treated material is heated to obtain a pectinase-deactivated material. The pectinase-deactivated material is extracted with water to obtain a supernatant and a residue. The supernatant is concentrated to obtain a concentrated water extract. The concentrated water extract is cooled at 10° C. for 48 hours then filtered to obtain crystals of oxalic acid and/or oxalate and a second supernatant. The second supernatant is cooled at 10° C. for 24 hours to obtain a third supernatant and a second oxalic acid and/or oxalate crystals. The third supernatant is filtered to obtain a filtrate. The filtrate is concentrated to obtain a concentrated filtrate. The concentrated filtrate is dried to obtain a powdered extract. The powdered extract is treated with hexane to obtain a residue. The residue of oxalic acid or oxalate free extract of Amaranth is dried after hexane extraction under vacuum to obtain nitrate enriched Amaranth extract. The nitrate enriched Amaranth extract is dissolved in a buffer having pH 5 to obtain a second slurry. The second slurry is treated with an enzyme mixture of protease and a cellulase at 50° C. The protease and the cellulase are deactivated by heating to 80° C. to obtain enzyme treated slurry. The enzyme treated slurry is passed through a carbon column and the filterate is collected. The filterate is centrifuged to obtain a supernatant and a residue. The supernatant is loaded on polyphenol resin column and eluted first with water followed by eluting with methanol to obtain a water eluate fraction and a methanol eluate fraction. The water fraction is concentrated and dried to obtain a powder of water extract of Amaranth enriched with nitrate.

A method of preparing a combination composition for oral administration having a composition a) having a nitrate enriched extract of Amaranth and a composition b) having a bio-enhanced turmeric formulation is provided. The composition a) includes about 0.1% to about 70% nitrates; about 1% to about 40% potassium, and, about 0.1% total oxalic acid. The composition b) includes a curcuminoid mixture and an essential oil of turmeric. The curcuminoid mixture consists of curcumin, demethoxycurcumin and bisdemethoxycurcumin. The essential oil of curcumin includes about 45% ar-turmerone. A weight ratio of curcuminoid mixture to essential oil of curcumin ranges from about 1:1 to about 99:1. The composition a) is prepared by a method including: crushing fresh leaves and stem of Amaranth to obtain a first slurry. Then the first slurry is treated with pectinase to obtain a pectinase treated material. The pectinase treated material is heated to obtain a pectinase-deactivated material. The pectinase-deactivated material is extracted with water to obtain a supernatant and a residue. The supernatant is concentrated to obtain a concentrated water extract. The concentrated water extract is cooled at 10° C. for 48 hours then filtered to obtain crystals of oxalic acid and/or oxalate and a second supernatant. The second supernatant is cooled at 10° C. for 24 hours to obtain a third supernatant and a second oxalic acid and/or oxalate crystals. The third supernatant is filtered to obtain a filtrate. The filtrate is concentrated to obtain a concentrated filtrate. The concentrated filtrate is dried to obtain a powdered extract. The powdered extract is treated with hexane to obtain a residue. The residue of oxalic acid or oxalate free extract of Amaranth is dried after hexane extraction under vacuum to obtain nitrate enriched Amaranth extract. The nitrate enriched Amaranth extract is dissolved in a buffer having pH 5 to obtain a second slurry. The second slurry is treated with an enzyme mixture of protease and a cellulase at 50° C. The protease and the cellulase are deactivated by heating to 80° C. to obtain enzyme treated slurry. The enzyme treated slurry is passed through a carbon column and the filterate is collected. The filterate is centrifuged to obtain a supernatant and a residue. The supernatant is loaded on polyphenol resin column and eluted first with water followed by eluting with methanol to obtain a water eluate fraction and a methanol eluate fraction. The water fraction is concentrated and dried to obtain a powder of water extract of Amaranth enriched with nitrate. The composition b) is prepared by a method including suspending the curcuminoid mixture in water to form a suspension. Next, adding the essential oil of turmeric to the suspension to form a mixture. Followed by homogenizing the mixture to obtain a slurry. Then, drying the slurry under heat and vacuum to form a uniform blend of the composition having bio-enhanced turmeric formulation. Whereby the composition b) has a curcuminoid mixture and an essential oil of turmeric. The curcuminoid mixture includes curcumin, demethoxycurcumin and bisdemethoxycurcumin. The essential oil of curcumin includes about 45% ar-turmerone. A weight ratio of curcuminoid mixture to essential oil of curcumin ranges from about 1:1 to about 99:1. Blending the composition a) and the composition b) results in the combination composition.

A method of preparing a combination composition for oral administration having a composition a) having a nitrate enriched extract of Amaranth and a composition b) having an extract of seed of *Emblica officinalis* is provided. The composition a) includes about 0.1% to about 70% nitrates; about 1% to about 40% potassium, and, about 0.1% total oxalic acid. The composition b) includes about 6% to about 50% of triterpenoids, about 2% to about 20% of hydroxycinnamic acids, about 10% to about 60% of fatty acids. The composition a) is prepared by a method including: crushing fresh leaves and stem of Amaranth to obtain a first slurry. Then the first slurry is treated with pectinase to obtain a pectinase treated material. The pectinase treated material is heated to obtain a pectinase-deactivated material. The pectinase-deactivated material is extracted with water to obtain a supernatant and a residue. The supernatant is concentrated to obtain a concentrated water extract. The concentrated water extract is cooled at 10° C. for 48 hours then filtered to obtain crystals of oxalic acid and/or oxalate and a second supernatant. The second supernatant is cooled at 10° C. for 24 hours to obtain a third supernatant and a second oxalic acid and/or oxalate crystals. The third supernatant is filtered to obtain a filtrate. The filtrate is concentrated to obtain a concentrated filtrate. The concentrated filtrate is dried to obtain a powdered extract. The powdered extract is treated with hexane to obtain a residue. The residue of oxalic acid or oxalate free extract of Amaranth is dried after hexane extraction under vacuum to obtain nitrate enriched Amaranth extract. The nitrate enriched Amaranth extract is dissolved in a buffer having pH 5 to obtain a second slurry. The second slurry is treated with an enzyme mixture of protease and a cellulase at 50° C. The protease and the cellulase are deactivated by heating to 80° C. to obtain enzyme treated slurry. The enzyme treated slurry is passed through a carbon column and the filterate is collected. The filterate is centrifuged to obtain a supernatant and a residue. The supernatant is loaded on polyphenol resin column and eluted first with water followed by eluting with methanol to obtain a water eluate fraction and a methanol eluate fraction. The water fraction is concentrated and dried to obtain a powder of water extract of Amaranth enriched with nitrate. The composition b) is prepared by a method including deseeding fresh fruits of *Emblica officinalis* to obtain seeds of *Emblica officinalis*. Next, crushing the seeds of *Emblica officinalis* to obtain crushed seeds. Then extracting the crushed seeds with 95% methanol to obtain a residue and a supernatant. Next, concentrating the supernatant to obtain a concentrated methanol extract. Next, drying the concentrated methanol extract to obtain a powder of methanol extract of seeds of *Emblica officinalis*. Next, macerating the powder of methanol extract of seeds of *Emblica officinalis* in water to obtain a liquid. Then, extracting the liquid with ethyl acetate to obtain an ethyl acetate phase. Next, concentrating the ethyl acetate phase to obtain a concentrated ethyl acetate phase. Then, drying the concentrated ethyl acetate phase to obtain a powder of ethyl acetate extract of methanol extract of seed of *Emblica officinalis*. Blending the composition a) and the composition b) results in a combination composition having nitrate enriched extract of Amaranth and extract of seeds of *Emblica officinalis*.

Details of some of the trials/experiments carried out, and findings are explained below by way of examples.

Example 1

Process of Enrichment of Nitrate and Removal of Amino Acid.

100 kg of fresh Amaranth were collected. Leaves and stem of fresh Amaranth were cleaned and crushed to make slurry. The slurry was treated with 1% pectinase for 2 Hrs. The enzyme was deactivated by heating the slurry at 90° C. for 10 minutes. The extraction was performed with water using an extractor with a reflux condenser. The bottom of the extractor was fitted with a polypropylene (100 microns) filter cloth. The enzyme treated slurry was refluxed for one hour to obtain a first residue and supernatant and were separated by draining out the supernatant from the extractor bottom through the polypropylene filter cloth using a centrifugal pump. After the first extraction, the first residue was further extracted with ten times the quantity of water to get second residue and supernatant. The second residue was further extracted with ten times the quantity of water to get third residue and supernatant. All the supernatants were pooled and concentrated in an Agitated thin film evaporator (ATFE) at a temperature of 85° C. to form 3.5 Kg of concentrated water extract (Sample 1).

Sample 1 was kept at 10° C. for 48 hr to crystallize oxalic acid or oxalates. The supernatant was decanted off and again kept at 10° C. for 24 hr to crystallise remaining oxalic acid or oxalates. The supernatant from this solution was filtered and evaporated to dryness under vacuum to get 2.2 Kg of oxalic acid or oxalate free Amaranth extract (sample 2).

Sample 2 was further extracted with hexane for 6 hours in a Soxhlet extractor. Oxalic acid or oxalate free Amaranth extract after hexane treatment was dried under vacuum to get 1.6 Kg of nitrate enriched Amaranth extract (sample 3). The nitrate content of the extract was found to be 18% as determined by ion chromatography.

Sample 3 was dissolved in a buffer of pH 5 to form a slurry. The slurry was treated with enzyme protease and 1% cellulase and incubated for 6 hrs at 50° C. The enzyme was deactivated by heating the slurry at 80° C. for 10 minutes. Protease and cellulase treated slurry was passed through carbon column to obtain a filtrate [sample 4]. The filtrate obtained was loaded on a polyphenol resin column FPX66. Before passing the filtrate through the column, resin was initially washed with water. After washing the resin, the filtrate was loaded onto the column and eluted with methanol followed by water. Water and methanol fractions were collected and separately concentrated in an Agitated thin film evaporator (ATFE) to form concentrated water fraction and methanol fraction respectively. Each fraction was separately fed into vacuum stripper and dried under vacuum at above 500 mm of mercury. Methanol fraction was discarded and 1 Kg water fration [sample 5] was found to contain 70% nitrate, 25% potassium and 0.03% oxalic acid or oxalate. See also extract preparation in FIG. 1.

Sample 1 (water extract) was found to contain about 2% nitrate, about 30% oxalic acid, about 2.3% saponin, about 1.2% alkaloids, about 20% carbohydrate, about 18% protein, about 1.5% flavonoids, about 1.6% L-arginine and about 2.3% potassium.

Sample 2 (after removing oxalic acid) was found to contain about 5% nitrate, about 0.09% oxalic acid, about 3.1% saponin, about 1.8% alkaloids, about 20% carbohydrate, about 19% protein, about 2.1% flavonoids, 1.8% L-arginine and about 4.5% potassium.

Sample 3 (After hexane treatment) was found to contain about 18% nitrate, about 0.09% oxalic acid, about 8% saponin, about 4% alkaloids, about 24% carbohydrate, about 22% protein, about 6% flavonoids, about 3% L-arginine and about 17% potassium.

Sample 4 (After carbon column treatment) was found to contain about 30% nitrate, about 0.05% oxalic acid, about 10% saponin, about 4.3% alkaloids, about 5% carbohydrate, about 4% protein, about 6.5% flavonoids, about 1.5% L-arginine and about 21% potassium.

Sample 5 (after passing through polyphenol resin column) was found to contain about 70% nitrate, about 0.03% oxalic acid and about 25% potassium.

Example 2

Method of Preparation of Curcuminoid Mixture With 95% Curcuminoids.

300 Kg of rhizomes of turmeric were dried. The dried turmeric rhizomes were powdered to form powdered turmeric. The powdered turmeric was treated with 900 L ethyl acetate to form a solution. The extraction was carried out at 78° C. temperature for 1 hr. After initial extraction, the extraction process was repeated 4 more times, and the resultant solution was filtered, and the solvent was stripped from the filtered solution to form an extract. This extract was cooled to about 4° C. to obtain crystals of curcuminoid (12 Kg) and a liquid. The crystals of curcuminoid were isolated from the liquid by filtration. The crystals were powdered to form powdered curcuminoid mixture with 95% curcuminoids. Curcuminoid mixture includes curcumin, demethoxycurcumin and bisdemethoxycurcumin. See also extract preparation in FIG. 2.

Example 3

Method of Preparation of Essential Oil of Turmeric with Varying Concentration of Ar-turmerone.

500 Kg of rhizomes of turmeric were dried. The dried turmeric rhizomes were powdered to form powdered turmeric. The powdered turmeric was treated with 1500 L ethyl acetate to form a solution. The extraction was carried out at 78° C. temperature for 1 hr. After initial extraction, the extraction process was repeated 4 more times, and the resultant solution was filtered, and the solvent was stripped from the filtered solution to form an extract. This extract was cooled to about 4° C. to obtain 20 Kg crystals of curcuminoid and a liquid. The crystals of curcuminoid were isolated from the liquid by filtration.

The remaining liquid comprises the essential oil of turmeric and resin. The liquid was then steam distilled to isolate essential oil of turmeric with 10-15% Ar turmerone (25 Kg). After fractionating this oil, essential oil with 45% Ar turmerone (7.5 Kg) was obtained as fraction 3, essential oil of turmeric with 4-5% Ar turmerone (8.3) was obtained as fraction 2 and essential oil of turmeric with 2-3% Ar turmerone (9.3 Kg) was obtained as fraction 1. See also FIG. 2.

Example 4

A Method of Preparation of Combination of Curcuminoids and Essential Oil of Turmeric With 45% Ar turmerone in 12:1 Ratio (Bio-Enhanced Turmeric Formulation).

3.5 Kg of curcuminoid powder prepared as per Example 2 was suspended in 15 L water to form a suspension, 0.29 Kg of fraction of essential oil containing 45% Ar-turmerone prepared as per Example 3 was added to the suspension in 12:1 ratio. The mixture is pulverized in a colloidal mill to form fine slurry. Water is stripped from the slurry under heat and vacuum to form a uniform blend (3.8 Kg) having powder of curcuminoid mixture and essential oil containing 45% Ar-turmerone with curcumin 69.5%, demethoxy curcumin 17% and bisdemethoxy curcumin 4% and Essential oil of turmeric 7.5%.

Example 5

Study to evaluate the protective activity potential of Amaranth extract with 9% nitrate and a combination of Amaranth extract with 9% nitrate and bio-enhanced turmeric formulation against myocardial ischemia reperfusion injury in rats through ligation of the left anterior descending coronary artery (LAD) in rats.

56 male and female Wistar rats weighing approximate 150-200 gm were selected for the study. The animals were kept in the experimental room for 1 week after veterinary examination. Standard rodent feed was provided ad libitum throughout the experimental period except for the fasting period if any.

Rats were divided into seven groups with eight animals (4 males & 4 females) in each group.

| Group | Treatment | Dose (mg/Kg) |
|---|---|---|
| G1 | Vehicle Control | — |
| G2 | Sham Control | — |
| G3 | LAD Control (Ischemic Reperfusion only) | — |
| G4 | Verapamil (Positive control) (Ischemic Reperfusion only) | 10 |
| G5 | Amaranth extract (Ischemic Reperfusion + Amaranth extract) | 45 |
| G6 | Amaranth extract (Ischemic Reperfusion + Amaranth extract) | 90 |
| G7 | Amaranth extract + bio-enhanced turmeric formulation (Ischemic Reperfusion + Amaranth extract + bioenhanced turmeric formulation) | Amaranth extract = 45 Bioenhanced turmeric formulation = 45 |

Animals in each group were treated with doses mentioned in study design once daily for 30 days. On day 31, after 45 minutes of ischemia by ligation of the left anterior descending coronary artery (LAD), the myocardium was reperfused for 60 mins after knot release.

Blood samples were collected from retro orbital puncture after two hours of reperfusion (6 rats from each group) to determine the serum levels of CK, LDH levels, troponin I, using ELISA kits and levels of pro-inflammatory cytokines like IL-6, TNF-α in myocardial tissue homogenate were detected. Protein concentrations are determined using the BCA protein assay. Total protein is used to calculate MDA, nitrite, SOD, GSH, TNF-α, IL-6 and cGMP. Oxido-nitrosative stress is measured in terms of Nitric oxide, MDA level and activities of antioxidant SOD and GSH in heart homogenates.

The levels of SOD, MDA and GSH in the serum are measured by a colorimetric method using commercial kits. Plasma cGMP levels are determined at day 0, day 30 and day 31 (before the start of the test product, before the procedure (ligation) and after the procedure (during or end of reperfusion phase). Radioimmunoassay methodology (RIA kit) is used to measure plasma cGMP levels. The rats are then anaesthetized with intraperitoneal injection of 1% sodium pentobarbital solution (65 mg/kg), after which they are sacrificed. The hearts are removed immediately, and myocardial infarct size is measured and expressed as a percentage of infarct size over total AAR.

Measurement of Cardiac Injury

Two hours after Myocardial I/R, six rats from each group were sacrificed immediately after collection of blood samples.

Rats were sacrificed by decapitation: tissues were carefully removed and rinsed with ice-cold (0.9% w/v) isotonic saline. The tissues were then homogenised with ice-cold 0.1 M phosphate buffer (pH 7.4) in a ten times (w/v) volume. The homogenate was centrifuged (Remi Cooling compufuge CPR 24) at 10,000 rpm for 15 minutes (4° C.), and aliquots of supernatant were separated. For plasma extractions, the collected blood samples were centrifuged for 15 min at 6000 rpm.

Protein concentrations were determined using the BCA protein assay. Total protein was used to calculate MDA, nitrite, SOD, GSH, TNF-α, IL-6 and cGMP.

Aliquots from extractions were separated by 8% sodium dodecyl sulfate-polyacrylamide gel electrophoresis, electrotransferred to a cellulose acetate membrane, and was blocked with 0.1% Tween for two hours at room temperature. They were then incubated overnight with rats antibodies (1:1000 dilutions) at 4° C., before conjugation with anti-rat secondary antibodies (1:1000 dilution) for one hour at room temperature. After extensive washing, immunoreactive proteins were detected using an enhanced chemiluminescence/fluorescence detection system.

Measurement of Myocardial Infarct Size

Tissues were sliced into 2 mm thick coronal sections and stained with 2% (w/v) 2,3,5-triphenyltetrazolium chloride (Sigma-Aldrich) for 30 min at 37° C. followed by immersion in 4% (w/v) in phosphate buffer for 30 min, and then paraformaldehyde for colour fixation. The non-infarct region turns red, whereas infarct region remained unstained (white). The infarct area was demarcated, analysed using image J software and expressed as a percentage of infarct size.

Measurement of Cardiac Enzyme Levels (ELISA Essay)

Blood samples were collected 2 hours after Myocardial I/R injury. Serum and plasma levels of CK, LDH levels, troponin I and myoglobin level was measured spectrophotometrically using ELISA kits—Spinreact LDH kit (Cat no. 1001260) and Coral clinical system kit (Cat no. CKB1222) for CKMB.

TABLE 2

Summary of cardiac enzyme levels
Dose Group

|  | G 1 | G 2 | G 3 | G 4 | G 5 | G 6 | G 7 |
|---|---|---|---|---|---|---|---|
| Heart LDH (IU/L) | 7.61 ± 1.59 | 7.27 ± 1.70 | 26.90 ± 3.15 | 15.39 ± 2.09 | 22.13 ± 2.04 | 11.32 ± 1.94 | 8.75 ± 0.91 |
| % improvement compared to G3. |  |  |  | 60% | 45% | 80% | 90% |
| Plasma LDH (IU/L) | 57.17 ± 7.4 | 52.05 ± 7.7 | 230.7 ± 17 | 158.0 ± 6.30 | 163.9 ± 7.70 | 105.3 ± 10 | 122.9 ± 6.10 |
| % improvement compared to G3. |  |  |  | 40% | 38% | 70% | 60% |
| Heart CK-MB (IU/L) | 8.35 ± 1.40 | 8.19 ± 1.30 | 34.53 ± 3.8 | 16.85 ± 3.10 | 18.33 ± 3.30 | 11.93 ± 1.50 | 16.11 ± 3 |
| % improvement compared to G3. |  |  |  | 69% | 62% | 85% | 69% |
| Plasma CK-MB (IU/L) | 9.91 ± 1.60 | 9.59 ± 1.50 | 69.63 ± 5.8 | 41.15 ± 3.80 | 54.23 ± 6.60 | 30.53 ± 4.10 | 31.51 ± 3.40 |
| % improvement compared to G3. |  |  |  | 47% | 25% | 66% | 63% |
| Myoglobin-Heart(ug/ml) | 12.48 ± 4.36 | 18.38 ± 4.06 | 57.88 ± 10.51 | 8.73 ± 2.27 | 28.33 ± 6.60 | 14.66 ± 3.83 | 10.33 ± 1.95 |
| % improvement compared to G3. |  |  |  | 123% | 75% | 110% | 120% |
| Myoglobin-Serum(ug/ml) | 51.88 ± 11.17 | 74.38 ± 14.31 | 141.0 ± 29.46 | 56.38 ± 11.85 | 131.0 ± 25.18 | 44.25 ± 8.16 | 49.13 ± 16.92 |
| % improvement compared to G3. |  |  |  | 127% | 15% | 145% | 137% |
| Troponin (IU/L) | ND | ND | 0.83 ± 0.02 | ND | 0.76 ± 0.02 | 0.59 ± 0.01 | ND |
| % improvement compared to G3. |  |  |  | — | 8% | 29% | — |

TABLE 1

Summary of myocardial infarct size (is) expressed as percent of the total ischemic-reperfused area (area-at-risk, AAR).

| Dose Group | Infarct size (%) | % improvement compared to G 3. |
|---|---|---|
| G 1 | 15.63 ± 2.99 |  |
| G 2 | 14.76 ± 1.68 |  |
| G3 | 66.38 ± 2.97 |  |
| G 4 | 25.25 ± 2.18 | 79% |
| G 5 | 63.03 ± 4.23 | 6% |
| G 6 | 40.08 ± 4.13 | 50% |
| G7 | 46.25 ± 5.02 | 38% |

To evaluate the cardio protective effect of test formulation on myocardial I/R injury TTC staining was used to analyse the infarct area (FIGS. 3 a-g and 3h). Myocardial infarct size was significantly increased in IR group compared with the control group. In contrast, this effect was considerably diminished by pre treatment with Amaranth extract, particularly at the high dose group and combination group. Positive control also shows a significant decrease in % infarct size.

As shown in FIG. 4a, 4b, 4c, 4d, 4e, 4f, levels of CK-MB, LDH and Myoglobin level (in plasma and serum) were remarkably increased in rats of I/R group compared with control group. Pre-conditioning with test formulation at all tested dosages drop the level of LDH, CK-MB and myoglobin, but significantly attenuated the release at the dosage of 90 mg/kg in high dose and combination treatment group compared with the, I/R group.

No significant changes were observed in the Troponin I level in all the treatment groups (FIG. 4g).

Measurement of Myocardial Apoptosis

Myocardial apoptosis was determined by terminal deoxynucleotidyl transferase (TdT enzyme)-mediated dUTP nick end labelling (TUNEL) (Roche, Switzerland) detection kit. In brief, tissue slides (4 slides/heart sample) was photographed digitally (×400) using a QICAM-Fast Digital Camera mounted onto an Olympus BX51 fluorescence microscope (Olympus, Japan) to cover the entire area. In this method, the TUNEL-positive brown-colored cells were considered to be apoptotic cells. The results were scored semiquantitatively by averaging the number of apoptotic cells/field at 400× magnification. Five fields were evaluated per tissue sample, and the cardiomyocytes apoptosis was represented as apoptosis index (AI). The apoptotic index (AI) (myocardial apoptosis index=number of apoptotic myocardial cells/total number of myocardial nuclei×100%) was calculated.

TABLE 3

Summary of myocardial apoptosis.

| Dose Group | Apoptotic index (%) | % Improvement compared to G 3 | Caspase-3 (pg/mg) | % Improvement compared to G 3 |
|---|---|---|---|---|
| G 1 | 20.18 ± 1.20 | | 494.0 ± 15 | |
| G 2 | 18 ± 1.20 | | 361.0 ± 29 | |
| G 3 | 78.25 ± 3.40 | | 1160 ± 63 | |
| G 4 | 31.75 ± 1.50 | 77% | 565.0 ± 44 | 74% |
| G 5 | 64.38 ± 4.50 | 23% | 865.9 ± 65 | 37% |
| G 6 | 62.13 ± 5.60 | 27% | 811.6 ± 31 | 44% |
| G 7 | 60.50 ± 4.00 | 30% | 750.8 ± 49 | 51% |

FIGS. 5a and 5c, showed that the Ischemia and reperfusion induced myocardial injury significantly increased the percentage of apoptosis, and it was significantly attenuated in treatment groups. The percentage of apoptotic cells was attenuated by pre-treatment with test formulation at low dose of 45 mg/kg, high dose of 90 mg/kg and combination group of 45+90 mg/kg respectively when compared to I/R group.

Levels of caspase-3 were remark-ably increased in rats of I/R group compared with control group. Pretreatment with test formulation significantly reduced the caspase-3 levels at a dosage of 45 mg/kg, 90 mg/kg and the combination group at a dosage of 45+90 mg/kg compared with the I/R group (FIG. 5b).

Biochemical Estimations—Pro-Inflammatory Markers

At 3 h of reperfusion, the rats were anaesthetized with intraperitoneal injection of 1% sodium pentobarbital solution (65 mg/kg), after which they were sacrificed for collection of serum and myocardial tissue. Levels of pro-inflammatory cytokines like IL-6, TNF-α in myocardial tissue homogenate, cardiomyocytes supernatant, and serum was detected. Spinreact total proteins kit (Cat no. 1001291) was used to detect the protein quantization. The interleukin levels were expressed as pg/mg pr.

TABLE 4

Summary of pro-inflammatory markers

| | G 1 | G 2 | G 3 | G 4 | G 5 | G 6 | G 7 |
|---|---|---|---|---|---|---|---|
| Serum IL-6 (pg/ml) | 98.88 ± 12 | 91.63 ± 10 | 303.9 ± 21 | 152.4 ± 13 | 265.4 ± 15 | 207.9 ± 17 | 184.5 ± 13 |
| % improvement compared to G3 | | | | 71% | 18% | 45% | 56% |
| Heart IL-6 (pg/mg pr) | 13.88 ± 4.15 | 23.63 ± 4.49 | 47.75 ± 6.63 | 13.63 ± 3.21 | 47.88 ± 9.54 | 22.50 ± 5.12 | 14.38 ± 3.18 |
| % improvement compared to G3 | | | | 140% | 0 | 100% | 136% |
| Serum TNF-α (pg/ml) | 45.25 ± 8.58 | 58.88 ± 10.2 | 293.5 ± 47.5 | 87.75 ± 9.78 | 179.5 ± 7.72 | 134.4 ± 15.7 | 1.45 ± 0.07 |
| % improvement compared to G3 | | | | 88% | 48% | 68% | 75% |
| TNF-α (pg/mg pr) Heart | 0.31 ± 0.05 | 0.19 ± 0.03 | 1.99 ± 0.07 | 0.84 ± 0.09 | 1.74 ± 0.07 | 1.45 ± 0.07 | 1.11 ± 0.10 |
| % improvement compared to G3 | | | | 64% | 14% | 30% | 49% |

Table 4 showed the change of IL-6 and TNF-3 (in serum and heart homogenate) concentration of all the tested doses (FIG. 6a-6d). In this study, we found that the plasma levels of IL-6 and TNF-α were significantly elevated following I/R injury compared with control group. Further, results determined that pretreatment with test formulation significantly attenuated the cytokines release. As expected, the treatment with test formulation dose-dependently protected the rats of I/R injury. In the combination group, the levels of inflammatory cytokines were mostly close to the positive control rats.

Biochemical Estimations—Oxido-Nitrosative Stress

Oxido-nitrosative stress was measured in terms of Superoxide production, Nitric oxide (Griess reagent assay), MDA level and activities of antioxidant SOD and GSH in heart homogenates. The levels of nitrite, SOD, MDA and GSH in the serum were measured by a colorimetric method or using commercial kits.

TABLE 5

Summary of oxido-nitrosative stress.

| | G 1 | G 2 | G 3 | G 4 | G 5 | G 6 | G 7 |
|---|---|---|---|---|---|---|---|
| Nitric oxide (umol/mg pr) | 6.51 ± 1.5 | 7.00 ± 1.5 | 34.82 ± 3.2 | 9.94 ± 2.4 | 18.57 ± 2.1 | 25.62 ± 3.7 | 14.88 ± 1.7 |
| % improvement compared to G3 | | | | 89% | 57% | 32% | 71% |
| MDA (nmol/mg pr) | 0.67 ± 0.08 | 0.67 ± 0.08 | 2.43 ± 0.17 | 0.90 ± 0.07 | 1.77 ± 0.13 | 1.37 ± 0.14 | 1.51 ± 0.09 |
| % improvement compared to G3 | | | | 87% | 36% | 60% | 51% |

TABLE 5-continued

Summary of oxido-nitrosative stress.

|  | G 1 | G 2 | G 3 | G 4 | G 5 | G 6 | G 7 |
|---|---|---|---|---|---|---|---|
| SOD (umol/mg pr) | 10.7 ± 0.8 | 10.42± | 2.76 ± 0.48 | 8.83 ± 0.6 | 4.58 ± 0.93 | 8.57 ± 0.69 | 9.84 ± 1.0 |
| % improvement compared to G3 |  |  |  | 86% | 29% | 86% | 100% |
| GSH (umol/mg pr) | 13.08 ± 1. | 12.60 ± 1.5 | 3.23 ± 0.64 | 11.61 ± 1.1 | 12.66 ± 1.3 | 5.39 ± 0.63 | 10.77 ± 1.4 |
| % improvement compared to G3 |  |  |  | 90% | 100% | 20% | 20% |

MDA level and nitric oxide are indicators of oxidative stress. As illustrated in table 5 and FIG. 7.a-d, the result showed that the level of nitric oxide potently decreased in low dose group, significantly decreased in high dose and combination group compared to LAD control. Levels of MDA significantly decreased in low dose and high dose in a dose-dependent manner by test formulation treatment. The combination group also showed the significant decrease in MDA level compared to I/R rats.

The activities of SOD significantly increased in a high dose and combination group by test formulation treatment when compared to I/R rats. The levels of GSH potently increased in low dose group and significantly increased in combination group when compared to R group.

Biochemical Estimations—cGMP Level

Plasma cGMP levels were determined at day 0 and day 30 (before the start of the test product, before the procedure (ligation) and after the procedure (during or end of reperfusion phase). Rat cGMP (Cyclic GMP) ELISA kit (Cat no. ER0831) by Fine test was used to measure plasma cGMP levels.

TABLE 6

Summary of cGMP level

| Dose Group | Day 0 (pmol/ml) | Day 30 (pmol/ml) |
|---|---|---|
| G 1 | 7.45 ± 1 | 9.09 ± 1.3 |
| G 2 | 7.04 ± 0.94 | 7.35 ± 1.1 |
| G 3 | 4.48 ± 2.1 | 3.23 ± 0.54 |
| G 4 | 11.40 ± 1.4 | 10.55 ± 1.6 |
| G 5 | 7.23 ± 1.2 | 3.10 ± 0.80 |
| G 6 | 6.12 ± 1.4 | 11.25 ± 1.2 |
| G 7 | 8.37 ± 1.2 | 12.11 ± 1.3 |

At day 0, no significant difference was observed in the treatment group. At day 30, the level of cGMP was remarkably increased in rats of positive group, high dose group and combination group compared with the I/R group at day 0. The increased cGMP level of high dose group was comparable with the positive group and was more significant with combination group (FIG. 8b).

From the above study, it was concluded that the protective effects of the extract of Amaranth (test formulation, TF) and its combination with bio-enhanced turmeric formulation on the myocardial ischemia-reperfusion injury. The results demonstrated that preconditioning with TF high dose group and combination group remarkably improved the I/R-induced cardiac injury through inhibition of inflammation and relieved the oxidative stress.

Cytokines, a heterogeneous group of proteins, have been associated with the inflammatory response in the progress of ischemia/reperfusion injury. It has been shown that ischemia/reperfusion (I/R) increases the relative levels of cytokines, such as TNF-α and IL-6 in the myocardium. We observed that the levels of cytokines had been decreased dose-dependently in the animals treated with TF. Moreover, the treatment of TF, which reduced the myocardial infarct size, may work as a cardio-protective agent.

From the results, we found that the I/R rats showed an increase in MDA production as well as a decrease in SOD level and GSH. MDA is an indicator of lipid peroxidation due to the release of ROS. SOD is one of the most significant intracellular antioxidant enzymes that could function as an ROS scavenger. GSH, a tripeptide composed of glutamate, exerts a critical role as antioxidant and neuromodulator in the central nervous system. The imbalance between oxidation and anti-oxidation leads to the oxidation injury. From the study, TF significantly reduced the levels of MDA and Nitrite, especially at 90 mg/kg dose and combination dose. Moreover, TF increased the activity of the anti-oxidase SOD and GSH, compared with the, I/R group. Taken these results together with the experiment data, it was suggested that the protective ability of TF against ischemia/reperfusion injury in vivo was exerted by means of reducing the oxidative stress. Further the significantly elevated level cGMP in high dose group and combination group was comparable and higher with the positive group respectively affirms its cardio-protective activity.

Furthermore, some results also indicated that TF used in combination with bio-enhanced turmeric formulation exerted a synergistic cardio-protective effect in vivo.

Infarct size is regarded as the standard in assessing the severity of MI/R injury. Following the administration of a series of doses of TF, the infarct size was reduced significantly at a high dose. Additionally, the sensitive cardiac injury markers CK-MB, was measured to determine whether TF is capable of alleviating the degree of myocardial injury caused by MI/R. The decreased release of CK-MB in the treatment groups demonstrated the protective effects of TF. LDH is one of the specific enzymes present in the myocardial cytoplasm, and its values may indirectly reflect the degree of damage of the myocardium exposed to I/R. In the present study, the LDH levels were significantly decreased following treatment with TF.

TF treatment significantly reduced the percentage of apoptotic cells when compared to control IR group, demonstrating its significant anti-apoptotic activity. Prevention of myocardial apoptosis was further supported by the decreased level of caspase-3 activity in treatment groups as compared with the I/R group.

Example 6

Method of Making Amaranth Extract With 9% Nitrate.

Fresh Amaranth were collected (100 Kg). Leaves and stem of fresh Amaranth were cleaned and crushed. Water in an amount ten times the quantity of crushed material of Amaranth was added to form a mixture. The extraction was performed using an extractor with a reflux condenser. The bottom of the extractor was fitted with a polypropylene (100 microns) filter cloth. The mixture was refluxed for one hour to obtain a first residue and supernatant and were separated by draining out the supernatant from the extractor bottom through the polypropylene filter cloth using a centrifugal pump. After the first extraction, the first residue was further extracted with ten times the quantity of water to get second residue and supernatant. The second residue was further extracted with ten times the quantity of water to get third residue and supernatant. All the supernatants were pooled and concentrated in an Agitated thin film evaporator (ATFE) at a temperature of 85° C. to form 3 Kg of concentrated water extract (sample 1).

Sample 1 was kept at 10° C. for 48 hr to crystallize oxalic acid or oxalates. The supernatant was decanted off and again kept at 10° C. for 24 hr to crystallise remaining oxalic acid or oxalates. The supernatant from this solution was filtered to get 2.2 Kg of oxalic acid or oxalate free Amaranth extract (sample 2).

Sample 2 was passed through a carbon column to obtain a filtrate. Filtrate was concentrated and clarified to form a supernatant and residue. Supernatant was dried under vacuum at above 500 mm of mercury to get 1.5 Kg of powder of purified water extract of fresh Amaranth (sample 3).

The nitrate content in sample 3 by ion chromatography was found to be about 9%, potassium content was about 18% and oxalic acid was about 0.07%. Further the sample 3 contained about 5% saponin, about 4.5% alkaloids, about 8% carbohydrate, about 6% protein, about 4.5% flavonoids and about 1% L-arginine.

Example 7

Method of Preparation of Ethyl Acetate Extract of Methanol Extract of Seed of *Emblica officinalis* (Amla Seed Extract)

500 Kg of fresh fruits of *Emblica officinalis* (Amla) were collected. Fruits were deseeded by deseeding machine and 75 Kg of fresh seeds obtained were crushed through roller mill. 95% methanol in an amount 2 times the quantity of crushed seeds was added to the crushed seeds to form a mixture for methanol extraction. The extraction was performed using an extractor with reflux condenser. The bottom of the extractor was fitted with a polypropylene (100 microns) filter cloth. The mixture was refluxed for one hour at 65° C. to obtain a first residue and supernatant and were separated by draining out the supernatant from the extractor bottom through the polypropylene filter cloth using a centrifugal pump. After the first extraction, the first residue was further extracted with two times the quantity of methanol at 65° C. to get second residue and supernatant. The second residue was further extracted with two times the quantity of methanol at 65° C. to get third residue and supernatant. All the supernatants were pooled and concentrated in an Agitated thin film evaporator (ATFE) at a temperature of 65° C. to form concentrated methanol extract. Concentrated methanol extract was dried under vacuum at above 500 mm of mercury to obtain 5 kg of powder of methanol extract of seed of *Emblica officinalis* (sample 1)

Sample 1 was macerated with water and transferred into a liquid-liquid extractor and extracted with ethyl acetate. Ethyl acetate phase and aqueous phase were separated. After extraction ethyl acetate phase was collected. Ethyl acetate phase was concentrated in an Agitated thin film evaporator to form concentrated ethyl acetate extract. Ethyl acetate concentrate was fed into vacuum stripper and dried under vacuum at above 500 mm of mercury to obtain 2.5 kg of powder of ethyl acetate extract of methanol extract of seed of *Emblica officinalis* (sample 2). Powder of ethyl acetate extract of methanol extract of seed of *Emblica officinalis* contain 9.5% triterpenoids, 4.3% hydroxycinnamic acid and 41.8% fatty acid.

Example 8

Study to evaluate the post treatment effect of Amaranth extract and a combination of Amaranth extract and bio-enhanced turmeric formulation against myocardial ischemia-reperfusion injury in rats through ligation of left anterior descending coronary artery (lad) in rats.

42 male and female Wistar rats weighing approximate 150-200 gm were selected for the study. The animals were kept in the experimental room for 1 week after veterinary examination. Standard rodent feed was provided ad libitum throughout the experimental period except for the fasting period if any.

Rats were divided into seven groups with Six animals (3 males & 3 females) in each group.

| Group | Treatment | Dose (mg/Kg) |
|---|---|---|
| G1 | Vehicle Control | — |
| G2 | Sham Control | — |
| G3 | LAD Control (Ischemic Reperfusion only) | — |
| G4 | Verapamil (Positive control) (Ischemic Reperfusion only) | 10 |
| G5 | Amaranth extract with 9% nitrate (Ischemic Reperfusion + Amaranth extract) | 45 |
| G6 | Amaranth extract with 9% nitrate (Ischemic Reperfusion + Amaranth extract) | 90 |
| G7 | Amaranth extract with 9% nitrate + bio-enhanced turmeric formulation (Ischemic Reperfusion + Amaranth extract) | Amaranth extract = 90 Bioenhanced turmeric formulation = 90 |

Ischemia was induced by ligation of the left anterior descending coronary artery (LAD) for 45 minutes and myocardium was reperfused for 7 days after knot release. The tested drug was administered daily starting from 4 hours after reperfusion until day 7. Animals in each group were treated with doses mentioned in study design.

Measurement of Cardiac Injury

The extent of cardiac injury was estimated in both heart homogenates and in blood after ischemic insult (45 min) followed by reperfusion (7 days). In brief, on day 7, animals were sacrificed and heart homogenates were used to estimate cardiac injury: measuring oxidative stress, cytokines, enzyme level and heart tissue was used for Hematoxylin and eosin staining. TTC staining and TUNEL staining. Total protein was used to calculate MDA, nitrite, SOD, GSH, TNF-α, IL-6 and cGMP.

Moreover, plasma samples were collected, after myocardial I/R injury and in plasma levels of CK-MB, LDH, troponin I and cGMP were determined.

Measurement of Infarct Size

Following reperfusion phase, the heart was quickly removed, freeze at −20° C. and sliced horizontally to yield four slices. The slices were incubated in 2% TTC prepared with phosphate buffer (pH 7.8) for 15 minutes at 37° C., and photographed with a digital camera. The areas stained with TTC (red staining, ischemic but viable myocardium), and TTC-negative area (white area, infarct size) was measured using image J software version 1.44. The myocardial infarct size was measured and expressed as a percentage of infarct size.

TABLE 1

Summary of myocardial infarct size (IS) expressed as percent of the total ischemic-reperfused area (area-at-risk, AAR).

| Dose Group | Infarct size (%) | Percentage decrease in infract size |
|---|---|---|
| G 1 | 24 | |
| G 2 | 19 | |
| G 3 | 75 | |
| G 4 | 25 | 98% |
| G 5 | 61 | 27% |
| G 6 | 55 | 39% |
| G7 | 33 | 82% |

Myocardial infarct size was significantly increased in I/R group compared with the control group. In contrast, this effect was considerably diminished by post treatment with test formulation, particularly at the dosage of 90 mg/kg in high dose group and 90+90 mg/kg in combination group. Positive control also showed significant decrease in percentage infarct size. (FIG. 9a-g).

Measurement of Cardiac Enzyme Levels (ELISA Essay)

Cardiac injury biomarkers were measured in heart homogenates (LDH and CKMB) and in plasma (LDH, CKMB and troponin) using the Coral Clinical Systems kit for CKMB, LDH kit of Accurex biomedicals and troponin I kit of Genxbio according to the manufacturer's instructions.

TABLE 2

Summary of cardiac enzyme levels Dose Group

| | G1 | G2 | G3 | G4 | G5 | G6 | G7 |
|---|---|---|---|---|---|---|---|
| Tissue LDH (IU/L) | 0.42 | 0.29 | 2 | 0.44 | 1.5 | 1.05 | 0.6 |
| % improvement compared with G3 | | | | 91% | 29% | 56% | 82% |
| Plasma LDH (IU/L) | 101 | 95 | 250 | 115 | 198 | 151 | 114 |
| % improvement compared with G3 | | | | 87% | 34% | 64% | 88% |
| Tissue CK-MB (IU/L) | 17 | 15 | 84 | 17 | 58 | 32 | 21 |
| % improvement compared with G3 | | | | 97% | 38% | 75% | 91% |
| Plasma CK-MB (IU/L) | 84 | 78 | 197 | 101 | 148 | 120 | 94 |
| % improvement compared with G3 | | | | 81% | 41% | 65% | 87% |
| Troponin (IU/L) | 0.15 | 0.13 | 0.68 | 0.16 | 0.48 | 0.32 | 0.19 |
| % improvement compared with G3 | | | | 95% | 36% | 65% | 89% |

As shown in FIG. 10a-e, levels of CK-MB and LDH level (in plasma and heart homogenate) and troponin level (plasma) were remarkably increased in rats of I/R group as compared with control group. Post-conditioning with test formulation at dosage of 90+90 mg/kg in the combination group significantly attenuated the level of LDH and CK-MB when compared with the LAD control in plasma samples. In tissue samples, high dose and combination groups significantly attenuated the levels of LDH and CKMB when compared to LAD control group.

No significant changes were observed in the troponin I level at dosage of 45 mg/kg in low dose while high dose and combination treatment groups at 90 mg/kg and 90+90 mg/kg, respectively significantly attenuated the levels as compared to LAD control.

Measurement of Myocardial Apoptosis

Myocardial apoptosis was determined by terminal deoxy-nucleotidyl transferase (TdT enzyme)-mediated dUTP nick end labeling (TUNEL) detection kit. In brief, tissue slides were photographed. In this method, the TUNEL-positive brown-colored cells were considered to be apoptotic cells. The results were scored by averaging the number of apoptotic cells/field at 100× magnification. Five fields were evaluated per tissue sample, and the cardio myocytes apoptosis was represented as apoptosis index (AI).

The apoptotic index (AI) (myocardial apoptosis index=number of apoptotic myocardial cells/total number of myocardial nuclei×100%) was calculated.

TABLE 3

Summary of myocardial apoptosis.

| Dose Group | Apoptotic index (%) | % improvement compared to G 3 |
|---|---|---|
| G1 | 15 | |
| G2 | 14 | |
| G3 | 85 | |
| G4 | 17 | 96% |
| G5 | 58 | 38% |
| G6 | 39 | 65% |
| G7 | 22 | 89% |

FIG. 11a-h, showed that the I/R induced myocardial injury significantly increased the percentage of apoptosis and it was significantly attenuated by post-treatment with test formulation in high dose and combination group when compared with LAD control. However, low dose treated animals group at 45 mg/kg showed less improvement percentage of apoptosis.

Biochemical Estimations—Pro-Inflammatory Markers

Levels of pro-inflammatory cytokines like IL-6, TNF-α in myocardial tissue homogenate and in plasma was detected using the kits from Wuhan fine biological tech Co Ltd. The pro-inflammatory cytokines levels were expressed as pg/mg protein or pg/ml for tissue and plasma samples respectively

TABLE 4

Summary of pro-inflammatory markers

| Dose Group | Plasma IL-6 (pg/ml) | % improvement compared to G3 | Tissue IL-6 (pg/mg pr) | % improvement compared to G3 | Plasma TNF-α (pg/ml) | % improvement compared to G3 | Tissue TNF-α (pg/mg pr) | % improvement compared to G3 |
|---|---|---|---|---|---|---|---|---|
| G1 | 97 | | 6 | | 39 | | 0.83 | |
| G2 | 110 | | 6 | | 39 | | 0.81 | |
| G3 | 486 | | 24 | | 195 | | 3 | |
| G4 | 149 | 90% | 7 | 94% | 76 | 76% | 1 | 91% |
| G5 | 380 | 28% | 21 | 17% | 150 | 29% | 2.5 | 23% |
| G6 | 280 | 55% | 16 | 44% | 112 | 53% | 1.52 | 68% |
| G7 | 179 | 82% | 9 | 83% | 85 | 71% | 0.9 | 96% |

FIG. 12a-d. showed the change of IL-6 and TNF-α (in serum and heart homogenate) concentration of all the tested rats. In this study, we found that the plasma levels of IL-6 and TNF-α were significantly elevated following I/R injury compared with control group. Further, results determined that post-treatment with test formulation in the combination group significantly attenuated the pro-inflammatory cytokines release in the plasma and tissue samples when compared with LAD control group. However, a significant reduction of TNF-α was noticed in high dose group compared to I/R group in tissue samples and plasma samples.
Biochemical Estimations—Oxido-Nitrosative Stress Oxido-nitrosative stress was measured in terms of Superoxide production, Nitric oxide (Griess reagent assay), MDA level and activities of antioxidant SOD and GSH in heart homogenates. The levels of nitrite, SOD, MDA and GSH in the serum were measured by a colorimetric method or using commercial kits.

TABLE 5

Summary of oxido-nitrosative stress.

| | G1 | G2 | G3 | G4 | G5 | G6 | G7 |
|---|---|---|---|---|---|---|---|
| MDAPlasma (nmol/ml) | 31 | 26 | 193 | 48 | 176 | 154 | 121 |
| % improvement Compared to G3 | | | | 87% | 25% | 46% | 84% |
| MDATissue (nmol/mg pr) | 19 | 17 | 68 | 30 | 60 | 47 | 35 |
| % improvement Compared to G3 | | | | 75% | 20% | 41% | 73% |
| Nitrite-plasma(umol/ml) | 56 | 56 | 279 | 138 | 253 | 201 | 154 |
| % improvement Compared to G3 | | | | 87% | 29% | 57% | 79% |
| Nitrite-Tissue(umol/mg pr) | 14 | 14 | 41 | 21 | 41 | 32 | 23 |
| % improvement Compared to G3 | | | | 81% | 22% | 48% | 74% |
| GSH-Plasma μmol/ml | 27 | 26 | 8 | 21 | 15 | 20 | 24 |
| % improvement Compared to G3 | | | | 83% | 28% | 56% | 78% |
| GSH-Tissue μmol/mg pr | 24 | 25 | 2 | 20 | 8 | 14 | 19 |
| % improvement Compared to G3 | | | | 78% | 26% | 52% | 74% |
| SOD-Plasma U/ml | 27 | 26 | 10 | 26 | 14 | 20 | 25 |
| % improvement Compared to G3 | | | | 88% | 25% | 63% | 81% |
| SOD-Tissue U/mg pr | 14 | 15 | 3 | 13 | 5 | 9 | 15 |
| % improvement Compared to G3 | | | | 83% | 25% | 50% | 75% |

MDA level, nitrite levels, GSH and SOD are indicators of oxidative stress. As illustrated in FIG. 13a-h, the results showed that I/R injury by LAD markedly increased the oxidative stress by elevating levels of MDA and nitrite and attenuating the levels of SOD and GSH. Further, the level of MDA and nitric oxide was significantly decreased by high dose and combination groups in plasma and tissue samples.

The activities of SOD and GSH were significantly improved in all treated groups in plasma and tissue.
Biochemical Estimations—cGMP Level Plasma cGMP levels were determined during early reperfusion and 7 days after the reperfusion using the Rat cGMP (Cyclic GMP) ELISA Kit. (Wuhan fine biological tech Co ltd).

TABLE

Summary of cGMP level

| Dose Group | Day 0 (pmol/ml) | Day 7 (pmol/ml) |
|---|---|---|
| G 1 | 9 | 9 |
| G 2 | 8 | 8 |
| G 3 | 8 | 4 |
| G 4 | 8 | 15 |
| G 5 | 8 | 9 |
| G 6 | 8 | 13 |
| G7 | 9 | 21 |

On day 0, no significant difference was observed among different groups in the study. On day 7, the level of cGMP was remarkably increased in rats of high dose group and combination group compared with the I/R group. Also, in low dose treated groups, we observed elevation of cGMP when compared to high dose and combination group (FIG. 14).

In conclusion, this study indicates that herbal based extract post-treatment has a protective effect against myocardial I/R injury via attenuating oxidative and pro-inflammatory cytokines level. Furthermore, we observed that the extract at high dose and in combination group post-treatment improved myocardial I/R injury by reducing cellular apoptosis and maintaining vasodilator action via cGMP level.

Further, the low dose was found to be moderately effective in attenuating the cardiac injury in most of the parameters while combination group was found more effective as compared to high dose alone treated group.

Example 9

Cardioprotective Effects of Amaranth Extract and Amla Seed Extract in L-NAME-Induced Hypertensive Rats N(G)-nitro-L-arginine-methyl ester (L-NAME) induced hypertension and cardiac injury is a well-established experimental model characterized by generalized NO deficiency and progressive increase in BP if prolonged. As L-NAME model mimics hypertension in human, it is very suitable to study the cardiovascular effects of new agents. The precise mechanism bases on the fact that L-NAME, a structural analog of L-arginine, is metabolize by nonenzymatic hydrolysis into the active form, N omega-nitro-L-arginine (L-NO-ARG), which competitively binds to endothelial NOS. NOS inhibition attenuates both the synthesis and metabolism of NO, the smallest gaseous intercellular signaling molecule mediating the vascular relaxation. Subsequently, NO deficiency leads to systemic vasoconstriction and hypertension.

Adult male Sprague-Dawley rats with 160-180 g were used. All animals were housed at 24±2° C. temperature, 30-70% relative humidity and 12 h light/dark cycle. They were fed with standard chow diet. All animal procedures were performed in accordance with the recommendations of the Committee for the Purpose of Control and Supervision of Experiments on Animals (CPCSEA) guidelines for care and use of laboratory animals. The protocol was approved by the Institutional Animals Ethics Committee (IAEC).

Experimental Design

Hypertension was induced according by oral administration of 50 mg/kg/day of N(G)-nitro-L-arginine-methyl ester (L-NAME) in distilled water. Treatment was carried out as follows (8 rats in each group):

Group 1: Normal control: received only the vehicle orally
Group 2: Hypertensive control: received L-NAME (50 mg/kg/day) orally for 4 weeks
Group 3: Amaranth extract group: received L-NAME+ extract of Amaranth (45 mg/kg) for 4 weeks
Group 4: Amla seed group: received L-NAME+Amla seed extract (10 mg/kg) for 4 weeks
Group 5: Combination group: received L-NAME+Amaranth extract (45 mg/kg)+Amla seed extract (10 mg/kg) for 4 weeks Blood Pressure (BP) Recording BP (systolic and diastolic) of conscious rats was measured at the start of the experiment (baseline), 2 weeks and 4 weeks of treatment. Animals were restrained in the tubes for 10-20 min/day for 5 days prior to recording BP in the tail-cuff technique, and the animals were warmed for 30 min at 28° C. in a thermostatically controlled heating cabinet for better detection of tail artery pulse, where the tail was passed through a cuff and a tail-cuff sensor that was connected to an amplifier. The amplified pulse was recorded during automatic inflation and deflation of the cuff. The mean arterial blood pressure (MAP) was calculated using the following formula:

$$MAP = DBP + 0.412(SBP - DBP)$$

Twenty four hours after the last treatment, animals were anesthetized with ethyl ether. Blood samples were collected by retro-orbital puncture and centrifuged at 4000 rpm for 10 min to separate serum for measurement of lipid profile. Afterward, all animals were sacrificed by cervical dislocation under ethyl ether anesthesia; the heart and thoracic aorta were immediately removed, rinsed in ice-cold normal saline, and placed in 10% neutral buffered formalin for histopathological examination.

Lipid Profile Analysis

Serum samples were used to measure lipid profile. Total cholesterol, triglycerides, and high-density lipoprotein (HDL) was estimated by standard commercial kits. Very low-density lipoprotein (VLDL) was calculated by dividing TG value by five. Low-density lipoprotein (LDL) was calculated using Friedewald formula.

Histopathological Examination and IMT Measurement

The heart and segment from thoracic aorta of the different groups were fixed and processed for obtaining 4 μm paraffin embedding sections. The sections were stained with hematoxylin and eosin (H&E) and MT stain for assessment of fibrosis. The histopathological lesion scoring of the myocardium was performed according to Kanda et al., using a scale from 0 to 4 as follows: 0 normal; 1 mild; 2 moderate; 3 severe; and 4 very severe. The percentage of the myocardial fibrosis (%) was performed as the mean of 10 fields/slide using Leica Qwin 500 Image Analyzer (Leica, Cambridge, England). The aorta intima media thickness (from the internal to the external elastic lamellae) was measured in five sections of the thoracic aorta obtained from each group.

Results

Blood Pressure

In the present study, oral administration of L-NAME was associated with a significant rise in MAP compared with the normotensive control rats, validating the induction of hypertension. As presented in the Table, the baseline MAP is recorded about 96 mmHg for all the groups. Rats administered with L-NAME (50 mg/kg/day) showed higher MAP than normal control rats after 2 weeks and 4 weeks (Hypertensive control group). That is 82% increase in MAP compared to baseline. Administration of Amaranth extract or Amla seed extract caused a significant decline of MAP in the hypertensive rats. After Amaranth extract administration, the percentage increase in MAP is 17% compared to baseline. That is, 4.8 fold less increase in MAP compared to untreated control. Amla seed extract administration showed 54% increase in MAP compared to baseline or 1.5 fold less increase in MAP compared to untreated control. A combination of Amaranth extract and Amla seed extract reduced the MAP to almost normal (2% increase). Combination of Amaranth extract and Amla seed extract showed 41 fold less increase in MAP compared to untreated control. The outcome of this study supports a synergistic antihypertensive and absence of competing mechanistic actions between the Amaranth extract and Amla seed extract on arterial function activity.

TABLE 1

Effect of Amaranth extract, Amla seed and combination on MAP in L-NAME induced hypertensive rats.

| Group | Mean arterial blood pressure (MAP) in mmHg | | | Percentage increase |
| --- | --- | --- | --- | --- |
| | Baseline | 2 Weeks | 4 Weeks | from baseline to 4 weeks |
| G1 | 96.2 | 96.8 | 96.4 | 0.2% |
| G2 | 96.1 | 142.8 | 175.4 | 82% |
| G3 | 95.8 | 120.4 | 112.2 | 17% |
| G4 | 96.4 | 134.2 | 148.4 | 54% |
| G5 | 96.0 | 109.8 | 98 | 2% |

Lipid Profile

Hypertension and hyperlipidemia are considered as two concomitant cardiovascular risk factors. The results of the current study indicated dyslipidemia in L-NAME-hypertensive rats evidenced by elevated serum triglycerides and cholesterol and LDL coupled with decreased level of HDL compared to normal control group (Table 2). Concomitant administration of Amaranth extract or Amla seed extract significantly modulated this dyslipidemic profile. A combination of Amaranth extract and Amla seed extract nearly normalized the concentration of triglycerides, total cholesterol, LDL, VLDL and HDL. The percentage improvement in total cholesterol and triglyceride was 97% and 95% respectively compared to untreated control. A combination of Amaranth extract and Amla seed extract showed 92% improvement in HDL cholesterol compared to untreated control. LDL and VLDL were improved by 96% and 95% compared with untreated control. According to our finding, a combination of Amaranth extract and Amla seed extract may contribute to the significant hypolipidemic effect observed in the treated groups.

TABLE 2

Effect of Amaranth extract, Amla seed extract and combination of amaranth extract and Amla seed extract on lipid profile of rats.

|  | G1 | G2 | G3 | G4 | G5 |
|---|---|---|---|---|---|
| Total cholesterol (mg/dl) | 85.2 | 124.4 | 115 | 105.8 | 86.4 |
| % Improvement compared to Group 2 |  |  | 24% | 47% | 97% |
| Triglycerides (mg/dl) | 96 | 122 | 115 | 109 | 97 |
| % Improvement compared to Group 2 |  |  | 27% | 50% | 96% |
| HDL (mg/dl) | 35 | 23 | 26 | 29 | 34 |
| % Improvement compared to Group 2 |  |  | 25% | 50% | 92% |
| LDL (mg/dl) | 31 | 77 | 66 | 55 | 33 |
| % Improvement compared to Group 2 |  |  | 24% | 48% | 96% |
| VLDL (mg/dl) | 19.2 | 24.4 | 23 | 21.8 | 19.4 |
| % Improvement compared to Group 2 |  |  | 27% | 50% | 96% |

Histopathology of the Heart

The histopathological lesion scoring of the heart of the different groups is summarized in table 3. The heart of the normotensive group showed a normal histological finding of the myocardium. The L-NAME hypertensive group revealed severe myocardia degeneration, necrosis, and fibrosis with mononuclear cell infiltration. The combination treatment was very effective and this group showed a significant reduction in all myocardial lesions. In Masson's trichrome—(MT) stained sections, the heart of L-NAME hypertensive rats showed extensive collagen fiber deposition and increased myocardial fibrosis compared to the normal controls. Groups that received Amaranth extract, Amla seed extract or combination showed marked attenuation of myocardial fibrosis and combination group was most effective. Myocardial degeneration, necrosis, and fibrosis were reduced to normal and the percentage improvement compared with untreated control was 98%, 91% and 92% respectively.

Aortic Intima Media Thickness

The results of the aortic media thickness are summarized in Table 4.

TABLE 4

Effect of Amaranth extract, Amla seed extract and combination on aortic intima media thickness.

| Group | Aortic intima media thickness (μm) | % improvement compared to Group 2 |
|---|---|---|
| Group 1 | 81 |  |
| Group 2 | 165 |  |
| Group 3 | 125 | 48% |
| Group 4 | 115 | 60% |
| Group 5 | 60 | 125% |

The aorta of the control group showed normal histological feature of tunica intima, tunica media, and tunica adventitia. The L-NAME hypertensive group showed focal tunica intima thickening and a significant increase in the thickness comparing to the control group. Treatment with Amaranth extract, Amla seed extract or combination of both resulted in a significant reduction in the intima media thickness when compared with the hypertensive group. Combination group showed a percentage improvement of 125% compared with the hypertensive group. The combination group was most effective in reducing the medial thickening.

Other modifications and variations to the invention will be apparent to those skilled in the art from the foregoing disclosure and teachings. Thus, while only certain embodiments have been specifically described herein, it will be apparent that numerous modifications may be made thereto without departing from the spirit and scope of the invention.

What is claimed is:

1. An oral composition comprising:
   a) a nitrate enriched water extract of Amaranth, and
   b) a bio-enhanced turmeric formulation,
   wherein a) comprises about 0.1% to about 70% nitrates by weight of the nitrate enriched water extract of Amaranth; about 1% to about 40% potassium by weight of the nitrate enriched water extract of Amaranth, and, about 0.1% free oxalic acid and oxalates by weight of the nitrate enriched water extract of Amaranth, and
   wherein b) comprises a curcuminoid mixture and an essential oil of turmeric, wherein the curcuminoid mixture consists of curcumin, demethoxycurcumin and

TABLE 3

Effect of Amaranth extract, Amla seed extract and combination on myocardium lesion scoring in L-NAME-induced hypertensive rats.

| | Lesion score | | | | | |
|---|---|---|---|---|---|---|
| Group | Myocardial degeneration | % improvement compared to Group 2 | Myocardial necrosis | % improvement compared to Group 2 | Inflammation | % improvement compared to Group 2 |
| G1 | 0.15 |  | 0.14 |  | 0.15 |  |
| G2 | 3.14 |  | 2.92 |  | 3.21 |  |
| G3 | 1.5 | 55% | 1.5 | 51% | 1.6 | 53% |
| G4 | 2.04 | 37% | 1.92 | 36% | 1.8 | 36% |
| G5 | 0.2 | 98% | 0.4 | 91% | 0.4 | 92% | bisdemethoxycurcumin, the essential oil of turmeric comprises about 45% by weight of the essential oil of turmeric, and a weight ratio of the curcuminoid mixture to the essential oil of turmeric ranges from about 1:1 to about 99:1, and wherein the oral composition comprises synergistic amounts of about 14.5 mg/kg to about 29 mg/kg of the composition wherein the composition is in a form selected from the group consisting of fast melt tablets, capsules, lozenges, and gums.

2. The composition of claim 1, wherein the nitrate enriched water extract of Amaranth comprises:
   greater than about 3% to about 20% nitrates by weight of the nitrate enriched water extract of Amaranth,
   about 1% to about 40% potassium by weight of the nitrate enriched water extract of Amaranth, and,
   about 0.1% free oxalic acid and oxalates by weight of the nitrate enriched water extract of Amaranth.

3. The composition of claim 1, wherein the nitrate enriched water extract of Amaranth comprises:
   greater than about 20% to about 70% nitrates by weight of the nitrate enriched water extract of Amaranth,
   about 1% to about 40% potassium by weight of the nitrate enriched water extract of Amaranth, and,
   about 0.1% free oxalic acid and oxalates by weight of the nitrate enriched water extract of Amaranth.

4. The composition of claim 1, wherein the nitrate enriched water extract of Amaranth comprises:
   about 9% nitrates by weight of the nitrate enriched water extract of Amaranth,
   about 18% potassium by weight of the nitrate enriched water extract of Amaranth, and,
   about 0.07% free oxalic acid and oxalates by weight of the nitrate enriched water extract of Amaranth.

5. The composition of claim 1, wherein the nitrate enriched water extract of Amaranth comprises:
   about 18% nitrates by weight of the nitrate enriched water extract of Amaranth,
   about 17% potassium by weight of the nitrate enriched water extract of Amaranth, and,
   about 0.09% free oxalic acid and oxalates by weight of the nitrate enriched water extract of Amaranth.

6. The composition of claim 1, wherein the nitrate enriched water extract of Amaranth comprises:
   about 70% nitrates by weight of the nitrate enriched water extract of Amaranth,
   about 25% potassium by weight of the nitrate enriched water extract of Amaranth, and,
   about 0.03% free oxalic acid and oxalates by weight of the nitrate enriched water extract of Amaranth.

7. The composition of claim 1, which is in a form selected from the group consisting of fast melt tablets, lozenge, candy, chewing gum, beverage, tablets, capsules, and pills.

* * * * *